US012269872B2

(12) United States Patent
Seder et al.

(10) Patent No.: US 12,269,872 B2
(45) Date of Patent: Apr. 8, 2025

(54) NEUTRALIZING ANTIBODIES TO PLASMODIUM FALCIPARUM CIRCUMSPOROZOITE PROTEIN AND THEIR USE

(71) Applicant: The United States of America, as represented by the Secretary, Department of Health and Human Services, Bethesda, MD (US)

(72) Inventors: Robert Seder, Chevy Chase, MD (US); Lawrence Wang, Bethesda, MD (US); Rachel Vistein, Bethesda, MD (US); Joseph Francica, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 790 days.

(21) Appl. No.: 17/608,381

(22) PCT Filed: May 4, 2020

(86) PCT No.: PCT/US2020/031345
§ 371 (c)(1),
(2) Date: Nov. 2, 2021

(87) PCT Pub. No.: WO2020/227228
PCT Pub. Date: Nov. 12, 2020

(65) Prior Publication Data
US 2022/0227853 A1 Jul. 21, 2022

Related U.S. Application Data

(60) Provisional application No. 62/842,590, filed on May 3, 2019.

(51) Int. Cl.
| | | |
|---|---|---|
| C07K 16/20 | (2006.01) |
| A61K 39/00 | (2006.01) |
| A61K 39/395 | (2006.01) |
| A61K 47/68 | (2017.01) |
| A61P 33/06 | (2006.01) |
| C07K 16/00 | (2006.01) |
| C07K 16/46 | (2006.01) |
| C12N 1/20 | (2006.01) |
| C12N 15/00 | (2006.01) |
| G01N 33/53 | (2006.01) |
| G01N 33/569 | (2006.01) |

(52) U.S. Cl.
CPC ........ *C07K 16/205* (2013.01); *A61K 47/6843* (2017.08); *A61P 33/06* (2018.01); *G01N 33/56905* (2013.01); *A61K 2039/505* (2013.01); *C07K 2317/21* (2013.01); *C07K 2317/34* (2013.01); *C07K 2317/565* (2013.01); *C07K 2317/567* (2013.01); *C07K 2317/72* (2013.01); *C07K 2317/76* (2013.01); *C07K 2317/92* (2013.01); *C07K 2317/94* (2013.01); *G01N 2333/445* (2013.01); *G01N 2469/10* (2013.01); *G01N 2800/26* (2013.01)

(58) Field of Classification Search
CPC .............. C07K 16/205; C07K 2317/21; C07K 2317/34; C07K 2317/565; C07K 2317/567; C07K 2317/72; C07K 2317/76; C07K 2317/92; C07K 2317/94; A61K 47/6843; A61K 2039/505; A61K 2039/55572; A61K 2039/55577; A61K 39/015; A61P 33/06; G01N 33/56905; G01N 2333/445; G01N 2469/10; G01N 2800/26; C12N 2730/10123; Y02A 50/30
See application file for complete search history.

(56) References Cited

U.S. PATENT DOCUMENTS 9,321,834 B2    4/2016  Gutierrez et al.
2024/0287166 A1*  8/2024  Weiner .................... A61P 33/06

FOREIGN PATENT DOCUMENTS

WO    WO 2018/193063 A2    10/2018
WO    WO 2018/209265 A1    11/2018

OTHER PUBLICATIONS

Kisalu NK, et al. A human monoclonal antibody prevents malaria infection by targeting a new site of vulnerability on the parasite. Nat Med. May 2018;24(4):408-416. doi: 10.1038/nm.4512. Epub Mar. 19, 2018. Erratum in: Nat Med. Jan. 2019;25(1):188-189. doi: 10.1038/s41591-018-0315-0. PMID: 29554083. (Year: 2018).*
Ahmad et al., "scFv antibody: principles and clinical application," *Clinical and Developmental Immunology* 2012: 980250 15 pages (e-Pub Mar. 15, 2012).
Barouch et al., "A Human T-Cell Leukemia Virus Type 1 Regulatory Element Enhances the Immunogenicity of Human Immunodeficiency Virus Type 1 DNA Vaccines in Mice and Nonhuman Primates," *Journal of Virology* 79(14): 8828-8834 (Jul. 2005).
Brühl et al., "Depletion of CCR5-expressing cells with bispecific antibodies and chemokine toxins: a new strategy in the treatment of chronic inflammatory diseases and HIV," *Journal of Immunology* 166: 2420-2426 (2001).

(Continued)

*Primary Examiner* — Maher M Haddad
*Assistant Examiner* — Alec Jon Peters
(74) *Attorney, Agent, or Firm* — Klarquist Sparkman, LLP

(57) ABSTRACT

Antibodies and antigen binding fragments that specifically bind to *P. falciparum* circumsporozoite protein are disclosed. Nucleic acids encoding these antibodies, vectors and host cells are also provided. The disclosed antibodies, antigen binding fragments, nucleic acids and vectors can be used, for example, to inhibit a *P. falciparum* infection.

31 Claims, 25 Drawing Sheets
Specification includes a Sequence Listing.

(56) References Cited

OTHER PUBLICATIONS

Charonvit et al., Development of two monoclonal antibodies against *Plasmodium falciparum* sporozoite surface protein 2 and mapping of B-Cell epitopes, *Infection and Immunity* 65(8): 3430-3437 (Aug. 1997).

Chen et al., "Selection and analysis of an optimized anti-VEGF antibody: crystal structure of an affinity-matured Fab in complex with antigen," *J. Mol. Biol.* 293: 865-881 (1999).

Clement et al., "Validation of an enzyme-linked immunosorbent assay for the quantification of human IgG directed against the repeat region of the circumsporozoite protein of the parasite *Plasmodium falciparum,*" *Malaria Journal* 11: 384, 15 pages (2012).

Dall'Acqua et al., "Properties of human IgG1s engineered for enhanced binding to the neonatal Fc receptor (FcRn)," *Journal of Biological Chemistry* 281(33): 23514-23524 (Aug. 18, 2006).

Draper et al., "Malaria vaccines: Recent advances and new horizons," *Cell Host & Microbe* 24: 43-56 (Jul. 11, 2018).

Espinosa et al., "Proteolytic cleavage of the *Plasmodium falciparum* circumsporozoite protein is a target of protective antibodies," *Journal of Infectious Diseases* 212: 1111-1119 (Oct. 1, 2015).

Foquet et al., "Vaccine-induced monoclonal antibodies targeting circumsporozoite protein prevent Plasmodium falciparum infection," *Journal of Clinical Investigation* 124(1): 140-144 (Jan. 2014).

Gardner et al., "AAV-expressed eCD4-Ig provides durable protection from multiple SHIV challenges," *Nature* 519(7541): 87-91 (Sep. 5, 2015).

Griffiths et al., "Human anti-self antibodies with high specificity from phage display libraries," *EMBO Journal* 12(2): 725-734 (1993).

Hinton et al., "An Engineered Human IgG1 Antibody with Longer Serum Half-Life," *Journal of Immunology* 176:346-356 (2006).

Imkeller et al., "Antihomotypic affinity maturation improves human B cell responses against a repetitive epitope," *Science* 360: 1358-1362 (Jun. 22, 2018).

International Search Report and Written Opinion from parent PCT Application No. PCT/US2020/031345, 20 pages (mailed Nov. 3, 2020).

Ishizuka et al., "Protection against malaria at 1 year and immune correlates following PfSPZ vaccination," *Nature Medicine* 22(6): 614-623 (Jun. 2016).

Johnson et al., "Vector-mediated gene transfer engenders long-lived neutralizing activity and protection against SIV infection in monkeys," *Nature Medicine* 15(8): 901-906 (2009).

Kisalu et al., "A human monoclonal antibody prevents malaria infection by targeting a new site of vulnerability on the parasite," Nature Medicine 24(4): 408-416 (May 2018).

Lazar et al., "Engineered antibody Fc variants with enhanced effector function," *PNAS* 103(11): 4005-4010 (Mar. 14, 2006).

Löffler et al., "A recombinant bispecific single-chain antibody, CD19 3 CD3, induces rapid and high lymphoma-directed cytotoxicity by unstimulated T lymphocytes," *Blood* 95(6): 2098-2103 (Mar. 15, 2000).

Mack et al., "A small bispecific antibody construct expressed as a functional single-chain molecule with high tumor cell cytotoxicity," *PNAS* 92: 7021-7025 (Jul. 1995).

Mack et al., "Biologic properties of a bispecific single-chain antibody directed against 17-1A (EpCAM) and CD3 tumor cell-dependent T cell stimulation and cytotoxic activity," *Journal of Immunology* 158: 3965-3970 (1997).

Mellouk et al., "Evaluation of an in vitro assay aimed at measuring protective antibodies against sporozoites," *Bulletin of the World Health Organization* 68(Suppl.): 52-59 (1990).

Oyen et al., "Cryo-EM structure of *P. falciparum* circumsporozoite protein with a vaccine-elicited antibody is stabilized by somatically mutated inter-Fab contacts," *Sci. Adv.* 4: eaau8529, 10 pages (Oct. 10, 2018).

Oyen et al., "Structural basis for antibody recognition of the NANP repeats in *Plasmodium falciparum* circumsporozoite protein," *PNAS* 114(48): E10438-E10445 (e-Pub Nov. 14, 2017).

Oyen et al., "Structure and mechanism of monoclonal antibody binding to the junctional epitope of *Plasmodium falciparum* circumsporozoite protein," *PLOS Pathogens* 16(3): 22 pages (Mar. 9, 2020).

Petkova et al., "Enhanced half-life of genetically engineered human IgG1 antibodies in a humanized FcRn mouse model: potential application in humorally mediated autoimmune disease," *International Immunology* 18(12): 1759-1769 (e-Pub Oct. 31, 2006).

Scally and Julien, "Peek-Peak-Pique: repeating motifs of subtle variance are targets for potent malaria antibodies," *Immunity* 48: 852-854 (May 15, 2018).

Schoonjans et al., "Fab chains as an efficient heterodimerization scaffold for the production of recombinant bispecific and trispecific antibody derivatives," *Journal of Immunology* 165: 7050-7057 (2000).

Tan et al., "A public antibody lineage that potently inhibits malaria infection by dual binding to the circumsporozoite protein," *Nature Medicine* 24(4): 401-407 (May 2018).

Triller et al., "Natural parasite exposure induces protective human anti-malarial antibodies," *Immunity* 47: 1197-1209.e10 (Dec. 19, 2017).

Willems et al., "Optimizing expression and purification from cell culture medium of trispecific recombinant antibody derivatives," *Journal of Chromatography B* 786: 161-176 (2003).

Wirtz et al., "Comparative testing of monoclonal antibodies against *Plasmodium falciparum* sporozoites for ELISA development," *Bulletin of the World Health Organization* 65(1): 39-45 (1987).

Yamane-Ohnuki et al., "Establishment of FUT8 knockout Chinese hamster ovary cells: an ideal host cell line for producing completely defucosylated antibodies with enhanced antibody-dependent cellular cytotoxicity," *Biotechnology and Bioengineering* 87(5): 614-622 (e-Pub Aug. 6, 2004).

Zalevsky et al., "Enhanced antibody half-life improves in vivo activity," *Nat Biotechnol.* 28(2): 157-159 (Feb. 2010).

* cited by examiner

FIG. 3C

| | | | |
|---|---|---|---|
| 5/3 | 19/3 | 23/4 | FL |

Bars labeled (bottom to top): N-terminus | R1 Repeats | 1 NPDP | 3 NVDP | NANP repeats | C-terminus

SEQ ID NO: 29 — 1 NPDP
SEQ ID NO: 30 — NVDP
SEQ ID NO: 31 — NANP

- 5/3: 1 NPDP | 3 NVDP | 5 NANP
- 19/3: 1 NPDP | 3 NVDP | 19 NANP
- 23/4: 1 NPDP | 4 NVDP | 23 NANP
- FL: 1 NPDP | 4 NVDP | 38 NANP

FIG. 5C *in vivo* traversal

Bursting

SEQUENCE LISTING

```
<160> NUMBER OF SEQ ID NOS: 42

<210> SEQ ID NO 1
<211> LENGTH: 120
<212> TYPE: PRT
<213> ORGANISM: Artificial Sequence
<220> FEATURE:
<223> OTHER INFORMATION: Monoclonal antibody sequence

<400> SEQUENCE: 1

Gln Val Lys Leu Val Glu Ser Gly Gly Gly Val Val Gln Pro Gly Arg
1               5                   10                  15

Ser Leu Arg Leu Ser Cys Glu Ala Ser Gly Phe Ile Phe Ser Thr Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Ile Tyr Tyr Ala Asp Ser Val
    50                  55                  60

Lys Gly Arg Phe Thr Ile Ser Arg Asp Asn Ser Lys Asn Thr Val Phe
65                  70                  75                  80

Met Gln Met Asp Ser Leu Arg Ala Glu Asp Thr Ala Val Tyr Tyr Cys
                85                  90                  95

His Arg Asn Phe Tyr Asp Gly Ser Gly Pro Phe Asp Tyr Trp Gly Gln
            100                 105                 110

Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Monoclonal antibody sequence

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Phe Ile Ser Arg Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Glu Thr His Phe Thr Leu Thr Ile Ser Ser Leu Gln Pro
65                  70                  75                  80

Asp Asp Val Ala Thr Tyr Tyr Cys Gln Glu Tyr Thr Ser Tyr Gly Arg
                85                  90                  95

Thr Phe Gly Gln Gly Thr Lys Val Glu Ile Lys
            100                 105
```

```
<210> SEQ ID NO 3
<211> LENGTH: 8
<212> TYPE: PRT
<213> ORGANISM: Artificial Sequence
<220> FEATURE:
<223> OTHER INFORMATION: Monoclonal antibody sequence

<400> SEQUENCE: 3

Gly Phe Ile Phe Ser Thr Tyr Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Monoclonal antibody sequence

<400> SEQUENCE: 4

Ile Trp Phe Asp Gly Ser Asn Ile
1               5

<210> SEQ ID NO 5
<211> LENGTH: 13
<212> TYPE: PRT
<213> ORGANISM: Artificial Sequence
<220> FEATURE:
<223> OTHER INFORMATION: Monoclonal antibody sequence

<400> SEQUENCE: 5

His Arg Asn Phe Tyr Asp Gly Ser Gly Pro Phe Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Monoclonal antibody sequence

<400> SEQUENCE: 6

Gln Phe Ile Ser Arg Trp
1               5

<210> SEQ ID NO 7
<211> LENGTH: 3
<212> TYPE: PRT
<213> ORGANISM: Artificial Sequence
<220> FEATURE:
<223> OTHER INFORMATION: Monoclonal antibody sequence

<400> SEQUENCE: 7

Lys Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Monoclonal antibody sequence

<400> SEQUENCE: 8

Gln Glu Tyr Thr Ser Tyr Gly Arg Thr
1               5
```

```
<210> SEQ ID NO 9
<211> LENGTH: 469
<212> TYPE: PRT
<213> ORGANISM: Artificial Sequence
<220> FEATURE:
<223> OTHER INFORMATION: Monoclonal antibody sequence

<400> SEQUENCE: 9

Met Gly Trp Ser Cys Ile Ile Leu Phe Leu Val Ala Thr Ala Thr Gly
1               5                   10                  15

Val His Ser Gln Val Lys Leu Val Glu Ser Gly Gly Val Val Gln
            20                  25                  30

Pro Gly Arg Ser Leu Arg Leu Ser Cys Glu Ala Ser Gly Phe Ile Phe
            35                  40                  45

Ser Thr Tyr Gly Met His Trp Val Arg Gln Ala Pro Gly Lys Gly Leu
        50                  55                  60

Glu Trp Val Ala Val Ile Trp Phe Asp Gly Ser Asn Ile Tyr Tyr Ala
65                  70                  75                  80

Asp Ser Val Lys Gly Arg Phe Thr Ile Ser Arg Asp Asn Ser Lys Asn
                85                  90                  95

Thr Val Phe Met Gln Met Asp Ser Leu Arg Ala Glu Asp Thr Ala Val
            100                 105                 110

Tyr Tyr Cys His Arg Asn Phe Tyr Asp Gly Ser Gly Pro Phe Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365
```

```
Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 10
<211> LENGTH: 233
<212> TYPE: PRT
<213> ORGANISM: Artificial Sequence
<220> FEATURE:
<223> OTHER INFORMATION: Monoclonal antibody sequence

<400> SEQUENCE: 10

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
                20                  25                  30

Ser Val Gly Asp Arg Val Thr Ile Thr Cys Arg Ala Ser Gln Phe Ile
            35                  40                  45

Ser Arg Trp Leu Ala Trp Tyr Gln Gln Lys Pro Gly Lys Ala Pro Lys
        50                  55                  60

Leu Leu Ile Tyr Lys Ala Ser Ser Leu Glu Ser Gly Val Pro Ser Arg
65                  70                  75                  80

Phe Ser Gly Ser Gly Ser Glu Thr His Phe Thr Leu Thr Ile Ser Ser
                85                  90                  95

Leu Gln Pro Asp Asp Val Ala Thr Tyr Tyr Cys Gln Glu Tyr Thr Ser
            100                 105                 110

Tyr Gly Arg Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 11
<211> LENGTH: 360
```

<212> TYPE: DNA
<213> ORGANISM: Artificial Sequence
<220> FEATURE:
<223> OTHER INFORMATION: Monoclonal antibody sequence

<400> SEQUENCE: 11

```
caggtgaagc tggtggagtc tggggggaggc gtggtccagc ctgggaggtc cctgagactc    60
tcctgtgaag cgtctggatt catcttcagt acctatggca tgcactgggt ccgccaggct   120
ccaggcaagg gctggagtg gtggcagtt atatggtttg atggaagtaa catatactat   180
gcagactccg tgaagggccg attcaccatc tccagagaca attccaagaa cacggtgttt   240
atgcaaatgg acagcctgag agccgaggac acggctgtgt attactgcca ccgcaatttt   300
tatgatggta gtggtcccctt tgactattgg ggccagggaa ccctggtcac cgtctcctca   360
```

<210> SEQ ID NO 12
<211> LENGTH: 360
<212> TYPE: DNA
<213> ORGANISM: Artificial Sequence
<220> FEATURE:
<223> OTHER INFORMATION: Monoclonal antibody sequence

<400> SEQUENCE: 12

```
caggtgaagc tggtggagtc tggaggagga gtggtgcagc caggccggtc tctgagactg    60
agctgcgagg cctccggctt catctttagc acctacggaa tgcactgggt gcggcaggca   120
cctggcaagg gcctggagtg ggtggccgtg atctggttcg acggctccaa catctactat   180
gccgattctg tgaagggcag gttcaccatc tctcgcgaca cagcaagaa tacagtgttt   240
atgcagatgg acagcctgcg ggccgaggat acagccgtgt actattgtca caggaattttc   300
tacgacggct ccggccccctt tgattattgg ggccagggca ccctggtgac agtgagctcc   360
```

<210> SEQ ID NO 13
<211> LENGTH: 321
<212> TYPE: DNA
<213> ORGANISM: Artificial Sequence
<220> FEATURE:
<223> OTHER INFORMATION: Monoclonal antibody sequence

<400> SEQUENCE: 13

```
gacatccaga tgacccagtc tccttccacc ctgtctgcat ctgtaggaga cagagtcacc    60
atcacttgcc gggccagtca gtttattagt cgttggttgg cctggtatca gcagaaacca   120
gggaaagccc ctaagctcct gatctataag gcgtctagtt tagaaagtgg ggtcccatca   180
aggttcagcg gcagtggatc tgagacacat ttcactctca ccatcagcag cctgcagcct   240
gatgatgttg caacttatta ctgccaagag tacactagtt atggtaggac gttcggccaa   300
gggaccaagg tggaaatcaa a                                            321
```

<210> SEQ ID NO 14
<211> LENGTH: 321
<212> TYPE: DNA
<213> ORGANISM: Artificial Sequence
<220> FEATURE:
<223> OTHER INFORMATION: Monoclonal antibody sequence

<400> SEQUENCE: 14

```
gacatccaga tgacccagtc cccatctaca ctgagcgcct ccgtgggcga tagggtgacc    60
atcacatgca gagcctctca gttcatcagc aggtggctgg cctggtacca gcagaagccc   120
ggcaaggccc ctaagctgct gatctataag gcaagctccc tggagtccgg agtgccatct   180
```

```
cgcttctctg gcagcggctc cgagacacac tttaccctga caatctctag cctgcagccc      240
gacgatgtgg ccacctacta ttgtcaggag tacacctcct atggccggac atttggccag      300
ggcaccaagg tggagatcaa g                                                 321
```

```
<210> SEQ ID NO 15
<211> LENGTH: 121
<212> TYPE: PRT
<213> ORGANISM: Artificial Sequence
<220> FEATURE:
<223> OTHER INFORMATION: Monoclonal antibody sequence

<400> SEQUENCE: 15
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Arg Leu Glu Trp Met
        35                  40                  45

Gly Trp Ile Lys Ala Gly Asn Gly Asn Thr Arg Tyr Ser Gln Lys Phe
    50                  55                  60

Gln Asp Arg Val Thr Ile Thr Arg Asp Thr Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Leu Leu Thr Val Leu Thr Pro Asp Asp Ala Phe Asp Ile Trp Gly
            100                 105                 110

Gln Gly Thr Met Val Thr Val Ser Ser
        115                 120

```
<210> SEQ ID NO 16
<211> LENGTH: 113
<212> TYPE: PRT
<213> ORGANISM: Artificial Sequence
<220> FEATURE:
<223> OTHER INFORMATION: Monoclonal antibody sequence

<400> SEQUENCE: 16
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Asn Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ser Pro Leu Thr Phe Gly Gly Gly Thr Lys Val Glu Ile
            100                 105                 110

Lys

```
<210> SEQ ID NO 17
<211> LENGTH: 470
<212> TYPE: PRT
<213> ORGANISM: Artificial Sequence
<220> FEATURE:
```

-continued

<223> OTHER INFORMATION: Monoclonal antibody sequence

<400> SEQUENCE: 17

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Ala Ile His Trp Val Arg Gln Ala Pro Gly Gln Arg Leu
    50                  55                  60

Glu Trp Met Gly Trp Ile Lys Ala Gly Asn Gly Asn Thr Arg Tyr Ser
65                  70                  75                  80

Gln Lys Phe Gln Asp Arg Val Thr Ile Thr Arg Asp Thr Ser Thr Thr
                85                  90                  95

Thr Ala Tyr Met Glu Leu Ser Ser Leu Arg Ser Glu Asp Thr Ala Val
            100                 105                 110

Tyr Tyr Cys Ala Leu Leu Thr Val Leu Thr Pro Asp Ala Phe Asp
        115                 120                 125

Ile Trp Gly Gln Gly Thr Met Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
    275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400
```

-continued

```
Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 18
<211> LENGTH: 239
<212> TYPE: PRT
<213> ORGANISM: Artificial Sequence
<220> FEATURE:
<223> OTHER INFORMATION: Monoclonal antibody sequence

<400> SEQUENCE: 18

Met Gly Trp Ser Cys Ile Ile Leu Phe Leu Val Ala Thr Ala Thr Gly
1               5                   10                  15

Val His Ser Asp Ile Val Met Thr Gln Ser Pro Asp Ser Leu Ala Val
            20                  25                  30

Ser Leu Gly Glu Arg Ala Thr Ile Asn Cys Lys Ser Ser Gln Ser Val
            35                  40                  45

Leu Tyr Ser Ser Asn Asn Lys Asn Tyr Leu Ala Trp Tyr Gln Gln Lys
            50                  55                  60

Pro Gly Gln Pro Pro Asn Leu Leu Ile Tyr Trp Ala Ser Thr Arg Gln
65                  70                  75                  80

Ser Gly Val Pro Asp Arg Phe Ser Gly Ser Gly Ser Gly Thr Asp Phe
            85                  90                  95

Thr Leu Thr Ile Ser Ser Leu Gln Ala Glu Asp Val Ala Val Tyr Tyr
            100                 105                 110

Cys His Gln Tyr Tyr Ser Ser Pro Leu Thr Phe Gly Gly Gly Thr Lys
            115                 120                 125

Val Glu Ile Lys Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 19
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 19
```

```
Pro Ala Asp Gly Asn Pro Asp Pro Asn Ala Asn Pro Asn Val Asp
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 20

Asn Pro Asp Pro Asn Ala Asn Pro Asn Val Asp Pro Asn Ala Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 21

Asn Ala Asn Pro Asn Val Asp Pro Asn Ala Asn Pro Asn Val Asp
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 22

Asn Val Asp Pro Asn Ala Asn Pro Asn Val Asp Pro Asn Ala Asn
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 23

Asn Val Asp Pro Asn Ala Asn Pro Asn Ala Asn Pro Asn Ala Asn
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 24

Asn Ala Asn Pro Asn Ala Asn Pro Asn Ala Asn Pro Asn Ala Asn
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 25
```

```
Asn Ala Asn Pro Asn Ala Asn Pro Asn Val Asp Pro Asn Ala Asn
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 26

Asn Ala Asn Pro Asn Val Asp Pro Asn Ala Asn Pro Asn Ala Asn
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Plasmodium falciparum PfCSP peptide

<400> SEQUENCE: 27

Asn Ala Asn Pro Asn Ala Asn Pro Asn Ala Asn Pro Asn Lys Asn
1               5                   10                  15

<210> SEQ ID NO 28
<211> LENGTH: 397
<212> TYPE: PRT
<213> ORGANISM: Plasmodium falciparum

<400> SEQUENCE: 28

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220
```

-continued

```
Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
            245                 250                 255

Asn Ala Asn Pro Asn Ala Asn Pro Asn Ala Asn Pro Asn Ala Asn Pro
        260                 265                 270

Asn Lys Asn Asn Gln Gly Asn Gly Gln Gly His Asn Met Pro Asn Asp
    275                 280                 285

Pro Asn Arg Asn Val Asp Glu Asn Ala Asn Ala Asn Ser Ala Val Lys
        290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
            325                 330                 335

Thr Cys Gly Asn Gly Ile Gln Val Arg Ile Lys Pro Gly Ser Ala Asn
        340                 345                 350

Lys Pro Lys Asp Glu Leu Asp Tyr Ala Asn Asp Ile Glu Lys Lys Ile
    355                 360                 365

Cys Lys Met Glu Lys Cys Ser Ser Val Phe Asn Val Val Asn Ser Ser
370                 375                 380

Ile Gly Leu Ile Met Val Leu Ser Phe Leu Phe Leu Asn
385                 390                 395

<210> SEQ ID NO 29
<211> LENGTH: 4
<212> TYPE: PRT
<213> ORGANISM: Artificial Sequence
<220> FEATURE:
<223> OTHER INFORMATION: Plasmodium falciparum PfCSP peptide

<400> SEQUENCE: 29

Asn Pro Asp Pro
1

<210> SEQ ID NO 30
<211> LENGTH: 4
<212> TYPE: PRT
<213> ORGANISM: Artificial Sequence
<220> FEATURE:
<223> OTHER INFORMATION: Plasmodium falciparum PfCSP peptide

<400> SEQUENCE: 30

Asn Val Asp Pro
1

<210> SEQ ID NO 31
<211> LENGTH: 4
<212> TYPE: PRT
<213> ORGANISM: Artificial Sequence
<220> FEATURE:
<223> OTHER INFORMATION: Plasmodium falciparum PfCSP peptide

<400> SEQUENCE: 31

Asn Ala Asn Pro
1

<210> SEQ ID NO 32
<211> LENGTH: 4
<212> TYPE: PRT
<213> ORGANISM: Artificial Sequence
<220> FEATURE:
<223> OTHER INFORMATION: Plasmodium falciparum PfCSP peptide
```

```
<400> SEQUENCE: 32

Asn Pro Asn Val
1

<210> SEQ ID NO 33
<211> LENGTH: 30
<212> TYPE: PRT
<213> ORGANISM: Artificial Sequence
<220> FEATURE:
<223> OTHER INFORMATION: Plasmodium falciparum PfCSP peptide

<400> SEQUENCE: 33

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala
            20                  25                  30

<210> SEQ ID NO 34
<211> LENGTH: 36
<212> TYPE: PRT
<213> ORGANISM: Artificial Sequence
<220> FEATURE:
<223> OTHER INFORMATION: Plasmodium falciparum PfCSP peptide

<400> SEQUENCE: 34

Asn Ala Asn Pro Asn Ala Asn Pro Asn Ala Asn Pro Asn Ala Asn Pro
1               5                   10                  15

Asn Ala Asn Pro Asn Ala Asn Pro Asn Ala Asn Pro Asn Ala Asn Pro
            20                  25                  30

Asn Ala Asn Pro
        35

<210> SEQ ID NO 35
<211> LENGTH: 12
<212> TYPE: PRT
<213> ORGANISM: Artificial Sequence
<220> FEATURE:
<223> OTHER INFORMATION: Plasmodium falciparum PfCSP peptide

<400> SEQUENCE: 35

Asn Ala Asn Pro Asn Ala Asn Pro Asn Ala Asn Pro
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Plasmodium falciparum PfCSP peptide

<400> SEQUENCE: 36

Asn Ala Asn Pro Asn Ala Asn Pro
1               5

<210> SEQ ID NO 37
<211> LENGTH: 4
<212> TYPE: PRT
<213> ORGANISM: Artificial Sequence
<220> FEATURE:
<223> OTHER INFORMATION: Plasmodium falciparum PfCSP peptide

<400> SEQUENCE: 37

Asp Pro Asn Ala
1
```

```
<210> SEQ ID NO 38
<211> LENGTH: 4
<212> TYPE: PRT
<213> ORGANISM: Artificial Sequence
<220> FEATURE:
<223> OTHER INFORMATION: Plasmodium falciparum PfCSP peptide

<400> SEQUENCE: 38

Asn Pro Asn Ala
1

<210> SEQ ID NO 39
<211> LENGTH: 8
<212> TYPE: PRT
<213> ORGANISM: Artificial Sequence
<220> FEATURE:
<223> OTHER INFORMATION: Plasmodium falciparum PfCSP peptide

<400> SEQUENCE: 39

Asn Val Asp Pro Asn Ala Asn Pro
1               5

<210> SEQ ID NO 40
<211> LENGTH: 43
<212> TYPE: PRT
<213> ORGANISM: Artificial Sequence
<220> FEATURE:
<223> OTHER INFORMATION: Plasmodium falciparum PfCSP peptide

<400> SEQUENCE: 40

Pro Glu Ser Ser Ser Asn Pro Asp Cys Asn Ala Asn Pro Asn Val Asp
1               5                   10                  15

Pro Asn Glu Asp Leu Ile Lys Lys Cys Glu Lys Ile Asn Val Pro Thr
            20                  25                  30

Glu Glu Ile Lys Lys Glu Ile Glu Glu Lys Lys
        35                  40

<210> SEQ ID NO 41
<211> LENGTH: 16
<212> TYPE: PRT
<213> ORGANISM: Artificial Sequence
<220> FEATURE:
<223> OTHER INFORMATION: Plasmodium falciparum PfCSP peptide

<400> SEQUENCE: 41

Asn Ala Asn Pro Asn Ala Asn Pro Asn Ala Asn Pro Asn Ala Asn Pro
1               5                   10                  15

<210> SEQ ID NO 42
<211> LENGTH: 24
<212> TYPE: PRT
<213> ORGANISM: Artificial Sequence
<220> FEATURE:
<223> OTHER INFORMATION: Plasmodium falciparum PfCSP peptide

<400> SEQUENCE: 42

Asn Ala Asn Pro Asn Ala Asn Pro Asn Ala Asn Pro Asn Ala Asn Pro
1               5                   10                  15

Asn Ala Asn Pro Asn Ala Asn Pro
            20
```

NEUTRALIZING ANTIBODIES TO *PLASMODIUM FALCIPARUM* CIRCUMSPOROZOITE PROTEIN AND THEIR USE

CROSS REFERENCE TO RELATED APPLICATION

This is a § 371 U.S. national stage of International Application No. PCT/US2020/031345, filed May 4, 2020, which claims priority to U.S. Provisional Application No. 62/842,590, filed May 3, 2019, which is incorporated by reference in its entirety.

FIELD

This relates to monoclonal antibodies and antigen binding fragments that specifically bind to *Plasmodium falciparum* (*P. falciparum* or Pf) circumsporozoite protein (CSP) and their use, for example, in methods of inhibiting *P. falciparum* infection in a subject.

BACKGROUND

Malaria ranks as one of the world's deadliest infectious diseases, with approximately 300 million cases per year. Malaria in humans is caused by five species of the *Plasmodium* parasite: *P. falciparum, P. vivax, P. ovale, P. knowlesi* and *P. malariae. P. falciparum* causes the most severe form of malaria disease, leading to the death of about ~500,000 people annually, most of whom are young children.

Each of the *Plasmodium* species that infect humans is transmitted through the bite of an infected female *Anopheles* mosquito, which introduces *Plasmodium* sporozoites into the bloodstream of the human host. The major protein on the surface of the infecting *P. falciparum* sporozoites is the circumsporozoite protein (PfCSP) and provides a major target for antibodies and vaccines. The sporozoites rapidly reach the liver where they are sequestered by hepatocytes and undergo asexual expansion. One week later, the infected hepatocytes rupture and release mature parasites, the merozoites. These then begin the erythrocytic phase of malaria by attaching to and invading red blood cells, or erythrocytes. The invasion of the erythrocytes by the malarial parasites leads to malarial pathogenesis and clinical infection.

There is no FDA approved vaccine for malaria. Moreover, malarial parasites are increasingly becoming resistant to antimalarial drugs used to treat the disease. Therefore, preventive interventions to inhibit malaria infection are urgently needed for limiting morbidity, mortality, and ultimately eliminating malaria.

SUMMARY

This disclosure provides monoclonal antibodies and antigen binding fragments directed against PfCSP. In one example, data shows that passive transfer of the L9 human monoclonal antibody confers sterile protection in an animal model of malaria infection containing PfCSP, and also that this antibody is more potent for inhibiting malaria infection that prior PfCSP monoclonal antibodies.

In some embodiments, the antibody or antigen binding fragment comprises a heavy chain variable region ($V_H$) comprising a heavy chain complementarity determining region (HCDR)1, a HCDR2, and a HCDR3 of the $V_H$ set forth as SEQ ID NO: 1 (L9 $V_H$) and a light chain variable region ($V_L$) comprising a light chain variable region (LCDR)1, a LCDR2, and a LCDR3 of the $V_L$ set forth as SEQ ID NO: 2 (L9 $V_L$).

Also disclosed are compositions including the antibodies and antigen binding fragments, nucleic acids encoding the antibodies and antigen binding fragments, expression vectors comprising the nucleic acids, and isolated host cells that comprise the nucleic acids. In several embodiments, the nucleic acid molecule encoding a disclosed antibody or antigen binding fragment can be a cDNA molecule that encodes the antibody or antigen binding fragment. In additional embodiments, the nucleic acid molecule can be a bicistronic expression construct encoding the $V_H$ and $V_L$ of the antibody or antigen binding fragment.

The disclosed antibodies and antigen binding fragments potently neutralize PfCSP expressed on infectious sporozoites in vivo. Accordingly, a method is disclosed for inhibiting (including preventing) *P. falciparum* infection in a subject. The method comprises administering an effective amount (that is, an amount effective to inhibit *P. falciparum* infection in a subject) of one or more of the disclosed antibodies, antigen binding fragments, nucleic acid molecules, vectors, or compositions, to the subject, such as a subject at risk of or having a *P. falciparum* infection.

The antibodies, antigen binding fragments, nucleic acid molecules, vectors, and compositions disclosed herein can be used for a variety of additional purposes, such as for diagnosing *P. falciparum* infection in a subject, or detecting *P. falciparum* in a sample.

The foregoing and other features and advantages of this disclosure will become more apparent from the following detailed description of several embodiments, which proceeds with reference to the accompanying figures.

BRIEF DESCRIPTION OF THE FIGURES

(FIG. 1A) Parasite liver burden reduction (bioluminescence; total flux, photons/sec) in mice 40 hrs post-infection (hpi; n=15/group; data pooled from three independent experiments) mediated by 100 µg CIS43 or L9 administered 2 hours before intravenous (IV) challenge with 2,000 Pb-PfCSP. (FIG. 1B) Parasitemia reduction in mice 7 days post-infection (dpi) mediated by 50 (n=10/group; data pooled from two independent experiments) or 100 µg (n=15/group) CIS43 or L9 administered 3 days before intradermal (ID) challenge with 5,000 Pb-PfCSP. (FIG. 1C) Serum mAb titers 2 hours, 24 hours, and 7 days after administration of 50 or 100 µg CIS43 or L9 in separate mice (n=5/group) determined through ELISA. P values were determined using a two-way ANOVA with Bonferronni's correction. (FIG. 1D) Left: Liver burden reduction (*P. falciparum* 18S rRNA normalized to number of human hepatocytes) in FRG-huHep mice (n=5/group) treated with 50 or 10 µg L9 and challenged IV with 100,000 PfSPZ. Right: Serum mAb titers in challenged FRG-huHep mice. Differences between VRC01 (anti-HIV-1 isotype control IgG) and L9 were determined using the two-tailed Mann-Whitney test. (FIG. 1E) Schematic of PfCSP in the 3D7 reference strain depicting the N-terminus (with region 1, R1), repeat region (with color-coded overlapping 15mer peptides 20-61), and C-terminus. Every NPNV (SEQ ID NO: 32) motif in each peptide is underlined. (FIG. 1F) CIS43 and L9 binding to peptides 20-61 by ELISA (MFI, median fluorescence intensity). (FIG. 1G) Competition ELISA (AUC, area under the curve) of L9 binding to rPfCSP with varying concentrations of peptide 22 (WT, leftmost bar)

or variant peptides (subsequent bars) where the indicated residue was mutated to alanine or serine. In FIGS. 1A and 1B, P values were determined by comparing L9 to CIS43 and untreated control using the Kruskal-Wallis test with Dunn's correction.

(FIG. 2A) Binding of varying concentrations of PfCSP mAbs to rPfCSP determined through ELISA. $OD_{450}$ nm, optical density at 450 nm, is plotted. (FIG. 2B) Binding of varying concentrations of PfCSP mAbs to Pb-PfCSP SPZ determined through flow cytometry. Median fluorescence intensity (MFI) of the mAb-bound SPZ is plotted. (FIGS. 2C-2D) Competition ELISA of PfCSP mAbs binding to rPfCSP in the presence of varying concentrations of peptides 20-61 (shown in schematic of rPfCSP). The $IC_{50}$ for competition by each peptide is depicted. (FIG. 2E) Binding of varying concentrations of PfCSP mAbs to NPNA (SEQ ID NO: 38)-containing peptides of increasing length determined through ELISA and expressed as AUC. $(NANP)_1$ (SEQ ID NO: 31) is composed of one NANP (SEQ ID NO: 31; $(NANP)_9$ (SEQ ID NO: 34) is composed of 9 NANP (SEQ ID NO: 31) repeats. All data are representative of two independent experiments.

FIGS. 3A-3E. Isothermal titration calorimetry (ITC) of mAb binding to rPfCSP. (FIG. 3A) Left: schematics of the repeat region of wild-type rPfCSP (rPfCSP_WT) and rPfCSP with all four NVDP (SEQ ID NO: 30) mutated to NANP (SEQ ID NO: 31) (rPfCSP_ΔABCD); N- and C-termini are identical but were omitted. Right graphs: ITC binding analyses of L9 IgG to rPfCSP_WT and rPfCSP_ΔABCD. Top, dQ/dt (heat flow, Q, as a function of time); the bottom graphs show the integrated heat associated with each IgG injection shown as a function of the molar ratio between IgG antigen binding sites and rPfCSP in the calorimetric cell. The line in the bottom graphs represents the result from best nonlinear least squares fit of the data. Dissociation constant ($K_D$), change in Gibbs energy (ΔG), enthalpy (ΔH), entropy contribution to Gibbs energy (−TΔS), and stoichiometry (N) of binding are shown. ITC data was fit to a two-step binding model if the IgG titrant bound to two sets of sites with different affinity values. The first set of high-affinity sites is saturated at lower IgG concentrations before the second set of lower-affinity sites. (FIG. 3B) ITC binding analyses of CIS43, 311, 317, 1210, mAb10, and MGU12 IgG to rPfCSP_WT. (FIG. 3C) Schematics of full-length (FL) rPfCSP and rPfCSP mutants with truncated repeat regions (23/4, 19/3, 5/3 NANP/NVDP (SEQ ID NO: 31/SEQ ID NO: 30) repeats) and identical N- and C-termini. (FIG. 3D) Aggregate stoichiometry (binding events 1+2; no. of binding sites) of mAb binding to 5/3, 19/3, 23/4, and rPfCSP_FL determined through ITC. (FIG. 3E) Affinity (binding events 1 vs. 2; $K_D$, nM) of mAb binding to 5/3, 19/3, 23/4, and rPfCSP_FL determined through ITC. All ITC plots are representative of 2-3 independent experiments; FIGS. 3D-3E reflect an average of these experiments.

(FIG. 4A) Inhibition of P. falciparum invasion of HC-04 hepatocytes (50,000 cells per well; triplicate wells per mAb) by three concentrations of PfCSP mAbs (10, 1.0, and 0.1 μg/mL); data were combined from two independent experiments. Bars represent the mean with standard error of the mean. For each concentration, inhibition mediated by each mAb was compared to VRC01 using a two-way ANOVA with Bonferroni's correction. Dotted line was set at the highest mAb-mediated invasion inhibition at each concentration. (FIG. 4B) Parasite liver burden reduction in mice 40 hrs post-infection (hpi; n=10/group; data pooled from two independent experiments, solid vs. open squares) challenged IV with 2,000 Pb-PfCSP 2 hours after passive transfer of 75 or 25 μg mAb. P values were determined by comparing each mAb to untreated control using the Kruskal-Wallis test with Dunn's correction.

FIGS. 5A-5G. Mechanisms used by human PfCSP mAbs to neutralize SPZ in the liver. (FIG. 5A) Schema for intravital imaging of Pb-PfCSP in the livers of mice (N=3/group) sequentially administered 30 μg Alexa Fluor 405-labeled mAb (blinded), 1 μg rhodamine-labeled dextran, and 100,000 Pb-PfCSP expressing GFP. Observations across the 3 independent experiments/group were combined for analysis (total no. of SPZ observed for each group are indicated). The locations and morphologies of individual Pb-PfCSP were measured; traversal was detected by uptake of dextran into wounded hepatocytes. Representative images depict Pb-PfCSP in the sinusoid, traversing a dextran$^+$ hepatocyte, or invading a dextran$^-$ hepatocyte. (FIG. 5B) Locations of Pb-PfCSP in the liver calculated as the percentage of total parasites observed. (FIG. 5C) Time-lapse images (min:s:ms) of a Pb-PfCSP exiting a sinusoid and traversing a hepatocyte. (FIG. 5D) Percentage of Pb-PfCSP that traversed >1 hepatocyte. (FIG. 5E) Time-lapse images (min:s:ms) of a Pb-PfCSP that underwent dotty death. (FIG. 5F) Quantification of dotty death, measured by counting the number of fragments arising from mAb-bound SPZ. Bars represent the mean; each dot is an individual Pb-PfCSP. P values were determined by comparing each mAb to VRC01 using the Kruskal-Wallis test with Dunn's correction. (FIG. 5G) Locations in which Pb-PfCSP underwent dotty death. P values were determined by comparing all mAbs to each other using the chi-squared test; no significant differences (ns) were observed. Aggregate represents all SPZ combined from every group. In FIGS. 5B and 5D, P values were determined by comparing each mAb to VRC01 using the chi-squared test with Bonferroni's correction. In FIGS. 5C and 5E, arrows and stars respectively indicate anterior and posterior end of SPZ.

(FIG. 6A) Kaplan-Meier survival curves of mice challenged with five infected mosquito bites 3 days after passive transfer of 600, 300, or 100 μg mAb (n indicates number of mice for each mAb group; data were respectively combined from three, five, and three independent blinded experiments). P values were determined by comparing L9 to every other mAb and untreated control using the log-rank test. (FIG. 6B) Mean and 95% confidence intervals (CI) of the percentage of mice infected from FIG. 6A. (FIG. 6C) Serum mAb concentrations in mice from FIG. 6A one day prior to challenge. P values were determined by comparing mAbs to each other using the Kruskal-Wallis test with Dunn's correction. (FIG. 6D) Dose-response analysis of infection probability (percent protected) versus mAb dose (μg) and pre-challenge serum mAb concentrations (μg/mL) for L9, CIS43, 317, and mAb10 estimated by a 2-parameter logistic (2PL) regression model. (FIG. 6E) Dose required for 50% inhibition ($ID_{50}$) and serum concentration required for 50% inhibition ($IC_{50}$) with 95% CI of L9, 317, CIS43, and mAb10 estimated from the dose-response 2PL model in FIG. 6D. (FIG. 6F) Odds ratio (OR) with 95% CI that L9 was more protective than 317, CIS43, and mAb10 at any mAb dose or concentration.

(FIG. 7A)

Binding of varying concentrations of the 28 mAbs L2-L48 to rPfCSP by ELISA, expressed as AUC. VRC01 is an anti-HIV-1 isotype control mAb. (FIG. 7B) Binding of 20 µg/mL mAbs L2-L48 to Pb-PfCSP determined by flow cytometry. The median fluorescence intensity (MFI) of the mAb-bound SPZ is plotted. VRC01 was included as a negative control; CIS43 and L9 were included as positive controls. (FIG. 7C) Reduction of parasite liver burden in mice 40 hrs post-infection (hpi; n=5/group) treated with 300 µg of mAbs L2-L48 2 hours before IV challenge with 2,000 Pb-PfCSP. Significant differences (P values) between each mAb and the untreated control were determined using the Kruskal-Wallis test with Dunn's correction. In FIG. 7B and FIG. 7C, dotted lines separate independent experiments.

(FIG. 9A) Percentage of SPZ that were sinusoid-bound. (FIG. 9B) Percentage of SPZ that productively invaded a hepatocyte. (FIG. 9C) Percentage of SPZ that traversed >1 hepatocyte. (FIG. 9D) Percentage of SPZ that underwent dotty death. (FIG. 9E) Time-lapse images (min:s:ms) of an immobilized, mAb-bound SPZ bursting, leaking GFP, and disappearing. Arrow and star respectively indicate anterior and posterior end of SPZ. In FIGS. 9A-9D, bars represent the mean, each dot represents an independent mouse/experiment, and dotted line was set at the isotype control VRC01.

SEQUENCES

Figure 1A:
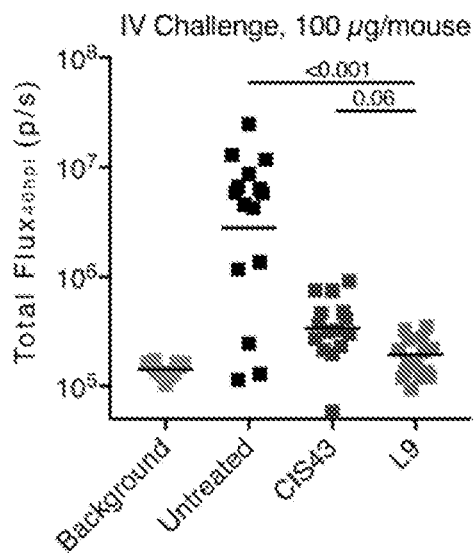
FIGS. 1A-1G. L9 is a neutralizing human mAb that binds the NPNV (SEQ ID NO: 32) motif of PfCSP.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (29.5 KB, created on Oct. 27, 2021), which is incorporated by reference herein. In the accompanying sequence listing:

```
SEQ ID NO: 1 is the amino acid sequence of the L9 V_H.
QVKLVESGGGVVQPGRSLRLSCEASGFIFSTYGMHWVRQAPGKGLEWVAVIWFDGSNIYYADSVKGRFTISRDNSKNTVF

MQMDSLRAEDTAVYYCHRNFYDGSGPFDYWGQGTLVTVSS

SEQ ID NO: 2 is the amino acid sequence of the L9 V_L.
DIQMTQSPSTLSASVGDRVTITCRASQFISRWLAWYQQKPGKAPKLLIYKASSLESGVPSRFSGSGSETHFTLTISSLQP

DDVATYYCQEYTSYGRTFGQGTKVEIK

SEQ ID NOs: 3-8 are CDR sequences.

SEQ ID NO: 9 is the amino acid sequence of an IgG1 heavy chain including the
L9 V_H.
MGWSCIILFLVATATGVHSQVKLVESGGGVVQPGRSLRLSCEASGFIFSTYGMHWVRQAPGKGLEWVAVIWFDGSNIYY

ADSVKGRFTISRDNSKNTVFMQMDSLRAEDTAVYYCHRNFYDGSGPFDYWGQGTLVTVSSASTKGPSVFPLAPSSKSTS

GGTAALGCLVKDYFPEPVTVSWNSGALTSGVHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVF SCSVMHEALHNHYTQKSLSLSPGK

SEQ ID NO: 10 is the amino acid sequence of an IgG1 light chain including the
L9 V_L.
MGWSCIILFLVATATGVHSDIQMTQSPSTLSASVGDRVTITCRASQFISRWLAWYQQKPGKAPKLLIYKASSLESGVPSR

FSGSGSETHFTLTISSLQPDDVATYYCQEYTSYGRTFGQGTKVEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPVTKSFNRGEC

SEQ ID NO: 11 is an exemplary nucleic acid sequence encoding the L9 V_H.
CAGGTGAAGCTGGTGGAGTCTGGGGGAGGCGTGGTCCAGCCTGGGAGGTCCCTGAGACTCTCCTGTGAAGCGTCTGGATT

CATCTTCAGTACCTATGGCATGCACTGGGTCCGCCAGGCTCCAGGCAAGGGGCTGGAGTGGGTGGCAGTTATATGGTTTG

ATGGAAGTAACATATACTATGCAGACTCCGTGAAGGGCCGATTCACCATCTCCAGAGACAATTCCAAGAACACGGTGTTT

ATGCAAATGGACAGCCTGAGAGCCGAGGACACGGCTGTGTATTACTGCCACCGCAATTTTTATGATGGTAGTGGTCCCTT

TGACTATTGGGGCCAGGGAACCCTGGTCACCGTCTCCTCA
```

-continued

SEQ ID NO: 12 is an exemplary nucleic acid sequence optimized for expression in HEK293 cells and encoding the L9 $V_H$.
CAGGTGAAGCTGGTGGAGTCTGGAGGAGGAGTGGTGCAGCCAGGCCGGTCTCTGAGACTGAGCTGCGAGGCCTCCGGCTT

CATCTTTAGCACCTACGGAATGCACTGGGTGCGGCAGGCACCTGGCAAGGGCCTGGAGTGGGTGGCCGTGATCTGGTTCG

ACGGCTCCAACATCTACTATGCCGATTCTGTGAAGGGCAGGTTCACCATCTCTCGCGACAACAGCAAGAATACAGTGTTT

ATGCAGATGGACAGCCTGCGGGCCGAGGATACAGCCGTGTACTATTGTCACAGGAATTTCTACGACGGCTCCGGCCCCTT

TGATTATTGGGGCCAGGGCACCCTGGTGACAGTGAGCTCC

SEQ ID NO: 13 is an exemplary nucleic acid sequence encoding the L9 $V_L$.
GACATCCAGATGACCCAGTCTCCTTCCACCCTGTCTGCATCTGTAGGAGACAGAGTCACCATCACTTGCCGGGCCAGTCA

GTTTATTAGTCGTTGGTTGGCCTGGTATCAGCAGAAACCAGGGAAAGCCCCTAAGCTCCTGATCTATAAGGCGTCTAGTT

TAGAAAGTGGGGTCCCATCAAGGTTCAGCGGCAGTGGATCTGAGACACATTTCACTCTCACCATCAGCAGCCTGCAGCCT

GATGATGTTGCAACTTATTACTGCCAAGAGTACACTAGTTATGGTAGGACGTTCGGCCAAGGGACCAAGGTGGAAATCAA

A

SEQ ID NO: 14 is an exemplary nucleic acid sequence optimized for expression in HEK293 cells and encoding the L9 $V_L$.
GACATCCAGATGACCCAGTCCCCATCTACACTGAGCGCCTCCGTGGGCGATAGGGTGACCATCACATGCAGAGCCTCTCA

GTTCATCAGCAGGTGGCTGGCCTGGTACCAGCAGAAGCCCGGCAAGGCCCCTAAGCTGCTGATCTATAAGGCAAGCTCCC

TGGAGTCCGGAGTGCCATCTCGCTTCTCTGGCAGCGGCTCCGAGACACACTTTACCCTGACAATCTCTAGCCTGCAGCCC

GACGATGTGGCCACCTACTATTGTCAGGAGTACACCTCCTATGGCCGGACATTTGGCCAGGGCACCAAGGTGGAGATCAA

G

SEQ ID NO: 15 is the amino acid sequence of the CIS43 $V_H$.
QVQLVQSGAEVKKPGASVKVSCKASGYTFTSYAIHWVRQAPGQRLEWMGWIKAGNGNTRYSQKFQDRVTITROTSTTTA

YMELSSLRSEDTAVYYCALLTVLTPDDAFDIWGQGTMVTVSS

SEQ ID NO: 16 is the amino acid sequence of the CIS43 $V_L$.
DIVMTQSPDSLAVSLGERATINCKSSQSVLYSSNNKNYLAWYQQKPGQPPNLLIYWASTRQSGVPDRFSGSGSGTDFTL

TISSLQAEDVAVYYCHQYYSSPLTFGGGTKVEIK

SEQ ID NO: 17 is the amino acid sequence of an IgGI heavy chain including the CIS43 $V_H$.
MGWSCIILFLVATATGVHSQVQLVQSGAEVKKPGASVKVSCKASGYTFTSYAIHWVRQAPGQRLEWMGWIKAGNGNTRY

SQKFQDRVTITRDTSTTTAYMELSSLRSEDTAVYYCALLTVLTPDDAFDIWGQGTMVTVSSASTKGPSVFPLAPSSKST

SGGTAALGCLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHNHYTQKSLSLSPGK

SEQ ID NO: 18 is the amino acid sequence of an IgGI light chain including the CIS43 $V_L$.
MGWSCIILFLVATATGVHSDIVMTQSPDSLAVSLGERATINCKSSQSVLYSSNNKNYLAWYQQKPGQPPNLLIYWASTR

QSGVPDRFSGSGSGTDFTLTISSLQAEDVAVYYCHQYYSSPLTFGGGTKVEIKRTVAAPSVFIFPPSDEQLKSGTASVV

CLLNNFYPREAKVQWKVDNALQSGNSQESVTEQDSKDSTYSLSSTLTLSKADYEKHKVYACEVTHQGLSSPVTKSFNRG

EC

SEQ ID NOs: 19-27 are peptide sequences.

SEQ ID NO: 19: PADGNPDPNANPNVD (peptide 20)

SEQ ID NO: 20: NPDPNANPNVDPNAN (peptide 21)

SEQ ID NO: 21: NANPNVDPNANPNVD (peptide 22)

SEQ ID NO: 22: NVDPNANPNVDPNAN (peptide 23)

SEQ ID NO: 23: NVDPNANPNANPNAN (peptide 27)

-continued

SEQ ID NO: 24: NANPNANPNANPNAN (peptide 29)

SEQ ID NO: 25: NANPNANPNVDPNAN (peptide 43)

SEQ ID NO: 26: NANPNVDPNANPNAN (peptide 44)

SEQ ID NO: 27: NANPNANPNANPNKN (peptide 61)

SEQ ID NO: 28 is an exemplary amino acid sequence for PfCSP (GenBank Acc. No.
CAB38998.2, incorporated by reference herein)
MMRKLAILSVSSFLFVEALFQEYQCYGSSSNTRVLNELNYDNAGTNLYNELEMNYYGKQENWYSLKKNSRSLGENDDGN

NEDNEKLRKPKHKKLKQPADGNPDPNANPNVDPNANPNVDPNANPNVDPNANPNANPNANPNANPNANPNANPNANPNA

NPNANPNANPNANPNANPNANPNANPNANPNANPNANPNVDPNANPNANPNANPNANPNANPNANPNANPNANPNANPN

ANPNANPNANPNANPNANPNANPNANPNANPNANPNKNNQGNGQGHNMPNDPNRNVDENANANSAVKNNNNEEPSDKHI

KEYLNKIQNSLSTEWSPCSVTCGNGIQVRIKPGSANKPKDELDYANDIEKKICKMEKCSSVFNVVNSSIGLIMVLSFLF

LN

SEQ ID NOs: 29-32 are sequences from the repeat region of PfCSP
SEQ ID NO: 29: NPDP

SEQ ID NO: 30: NVDP

SEQ ID NO: 31: NANP

SEQ ID NO: 32: NPNV

SEQ ID NO: 33 is a signal peptide sequence.
MDSKGSSQKGSRLLLLLVVSNLLLPQGVLA

SEQ ID NOs: 34-42 are peptide sequences.
SEQ ID NO: 34: NANPNANPNANPNANPNANPNANPNANPNANPNANP

SEQ ID NO: 35: NANPNANPNANP

SEQ ID NO: 36: NANPNANP

SEQ ID NO: 37: DPNA

SEQ ID NO: 38: NPNA

SEQ ID NO: 39: NVDPNANP

SEQ ID NO: 40: PESSSNPDCNANPNVDPNEDLIKKCEKINVPTEEIKKEIEEKK

SEQ ID NO: 41: NANPNANPNANPNANP

SEQ ID NO: 42: NANPNANPNANPNANPNANPNANP

DETAILED DESCRIPTION

Malaria is a mosquito-borne parasitic disease causing high morbidity and mortality, primarily in infants and young children in sub-Saharan Africa. Development of a highly effective vaccine or antibodies that can prevent and ultimately eliminate malaria is urgently needed. This disclosure provides monoclonal antibodies and antigen binding fragments directed against PfCSP. Data in the examples show that passive transfer of the L9 monoclonal antibody confers high-level, sterile protection in an animal model. L9 is more potent for inhibiting malaria infection than prior human antibodies against PfCSP. This is a particularly surprising result, given that L9 targets an epitope that is present in the repeat regions of PfCSP at a much lower frequency than the corresponding preferred epitopes of other antibodies that bind this region of PfCSP. L9 preferentially binds with high affinity to the "NPNV" (SEQ ID NO: 32) epitope that occurs when an NANP (SEQ ID NO: 31) repeat is followed by an NVDP (SEQ ID NO: 30) minor repeat, with relatively poor affinity for the immunodominant NANP (SEQ ID NO: 31) repeats of PfCSP. Thus, the PfCSP-specific antibodies and antigen binding fragments provided herein, including L9, are effective for passive prevention of malaria for use in suitable subjects, such as travelers, military personnel, and subjects in elimination campaigns.

I. SUMMARY OF TERMS

Unless otherwise noted, technical terms are used according to conventional usage. Definitions of many common terms in molecular biology may be found in Krebs et al. (eds.), *Lewin's genes XII*, published by Jones & Bartlett Learning, 2017. As used herein, the singular forms "a," "an," and "the," refer to both the singular as well as plural, unless the context clearly indicates otherwise. For example, the term "an antigen" includes singular or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

About: Unless context indicated otherwise, "about" refers to plus or minus 5% of a reference value. For example, "about" 100 refers to 95 to 105.

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody and Antigen Binding Fragment: An immunoglobulin, antigen-binding fragment, or derivative thereof, that specifically binds and recognizes an analyte (antigen) such as PfCSP. The term "antibody" is used herein in the broadest sense and encompasses various antibody structures, including but not limited to monoclonal antibodies, polyclonal antibodies, multispecific antibodies (e.g., bispecific antibodies), and antigen binding fragments, so long as they exhibit the desired antigen-binding activity.

Non-limiting examples of antibodies include, for example, intact immunoglobulins and variants and fragments thereof that retain binding affinity for the antigen. Examples of antigen binding fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Eds.), *Antibody Engineering*, Vols. 1-2, 2$^{nd}$ ed., Springer-Verlag, 2010).

Antibodies also include genetically engineered forms such as chimeric antibodies (such as humanized murine antibodies) and heteroconjugate antibodies (such as bispecific antibodies).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain). In combination, the heavy and the light chain variable regions specifically bind the antigen.

References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, 5$^{th}$ ed., NIH Publication No. 91-3242, Public Health Service, National Institutes of Health, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. (*Sequences of Proteins of Immunological Interest*, 5$^{th}$ ed., NIH Publication No. 91-3242, Public Health Service, National Institutes of Health, U.S. Department of Health and Human Services, 1991; "Kabat" numbering scheme), Al-Lazikani et al., ("Standard conformations for the canonical structures of immunoglobulins," *J. Mol. Bio.*, 273(4):927-948, 1997; "Chothia" numbering scheme), and Lefranc et al. ("IMGT unique numbering for immunoglobulin and T cell receptor variable domains and Ig superfamily V-like domains," *Dev. Comp. Immunol.*, 27(1):55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

In some embodiments, a disclosed antibody includes a heterologous constant domain. For example, the antibody includes a constant domain that is different from a native constant domain, such as a constant domain including one or more modifications (such as the "LS" mutations) to increase half-life.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Greenfield (Ed.), *Antibodies: A Laboratory Manual*, 2$^{nd}$ ed. New York: Cold Spring Harbor Laboratory Press, 2014.)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel*. 1$^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

Antibody or antigen binding fragment that neutralizes *P. falciparum*: An antibody or antigen binding fragment that specifically binds to a *P. falciparum* antigen (such as CSP) in such a way as to inhibit a biological function associated with *P. falciparum* that inhibits *P. falciparum* infection. The antibody can neutralize the activity of *P. falciparum* at various points during the lifecycle of the pathogen. For example, an antibody or antigen binding fragment that neutralizes *P. falciparum* may interfere with the pathogen by binding it in the skin and limiting entry into the blood or entry into the hepatocytes in the liver by interfering with the interaction of the pathogen and one or more cell surface receptors. Alternately, an antibody may interfere with one or more post-attachment interactions of the pathogen with its receptors, for example, by interfering with pathogen internalization by receptor-mediated endocytosis.

In some embodiments, an antibody or antigen binding fragment that specifically binds to PfCSP and neutralizes *P. falciparum* inhibits sporozoite invasion of hepatocytes, for example, by at least 50% (such as at least 60%, at least 70%, at least 80%, at least 90%, or more) compared to a control antibody or antigen binding fragment. In some embodiments, an antibody or antigen binding fragment that specifically binds to PfCSP and neutralizes *P. falciparum* inhibits infection of a human subject by *P. falciparum*, for example, by at least 50% compared to a control antibody or antigen binding fragment.

Biological sample: A sample obtained from a subject. Biological samples include all clinical samples useful for detection of disease or infection (for example, *P. falciparum* infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a *P. falciparum* infection.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody can include one or more constant domains, but does not necessarily include a constant domain.

Circumsporozoite protein (CSP): The circumsporozoite protein (CSP) is a major malaria parasite surface protein during the sporogonic cycle. CSP covers the surface of *P. falciparum* sporozoites, which are transmitted from the mosquito salivary gland to host hepatocytes. An exemplary PfCSP amino acid sequence is provided as SEQ ID NO: 28.

CIS43 Antibody: A monoclonal antibody that specifically binds to an epitope on PfCSP and neutralizes malaria infection. The CIS43 antibody and methods for its production are described, for example, in PCT Pub. No. WO 2018/148660, which is incorporated by reference herein in its entirety. The amino acid sequences of the heavy and light variable regions of the CIS43 antibody are provided herein as SEQ ID NOs: 15 and 16.

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Greenfield (Ed.), *Antibodies: A Laboratory Manual*, 2$^{nd}$ ed. New York: Cold Spring Harbor Laboratory Press, 2014, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods, for instance immunohistochemistry (IHC), immunoprecipitation (IP), flow cytometry, immunofluorescence microscopy, ELISA, immunoblotting (for example, Western blot), magnetic resonance imaging (MRI), computed tomography (CT) scans, radiography, and affinity chromatography.

Conjugate: A complex of two molecules linked together, for example, linked together by a covalent bond. In one embodiment, an antibody is linked to an effector molecule; for example, an antibody that specifically binds to CSP from *P. falciparum* covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, a CSP-specific antibody can include up to 1, 2, 3, 4, 5, 6, 7, 8, 9, or up to 10 conservative substitutions compared to a reference antibody sequence and retain specific binding activity for CSP, and/or *P. falciparum* neutralization activity. The term conservative variation also includes the use of a substituted amino acid in place of an unsubstituted parent amino acid.

Individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the CSP specific antibody, such as the ability to specifically bind to CSP or neutralize *P. falciparum*. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient not infected with *P. falciparum*. In other embodiments, the control is a positive control, such as a tissue sample obtained from a patient diagnosed with *P. falciparum* infection. In still other embodiments, the control is a historical control or standard reference value or range of values (such as a previously tested control sample, such as a group of *P. falciparum* patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Green and Sambrook (*Molecular Cloning: A Laboratory Manual*, $4^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Detecting: To identify the existence, presence, or fact of something.

Effective amount: A quantity of a specific substance sufficient to achieve a desired effect in a subject to whom the substance is administered. For instance, this can be the amount necessary to inhibit a *P. falciparum* infection, such as the amount necessary to inhibit or prevent *P. falciparum* sporozoites from invading the liver in the subject or to measurably alter outward symptoms of the *P. falciparum* infection.

In some embodiments, administration of an effective amount of a disclosed antibody or antigen binding fragment that binds to PfCSP can reduce or inhibit a *P. falciparum* infection (for example, as measured by infection of cells, or by number or percentage of subjects infected by the *P. falciparum*, or by an increase in the survival time of infected subjects, or reduction in symptoms associated with *P. falciparum* infection) by a desired amount, for example by at least 10%, at least 20%, at least 50%, at least 60%, at least 70%, at least 80%, at least 90%, at least 95%, at least 98%, or even at least 100% (elimination or prevention of detectable *P. falciparum* infection), as compared to a suitable control.

The effective amount of an antibody or antigen binding fragment that specifically binds PfCSP that is administered to a subject to inhibit *P. falciparum* infection will vary depending upon a number of factors associated with that subject, for example the overall health and/or weight of the subject. An effective amount can be determined by varying the dosage and measuring the resulting response, such as, for example, a reduction in pathogen titer. Effective amounts also can be determined through various in vitro, in vivo or in situ immunoassays.

An effective amount encompasses a fractional dose that contributes in combination with previous or subsequent administrations to attaining an effective response. For example, an effective amount of an agent can be administered in a single dose, or in several doses, for example daily, during a course of treatment lasting several days or weeks. However, the effective amount can depend on the subject being treated, the severity and type of the condition being treated, and the manner of administration. A unit dosage form of the agent can be packaged in an amount, or in multiples of the effective amount, for example, in a vial (e.g., with a pierceable lid) or syringe having sterile components.

Effector molecule: A molecule intended to have or produce a desired effect; for example, a desired effect on a cell to which the effector molecule is targeted. Effector molecules can include, for example, polypeptides and small molecules. In one non-limiting example, the effector molecule is a toxin. Some effector molecules may have or produce more than one desired effect.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on CSP from P. falciparum.

Expression: Transcription or translation of a nucleic acid sequence. For example, an encoding nucleic acid sequence (such as a gene) can be expressed when its DNA is transcribed into RNA or an RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcriptional terminators, a start codon (ATG) in front of a protein-encoding gene, splice signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Non-limiting examples of expression vectors include cosmids, plasmids (e.g., naked or contained in liposomes) and viruses (e.g., lentiviruses, retroviruses, adenoviruses, and adeno-associated viruses) that incorporate the recombinant polynucleotide.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Fc region: The constant region of an antibody excluding the first heavy chain constant domain. Fc region generally refers to the last two heavy chain constant domains of IgA, IgD, and IgG, and the last three heavy chain constant domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region is typically understood to include immunoglobulin domains Cγ2 and Cγ3 and optionally the lower part of the hinge between Cγ1 and Cγ2. Although the boundaries of the Fc region may vary, the human IgG heavy chain Fc region is usually defined to include residues following C226 or P230 to the Fc carboxyl-terminus, wherein the numbering is according to Kabat. For IgA, the Fc region includes immunoglobulin domains Cα2 and Cα3 and optionally the lower part of the hinge between Cα1 and Cα2.

Host cell: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

IgA: A polypeptide belonging to the class of antibodies that are substantially encoded by a recognized immunoglobulin alpha gene. In humans, this class or isotype comprises $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$.

Immune complex: The binding of antibody or antigen binding fragment (such as a scFv) to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Inhibiting a disease or condition: Reducing the full development of a disease or condition in a subject, for example, reducing the full development of a *P. falciparum* infection in a subject who is at risk of a *P. falciparum* infection. This includes neutralizing, antagonizing, prohibiting, preventing, restraining, slowing, disrupting, stopping, or reversing progression or severity of the disease or condition.

Inhibiting a disease or condition refers to a prophylactic intervention administered before the disease or condition has begun to develop (for example a treatment initiated in a subject at risk of *P. falciparum* infection, but not infected by *P. falciparum*) that reduces subsequent development of the disease or condition and/or ameliorates a sign or symptom of the disease or condition following development. The term "ameliorating," with reference to inhibiting a disease or condition refers to any observable beneficial effect of the prophylactic intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters that are specific to the particular disease or condition.

In some embodiments, the disclosed CSP-specific antibodies and antigen binding fragments inhibit the invasion of *Plasmodium falciparum* sporozoites into human liver cells (hepatocytes). As mentioned above, the invasion of liver cells is a key event in the infection of a subject with the malaria parasite. Inhibition of the invasion of human liver cells can be measured by one or more of several standard assays (see, for example, Example 1). For example, the disclosed CSP-specific antibodies and antigen binding fragments can inhibit the invasion of *Plasmodium falciparum* sporozoites into human liver cells by at least 20%, at least 30%, at least 40%, or at least 50%, compared to a suitable control.

In some embodiments, the disclosed CSP-specific antibodies and antigen binding fragments inhibit the growth of *Plasmodium falciparum* in a subject, for example, the antibodies and antigen binding fragments inhibit the multiplication of *Plasmodium falciparum* in the subject, resulting in a reduction in pathogen load in the subject compared to a relevant control. For example, the disclosed CSP-specific antibodies and antigen binding fragments can inhibit the growth of *Plasmodium falciparum* in a subject by at least 20%, at least 30%, at least 40%, or at least 50%, compared to a suitable control.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Kabat position: A position of a residue in an amino acid sequence that follows the numbering convention delineated by Kabat et al. (*Sequences of Proteins of Immunological Interest*, 5$^{th}$ Edition, Department of Health and Human Services, Public Health Service, National Institutes of Health, Bethesda, NIH Publication No. 91-3242, 1991).

Linker: A bi-functional molecule that can be used to link two molecules into one contiguous molecule, for example, to link an effector molecule to an antibody. Non-limiting examples of peptide linkers include glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. The linkage can be either by chemical or recombinant means. "Chemical means" refers to a reaction between the antibody moiety and the effector molecule such that there is a covalent bond formed between the two molecules to form one molecule.

Malaria: Malaria is a parasitic infection of humans by the *Plasmodium* species *P. falciparum, P. vivax, P. ovale, P. malariae*, and *P. knowlesi*. Humans become infected following the bite of an infected mosquito, the host of the malarial parasite. Malaria rarely occurs in humans following a blood transfusion or subsequent to needle-sharing. Clinical manifestations of malarial infection which may occur include blackwater fever, cerebral malaria, respiratory failure, hepatic necrosis, occlusion of myocardial capillaries and death.

Infection begins when malaria sporozoites gain access to or are directly injected into the bloodstream of a host by a mosquito. After injection, they migrate to the liver and multiply in hepatocytes for one week. The sporozoites substantially expand in the liver and differentiate to merozoites which are released from the liver into the blood stream, where they infect erythrocytes. When the merozoite matures in the red blood cell, it is known as a trophozoite and, when fully developed, as a schizont. A schizont is the stage when nuclear division occurs to form individual merozoites which are released to invade other red cells. Malaria clinical symptoms appear during the blood-stage. After several schizogonic cycles, some parasites, instead of becoming schizonts through asexual reproduction, develop into large uninucleate parasites, known as gametocytes. These gametocytes are the sexual blood cell stage forms of the parasite.

Sexual development of the malaria parasites involves the female macrogametocyte and the male microgametocyte. If a mosquito feeds on the blood of an infected host, it can ingest gametocytes within the blood. Fertilization and sexual recombination of the parasite occurs in the mosquito's gut. The fertilized parasite, which is known as a zygote, then develops into an ookinete. The ookinete penetrates the midgut wall of the mosquito and develops into an oocyst, within which many small sporozoites form. When the oocyst ruptures, the sporozoites migrate to the salivary gland of the mosquito via the hemolymph. Once in the saliva of the mosquito, the parasite can be injected into a host, repeating the life cycle.

Nucleic acid (molecule or sequence): A deoxyribonucleotide or ribonucleotide polymer or combination thereof including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides.

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy*, 22$^{nd}$ ed., London, UK: Pharmaceutical Press, 2013, describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as non-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences. Homologs and variants of a $V_L$ or a $V_H$ of an antibody that specifically binds a target antigen are typically characterized by possession of at least about 75% sequence identity, for example at least about 80%, 85%, 90%, 91%, 92%, 93%, 94%, 95%, 96%, 97%, 98% or 99% sequence identity counted over the full-length alignment with the amino acid sequence of interest.

Any suitable method may be used to align sequences for comparison. Non-limiting examples of programs and alignment algorithms are described in: Smith and Waterman, *Adv. Appl. Math.* 2(4):482-489, 1981; Needleman and Wunsch, *J. Mol. Biol.* 48(3):443-453, 1970; Pearson and Lipman, *Proc. Natl. Acad. Sci. U.S.A.* 85(8):2444-2448, 1988; Higgins and Sharp, *Gene,* 73(1):237-244, 1988; Higgins and Sharp, *Bioinformatics,* 5(2):151-3, 1989; Corpet, *Nucleic Acids Res.* 16(22):10881-10890, 1988; Huang et al. *Bioinformatics,* 8(2):155-165, 1992; and Pearson, *Methods Mol. Biol.* 24:307-331, 1994. Altschul et al., *J. Mol. Biol.* 215(3):403-410, 1990, presents a detailed consideration of sequence alignment methods and homology calculations. The NCBI Basic Local Alignment Search Tool (BLAST) (Altschul et al., *J. Mol. Biol.* 215(3):403-410, 1990) is available from several sources, including the National Center for Biological Information and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Generally, once two sequences are aligned, the number of matches is determined by counting the number of positions where an identical nucleotide or amino acid residue is present in both sequences. The percent sequence identity between the two sequences is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

Specifically bind: When referring to an antibody or antigen binding fragment, refers to a binding reaction which determines the presence of a target protein in the presence of a heterogeneous population of proteins and other biologics. Thus, under designated conditions, an antibody binds preferentially to a particular target protein, peptide or polysaccharide (such as an antigen present on the surface of a pathogen, for example PfCSP) and does not bind in a significant amount to other proteins present in the sample or subject. Specific binding can be determined by standard methods. See Harlow & Lane, *Antibodies, A Laboratory Manual*, $2^{nd}$ ed., Cold Spring Harbor Publications, New York (2013), for a description of immunoassay formats and conditions that can be used to determine specific immunoreactivity.

With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar. $K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

An antibody that specifically binds to an epitope on PfCSP is an antibody that binds substantially to PfCSP, including cells or tissue expressing PfCSP, substrate to which the PfCSP is attached, or PfCSP in a biological specimen. It is, of course, recognized that a certain degree of non-specific interaction may occur between an antibody and a non-target (such as a cell that does not express PfCSP). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein.

Subject: Living multi-cellular vertebrate organisms, a category that includes human and non-human mammals. In an example, a subject is a human. In an additional example, a subject is selected that is in need of inhibiting a *P. falciparum* infection. For example, the subject is uninfected and at risk of *P. falciparum* infection.

Transformed: A transformed cell is a cell into which a nucleic acid molecule has been introduced by molecular biology techniques. As used herein, the term transformed and the like (e.g., transformation, transfection, transduction, etc.) encompasses all techniques by which a nucleic acid molecule might be introduced into such a cell, including transduction with viral vectors, transformation with plasmid vectors, and introduction of DNA by electroporation, lipofection, and particle gun acceleration.

Vector: An entity containing a nucleic acid molecule (such as a DNA or RNA molecule) bearing a promoter(s) that is operationally linked to the coding sequence of a protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements. Viral vectors are recombinant nucleic acid vectors having at least some nucleic acid sequences derived from one or more viruses. In some embodiments, a viral vector comprises a nucleic acid molecule encoding a disclosed antibody or antigen binding fragment that specifically binds to PfCSP and neutralizes *P. falciparum*. In some embodiments, the viral vector can be an adeno-associated virus (AAV) vector.

II. DESCRIPTION OF SEVERAL EMBODIMENTS

A. Neutralizing Monoclonal Antibodies to CSP and Antigen Binding Fragments Thereof Isolated monoclonal antibodies and antigen binding fragments that specifically bind an epitope on PfCSP are provided. The antibodies and antigen binding fragments can be fully human. The antibodies and antigen binding fragments can neutralize *P. falciparum*, for example the disclosed antibodies can inhibit *P. falciparum* sporozoite infection of hepatocytes in vitro and *P. falciparum* sporozoite invasion of liver in vivo. Also disclosed herein are compositions comprising the antibodies and antigen binding fragments and a pharmaceutically acceptable carrier. Nucleic acids encoding the antibodies or antigen binding fragments, expression vectors (such as DNA and RNA vectors for expression and delivery, as well as adeno-associated virus (AAV) viral vectors) comprising these nucleic acids are also provided. The antibodies, antigen binding fragments, nucleic acid molecules, host cells, and compositions can be used for research, diagnostic and prophylactic purposes. For example, the disclosed antibodies and antigen binding fragments can be used to diagnose a subject with a *P. falciparum* infection, or can be administered prophylactically to inhibit *P. falciparum* infection in a subject.

The discussion of monoclonal antibodies below refers to isolated monoclonal antibodies that include heavy and/or light chain variable domains (or antigen binding fragments thereof) comprising a CDR1, CDR2, and/or CDR3 with reference to the kabat numbering scheme (unless the context indicates otherwise). Various CDR numbering schemes (such as the Kabat, Chothia or IMGT numbering schemes) can be used to determine CDR positions. The amino acid sequence and the CDR positions of the heavy and light chain of the L9 monoclonal antibody according to the IMGT numbering scheme are shown in Table 1.

TABLE 1

IMGT CDR sequences of CSP specific antibodies

L9 $V_H$

| VH | SEQ ID NO: 1 residues | A.A. Sequence | CDR SEQ ID NO |
|---|---|---|---|
| HCDR1 | 26-33 | GFIFSTYG | 3 |
| HCDR2 | 51-58 | IWFDGSNI | 4 |
| HCDR3 | 97-109 | HRNFYDGSGPFDY | 5 |

L9 $V_L$

| VL | SEQ ID NO: 2 residues | A.A. Sequence | CDR SEQ ID NO |
|---|---|---|---|
| LCDR1 | 27-32 | QFISRW | 6 |
| LCDR2 | 50-52 | KAS | 7 |
| LCDR3 | 89-97 | QEYTSYGRT | 8 |

In some embodiments, the antibody or antigen binding fragment is based on or derived from the L9 antibody, and specifically binds to PfCSP and neutralizes P. falciparum. For example, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT or kabat), of the L9 antibody, and specifically binds to PfCSP and neutralizes P. falciparum.

In some embodiments, the antibody or antigen binding fragment comprises a $V_H$ comprising the HCDR1, the HCDR2, and the HCDR3 of the L9 $V_H$ as set forth in Table 1, and specifically binds to PfCSP and neutralizes P. falciparum. In some embodiments, the antibody or antigen binding fragment comprises a $V_L$ comprising the LCDR1, the LCDR2, and the LCDR3 of the L9 $V_L$ as set forth in Table 1, and specifically binds to PfCSP and neutralizes P. falciparum. In some embodiments, the antibody or antigen binding fragment comprises a $V_H$ and a $V_L$ comprising the HCDR1, the HCDR2, the HCDR3, the LCDR1, the LCDR2, and the LCDR3 of the L9 $V_H$ and $V_L$ as set forth in Table 1, and specifically binds to PfCSP and neutralizes P. falciparum.

In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 1, and specifically binds to PfCSP and neutralizes P. falciparum. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 2, and specifically binds to PfCSP and neutralizes P. falciparum. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 1 and 2, respectively, and specifically binds to PfCSP and neutralizes P. falciparum.

In some embodiments, the antibody or antigen binding fragment comprises a $V_H$ comprising a HCDR1, a HCDR2, and a HCDR3 as set forth as SEQ ID NOs: 3, 4, and 5, respectively, and a $V_L$ comprising a LCDR1, a LCDR2, and a LCDR3 as set forth as SEQ ID NOs: 6, 7, and 8, respectively, and specifically binds to PfCSP and neutralizes P. falciparum.

In some embodiments, the antibody or antigen binding fragment comprises a $V_H$ comprising a HCDR1, a HCDR2, and a HCDR3 as set forth as SEQ ID NOs: 3, 4, and 5, respectively, a $V_L$ comprising a LCDR1, a LCDR2, and a LCDR3 as set forth as SEQ ID NOs: 6, 7, and 8, respectively, wherein the $V_H$ comprises an amino acid sequence at least 90% identical to SEQ ID NO: 1, the $V_L$ comprises an amino acid sequence at least 90% identical to SEQ ID NO: 2, and the antibody or antigens binding fragment specifically binds to PfCSP and neutralizes P. falciparum.

In additional embodiments, the antibody or antigen binding fragment comprises a $V_H$ comprising the amino acid sequence set forth as SEQ ID NO: 1, and specifically binds to PfCSP and neutralizes P. falciparum. In more embodiments, the antibody or antigen binding fragment comprises a $V_L$ comprising the amino acid sequence set forth as SEQ ID NO: 2, and specifically binds to PfCSP and neutralizes P. falciparum. In some embodiments, the antibody or antigen binding fragment comprises a $V_H$ and a $V_L$ comprising the amino acid sequences set forth as SEQ ID NOs: 1 and 2, respectively, and specifically binds to PfCSP and neutralizes P. falciparum.

Additional Antibodies that Bind to the L9 Epitope on PfCSP

In additional embodiments, isolated monoclonal antibodies and antigen binding fragments thereof that specifically bind to the L9 epitope on PfCSP are provided. Epitope mapping and structural studies provided herein allow for detailed analysis of the binding of L9 to PfCSP, definition of the L9 epitope on PfCSP, and an understanding of the structure required of an antibody to bind to the L9 epitope on PfCSP and provide the unexpectedly superior P. falciparum neutralization of L9.

As discussed in the Examples, the L9 antibody specifically binds to a "NPNV" (SEQ ID NO: 32) epitope on PfCSP, and binding to this particular epitope correlated with the unexpectedly superior neutralization capacity of L9. The epitope sequence is found twice in in peptide 22 (NANPNVDPNANPNVD, SEQ ID NO: 21), to which L9 binds with an apparent $K_D$ of less than 1 nM. As discussed in the examples, unlike prior antibodies targeting the PfCSP repeat region, L9 specifically binds to peptide 22 with a much higher affinity than other regions of the repeat sequence, such as peptide 21 (NPDPNANPNVDPNAN, SEQ ID NO: 20). Accordingly, in some embodiments, an antibody or antigen binding fragment is provided that specifically binds to an epitope on PfCSP having the sequence of peptide 22 (SEQ ID NO: 21) with a KD at least 5-fold (such as at least 10-fold) lower than that of binding to peptide 21 ((NPDPNANPNVDPNAN, SEQ ID NO: 20).

In some embodiments, an antibody or antigen binding fragment is provided that specifically binds to an epitope on PfCSP consisting of the amino acid sequence set forth as NANPNVDPNANPNVD (SEQ ID NO: 21). In several embodiments, the antibody or antigen binding fragment specifically binds to the epitope on PfCSP consisting of the amino acid sequence set forth as NANPNVDPNANPNVD (SEQ ID NO: 21) with a $K_D$ of less than 1 nM as determined by biolayer inferometry.

In some examples, antibodies that bind to the L9 epitope can be identified based on their ability to cross-compete (for example, to competitively inhibit the binding of, in a statistically significant manner) with the L9 antibody provided herein in PfCSP binding assays and/or Peptide 22 binding assay (such as those described in the Examples). An antibody "competes" for binding when the competing antibody inhibits PfCSP or Peptide 22 binding of the L9 antibody by more than 50% when the competing antibody and L9 are at equimolar concentrations. In some embodiments, the antibody that binds to the same epitope on PfCSP as the L9 antibody is a human monoclonal antibody. Such human monoclonal antibodies can be prepared and isolated, for example, as described herein.

Human antibodies that bind to the same epitope on PfCSP to which the L9 antibody binds can be produced using any suitable method. Such antibodies may be prepared, for example, by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies that bind to the same epitope on PfCSP to which the L9 antibody binds can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4): 265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3): 185-91 (2005). Human antibodies may also be generated by isolating Fv clone variable domain sequences selected from human-derived phage display libraries. Such variable domain sequences may then be combined with a desired human constant domain.

Antibodies and antigen binding fragments that specifically bind to the same epitope on PfCSP to which the L9 antibody binds can also be isolated by screening combinatorial libraries for antibodies with the desired binding characteristics. For example, by generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

1. Additional Description of Antibodies and Antigen Binding Fragments

The antibody or antigen binding fragment can be a human antibody or fragment thereof. Chimeric antibodies are also provided. The antibody or antigen binding fragment can include any suitable framework region, such as (but not limited to) a human framework region. Alternatively, a heterologous framework region, such as, but not limited to a mouse or monkey framework region, can be included in the heavy or light chain of the antibodies.

The antibody can be of any isotype. The antibody can be, for example, an IgM or an IgG antibody, such as $IgG_1$, $IgG_2$, $IgG_3$, or $IgG_4$. The class of an antibody that specifically binds PfCSP can be switched with another. In one aspect, a nucleic acid molecule encoding $V_L$ or $V_H$ is isolated such that it does not include any nucleic acid sequences encoding the constant region of the light or heavy chain, respectively. A nucleic acid molecule encoding $V_L$ or $V_H$ is then operatively linked to a nucleic acid sequence encoding a $C_L$ or $C_H$ from a different class of immunoglobulin molecule. This can be achieved, for example, using a vector or nucleic acid molecule that comprises a $C_L$ or $C_H$ chain. For example, an antibody that specifically binds PfCSP, that was originally IgG may be class switched to an IgM. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

The antibody or antigen binding fragment can be derivatized or linked to another molecule (such as another peptide or protein). In general, the antibody or antigen binding fragment is derivatized such that the binding to *P. falciparum* is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

(a) Binding Affinity

In several embodiments, the antibody or antigen binding fragment specifically binds PfCSP with an affinity (e.g., measured by $K_D$) of no more than $1.0 \times 10^{-8}$ M, no more than $5.0 \times 10^{-8}$ M, no more than $1.0 \times 10^{-9}$ M, no more than $5.0 \times 10^{-9}$ M, no more than $1.0 \times 10^{-10}$ M, no more than $5.0 \times 10^{-10}$ M, or no more than $1.0 \times 10^{-11}$ M. $K_D$ can be measured, for example, by a radiolabeled antigen binding assay (RIA) performed with the Fab version of an antibody of interest and its antigen. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293(4):865-881, 1999). To establish conditions for the assay, MICROTI-TER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc™ Catalog #269620), 100 µM or 26 pM [$^{125}$I]-antigen are mixed with serial dilutions of a Fab of interest (e.g., consistent with assessment of the anti-VEGF antibody, Fab-12, in Presta et al., *Cancer Res.* 57(20):4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MicroScint™-20; PerkinEmler) is added, and the plates are counted on a TOP-COUNT™ gamma counter (PerkinEmler) for ten minutes. Concentrations of each Fab that give less than or equal to 20% of maximal binding are chosen for use in competitive binding assays.

In another assay, $K_D$ can be measured using surface plasmon resonance assays using a BIACORE®-2000 or a BIACORE®-3000 (BlAcore, Inc., Piscataway, N.J.) at 25° C. with immobilized antigen CM5 chips at ~10 response units (RU). Briefly, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999). If the on-rate exceeds $10^6 M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

(b) Multispecific Antibodies

In some embodiments, a multi-specific antibody, such as a bi-specific antibody, is provided that comprises an antibody or antigen binding fragment as provided herein, such as the L9 antibody or a antigen binding fragment thereof. Any suitable method can be used to design and produce the multi-specific antibody, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Non-limiting examples of suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate).

The multi-specific antibody may have any suitable format that allows for antigen binding by the antibody or antigen binding fragment as provided herein, such as the L9 antibody or an antigen binding fragment thereof. Bispecific single chain antibodies can be encoded by a single nucleic acid molecule. Non-limiting examples of bispecific single chain antibodies, as well as methods of constructing such antibodies are provided in U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538. Additional examples of bispecific single chain antibodies can be found in PCT application No. WO 99/54440; Mack et al., *J. Immunol.*, 158(8):3965-3970, 1997; Mack et al., *Proc. Natl. Acad. Sci. U.S.A.*, 92(15): 7021-7025, 1995; Kufer et al., *Cancer Immunol. Immunother.*, 45(3-4):193-197, 1997; Löffler et al., *Blood,* 95(6): 2098-2103, 2000; and Brühl et al., *J. Immunol.*, 166(4): 2420-2426, 2001. Production of bispecific Fab-scFv ("bibody") molecules are described, for example, in Schoonjans et al. (*J. Immunol.*, 165(12):7050-7057, 2000) and Willems et al. (*J. Chromatogr. B Analyt. Technol. Biomed Life Sci.* 786(1-2):161-176, 2003). For bibodies, a scFv molecule can be fused to one of the VL-CL (L) or VH-CH1 chains, e.g., to produce a bibody one scFv is fused to the C-term of a Fab chain.

(c) Fragments

Antigen binding fragments are encompassed by the present disclosure, such as Fab, F(ab')$_2$, and Fv which include a heavy chain and $V_L$ and specifically bind PfCSP. These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the $V_L$ and $V_L$ expressed as two chains; and (5) Single chain antibody (such as scFv), defined as a genetically engineered molecule containing the $V_H$ and the $V_L$ linked by a suitable polypeptide linker as a genetically fused single chain molecule (see, e.g., Ahmad et al., *Clin. Dev. Immunol.*, 2012, doi:10.1155/2012/980250; Marbry and Snavely, *IDrugs*, 13(8):543-549, 2010). The intramolecular orientation of the $V_H$-domain and the $V_L$-domain in a scFv, is not decisive for the provided antibodies (e.g., for the provided multi-specific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "miniantibody."

Any suitable method of producing the above-discussed antinge binding fragments may be used. Non-limiting examples are provided in Harlow and Lane, *Antibodies: A Laboratory Manual*, 2$^{nd}$, Cold Spring Harbor Laboratory, New York, 2013.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

(d) Variants

In some embodiments, amino acid sequence variants of the antibodies provided herein (such as L9) are provided. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, decreased immunogenicity, or improved ADCC or CDC.

The variants typically retain amino acid residues necessary for correct folding and stabilizing between the $V_H$ and the $V_L$ regions, and will retain the charge characteristics of the residues in order to preserve the low pI and low toxicity of the molecules Amino acid substitutions can be made in the $V_H$ and the $V_L$ regions to increase yield.

In some embodiments, the heavy chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 1. In some embodiments, the light chain of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as one of SEQ ID NO: 2.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the heavy chain of the antibody, or the light chain of the antibody, or the heavy and light chains of the antibody, compared to known framework regions, or compared to the framework regions of the L9 antibody, and maintain the specific binding activity for PfCSP.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In some embodiments of the variant $V_H$ and $V_L$ sequences provided above, each CDR either is unaltered, or contains no more than one, two or three amino acid substitutions.

To increase binding affinity of the antibody, the $V_L$ and $V_H$ segments can be randomly mutated, such as within HCDR3 region or the LCDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the HCDR3 or LCDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for PfCSP. In particular examples, the $V_H$ amino acid sequence is one of SEQ ID NO: 1. In other examples, the $V_L$ amino acid sequence is one of SEQ ID NO: 2.

In some embodiments, an antibody (such as L9) or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody (such as L9) comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *Trends Biotechnol.* 15(1):26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO 2002/031140; Okazaki et al., *J. Mol. Biol.*, 336(5):1239-1249, 2004; Yamane-Ohnuki et al., *Biotechnol. Bioeng.* 87(5):614-622, 2004. Examples of cell lines capable of producing defucosylated antibodies include Lec 13 CHO cells deficient in protein fucosylation (Ripka et al., *Arch. Biochem. Biophys.* 249(2):533-545, 1986; US Pat. Appl. No. US 2003/0157108 and WO 2004/056312, especially at Example 11), and knockout cell lines, such as alpha-1,6-fucosyltransferase gene, FUT8, knockout CHO cells (see, e.g., Yamane-Ohnuki et al., *Biotechnol. Bioeng.*, 87(5): 614-622, 2004; Kanda et al., *Biotechnol. Bioeng.*, 94(4): 680-688, 2006; and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

In several embodiments, the constant region of the antibody (such as L9) comprises one or more amino acid substitutions to optimize in vivo half-life of the antibody. The serum half-life of IgG Abs is regulated by the neonatal Fc receptor (FcRn). Thus, in several embodiments, the antibody comprises an amino acid substitution that increases binding to the FcRn. Non-limiting examples of such substitutions include substitutions at IgG constant regions T250Q and M428L (see, e.g., Hinton et al., *J Immunol.*, 176(1):346-356, 2006); M428L and N434S (the "LS" mutation, see, e.g., Zalevsky, et al., *Nature Biotechnol.*, 28(2): 157-159, 2010); N434A (see, e.g., Petkova et al., *Int. Immunol.*, 18(12):1759-1769, 2006); T307A, E380A, and N434A (see, e.g., Petkova et al., *Int. Immunol.*, 18(12):1759-1769, 2006); and M252Y, S254T, and T256E (see, e.g., Dall'Acqua et al., *J. Biol. Chem.*, 281(33):23514-23524, 2006). The disclosed antibodies and antigen binding fragments can be linked to or comprise an Fc polypeptide including any of the substitutions listed above, for example, the Fc polypeptide can include the M428L and N434S substitutions.

In some embodiments, the constant region of the antibody comprises one or more amino acid substitutions to optimize ADCC. ADCC is mediated primarily through a set of closely related Fcγ receptors. In some embodiments, the antibody comprises one or more amino acid substitutions that increase binding to FcγRIIIa. Non-limiting examples of such substitutions include substitutions at IgG constant regions S239D and I332E (see, e.g., Lazar et al., *Proc. Natl., Acad. Sci. U.S.A.*, 103(11):4005-4010, 2006); and S239D, A330L, and I332E (see, e.g., Lazar et al., *Proc. Natl., Acad. Sci. U.S.A.*, 103(11):4005-4010, 2006).

Combinations of the above substitutions are also included, to generate an IgG constant region with increased binding to FcRn and FcγRIIIa. The combinations increase antibody half-life and ADCC. For example, such combinations include antibodies with the following amino acid substitutions in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E. In some examples, the antibodies, or an antigen binding fragment thereof is modified such that it is directly cytotoxic to infected cells, or uses natural defenses such as complement, ADCC, or phagocytosis by macrophages.

In some embodiments, an antibody provided herein may be further modified to contain additional nonproteinaceous moieties. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in an application under defined conditions, etc.

B. Conjugates

The antibodies and antigen binding fragments that specifically bind to PfCSP (such as L9) can be conjugated to an agent, such as an effector molecule or detectable marker. Both covalent and noncovalent attachment means may be used. Various effector molecules and detectable markers can be used, including (but not limited to) toxins and radioactive agents such as $^{125}$I, $^{32}$P, $^{14}$C, $^{3}$H and $^{35}$S and other labels, target moieties and ligands, etc. The choice of a particular effector molecule or detectable marker depends on the particular target molecule or cell, and the desired biological effect.

The procedure for attaching an effector molecule or detectable marker to an antibody or antigen binding fragment varies according to the chemical structure of the effector. Polypeptides typically contain a variety of functional groups, such as carboxyl (—COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any suitable linker molecule. The linker is capable of forming covalent bonds to both the antibody or antigen binding fragment and to the effector molecule or detectable marker. Suitable linkers include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side chains (such as through a disulfide linkage to cysteine) or the alpha carbon, or through the amino, and/or carboxyl groups of the terminal amino acids.

In view of the large number of methods that have been reported for attaching a variety of radiodiagnostic compounds, radiotherapeutic compounds, labels (such as enzymes or fluorescent molecules), toxins, and other agents to antibodies, a suitable method for attaching a given agent to an antibody or antigen binding fragment or other polypeptide can be determined.

The antibody or antigen binding fragment can be conjugated with a detectable marker; for example, a detectable marker capable of detection by ELISA, spectrophotometry, flow cytometry, microscopy or diagnostic imaging techniques (such as CT, computed axial tomography (CAT), MRI, magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP), and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitope recognized by a secondary reporter (such as leucine zipper pair sequences, binding sites for secondary antibodies, metal binding domains, epitope tags).

The antibody or antigen binding fragment can also be conjugated with a radiolabeled amino acid, for example, for diagnostic purposes. For instance, the radiolabel may be used to detect PfCSP expressing cells by radiography, emission spectra, or other diagnostic techniques. Examples of labels for polypeptides include, but are not limited to, the following radioisotopes: $^{3}$H, $^{14}$C, $^{35}$S, $^{90}$Y, $^{99m}$Tc, $^{111}$In, $^{125}$I, $^{131}$I. The radiolabels may be detected, for example, using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In some embodiments, the average number of effector molecules or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule per antibody ratio) of a conjugate may be controlled in different ways, for example, by: (i) limiting the molar excess of effector molecule-linker intermediate or linker reagent relative to antibody, (ii) limiting the conjugation reaction time or temperature, (iii) partial or limiting reducing conditions for cysteine thiol modification, (iv) engineering by recombinant techniques the amino acid sequence of the antibody such that the number and position of cysteine residues is modified for control of the number or position of linker-effector molecule attachments.

C. Polynucleotides and Expression

Nucleic acid molecules (for example, cDNA or RNA molecules) encoding the amino acid sequences of antibodies, antigen binding fragments, and conjugates that specifically bind to PfCSP (such as L9) are provided. Nucleic acids encoding these molecules can readily be produced using the amino acid sequences provided herein (such as the CDR sequences and $V_H$ and $V_L$ sequences), sequences available in the art (such as framework or constant region sequences), and the genetic code. In several embodiments, a nucleic acid molecules can encode the $V_H$, the $V_L$, or both the $V_H$ and $V_L$ (for example in a bicistronic expression vector) of a disclosed antibody or antigen binding fragment. In several embodiments, the nucleic acid molecules can be expressed in a host cell (such as a mammalian cell) to produce a disclosed antibody or antigen binding fragment.

The genetic code can be used to construct a variety of functionally equivalent nucleic acid sequences, such as nucleic acids which differ in sequence but which encode the same antibody sequence, or encode a conjugate or fusion protein including the $V_L$ and/or $V_H$ nucleic acid sequence.

In a non-limiting example, an isolated nucleic acid molecule encodes the $V_H$ of the L9 antibody or antigen binding fragment and comprises the nucleic acid sequence set forth as SEQ ID NO: 11. In a non-limiting example, an isolated nucleic acid molecule encodes the $V_L$ of the L9 antibody or antigen binding fragment and comprises the nucleic acid sequence set forth as any one of SEQ ID NOs: 12. In a non-limiting example, an isolated nucleic acid molecule encodes the $V_H$ and $V_L$ of the L9 antibody or an antigen binding fragment thereof and comprises the nucleic acid sequences set forth as any one of SEQ ID NOs: 11 and 12, respectively.

Nucleic acid molecules encoding the antibodies, antigen binding fragments, and conjugates that specifically bind to PfCSP can be prepared by any suitable method including, for example, cloning of appropriate sequences or by direct chemical synthesis by standard methods. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques can be found, for example, in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements).

Nucleic acids can also be prepared by amplification methods. Amplification methods include the polymerase chain reaction (PCR), the ligase chain reaction (LCR), the transcription-based amplification system (TAS), and the self-sustained sequence replication system (3SR).

The nucleic acid molecules can be expressed in a recombinantly engineered cell such as bacteria, plant, yeast, insect and mammalian cells. The antibodies, antigen binding fragments, and conjugates can be expressed as individual proteins including the $V_H$ and/or $V_L$ (linked to an effector molecule or detectable marker as needed), or can be expressed as a fusion protein. Any suitable method of expressing and purifying antibodies and antigen binding fragments may be used; non-limiting examples are provided in Al-Rubeai (Ed.), *Antibody Expression and Production*, Dordrecht; New York: Springer, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ domains joined by the flexible linker (see, e.g., Bird et al., *Science*, 242(4877):423-426, 1988; Huston et al., *Proc. Natl. Acad. Sci. U.S.A.*, 85(16):5879-5883, 1988; McCafferty et al., *Nature*, 348:552-554, 1990; Kontermann and Dübel (Eds.), *Antibody Engineering*, Vols. 1-2, 2$^{nd}$ ed., Springer-Verlag, 2010; Greenfield (Ed.), *Antibodies: A Laboratory Manual*, 2$^{nd}$ ed. New York: Cold Spring Harbor Laboratory Press, 2014). Optionally, a cleavage site can be included in a linker, such as a furin cleavage site.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to PfCSP and another antigen. The encoded $V_H$ and $V_L$ optionally can include a furin cleavage site between the $V_H$ and $V_L$ domains.

One or more DNA sequences encoding the antibodies, antigen binding fragments, or conjugates can be expressed in vitro by DNA transfer into a suitable host cell. The cell may be prokaryotic or eukaryotic. Numerous expression systems available for expression of proteins including *E. coli*, other bacterial hosts, yeast, and various higher eukaryotic cells such as the COS, CHO, HeLa and myeloma cell lines, can be used to express the disclosed antibodies and antigen binding fragments. Methods of stable transfer, meaning that the foreign DNA is continuously maintained in the host may be used. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signals for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, for example, a strong promoter to direct transcription, a ribosome binding site for translational initiation (e.g., internal ribosomal binding sequences), and a transcription/translation terminator. For *E. coli*, this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by any suitable method such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

Modifications can be made to a nucleic acid encoding a polypeptide described herein without diminishing its biological activity. Some modifications can be made to facilitate the cloning, expression, or incorporation of the targeting molecule into a fusion protein. Such modifications include, for example, termination codons, sequences to create conveniently located restriction sites, and sequences to add a methionine at the amino terminus to provide an initiation site, or additional amino acids (such as poly His) to aid in purification steps.

Once expressed, the antibodies, antigen binding fragments, and conjugates can be purified according to standard procedures in the art, including ammonium sulfate precipitation, affinity columns, column chromatography, and the like (see, generally, Simpson et al. (Eds.), *Basic methods in Protein Purification and Analysis: A Laboratory Manual*, New York: Cold Spring Harbor Laboratory Press, 2009). The antibodies, antigen binding fragment, and conjugates need not be 100% pure. Once purified, partially or to homogeneity as desired, if to be used prophylatically, the polypeptides should be substantially free of endotoxin.

Methods for expression of antibodies, antigen binding fragments, and conjugates, and/or refolding to an appropriate active form, from mammalian cells, and bacteria such as *E. coli* have been described and are applicable to the antibodies disclosed herein. See, e.g., Greenfield (Ed.), *Antibodies: A Laboratory Manual*, 2$^{nd}$ ed. New York: Cold Spring Harbor Laboratory Press, 2014, Simpson et al. (Eds.), *Basic methods in Protein Purification and Analysis: A Laboratory Manual*, New York: Cold Spring Harbor Laboratory Press, 2009, and Ward et al., *Nature* 341(6242): 544-546, 1989.

D. Methods and Compositions

1. Inhibiting *P. falciparum* Infection

Methods are disclosed herein for the inhibition of a *P. falciparum* infection in a subject. The methods include administering to the subject an effective amount (that is, an amount effective to inhibit *P. falciparum* infection in the subject) of a disclosed antibody (such as L9), antigen binding fragment, conjugate, or a nucleic acid encoding such an antibody, antigen binding fragment, or conjugate, to a subject at risk of a *P. falciparum* infection. The methods can be used pre-exposure or post-exposure.

*P. falciparum* infection does not need to be completely eliminated or inhibited for the method to be effective. For example, the method can decrease *P. falciparum* infection by a desired amount, for example by at least 10%, at least 20%, at least 50%, at least 60%, at least 70%, at least 80%, at least 90%, at least 95%, at least 98%, or even at least 100% (elimination or prevention of detectable *P. falciparum* infection) as compared to *P. falciparum* infection in the absence of the treatment. In some embodiments, the subject can also be treated with an effective amount of an additional agent, such as anti-malaria agent.

In some embodiments, administration of an effective amount of a disclosed antibody, antigen binding fragment, conjugate, or nucleic acid molecule, inhibits the establishment of *P. falciparum* infection and/or subsequent *P. falciparum* disease progression in a subject, which can encompass any statistically significant reduction in *P. falciparum* activity (for example, growth or invasion) or symptoms of *P. falciparum* infection in the subject.

Antibodies and antigen binding fragments thereof are typically administered by intravenous infusion. Doses of the antibody or antigen binding fragment vary, but generally range between about 0.5 mg/kg to about 50 mg/kg, such as a dose of about 1 mg/kg, about 5 mg/kg, about 10 mg/kg, about 20 mg/kg, about 30 mg/kg, about 40 mg/kg, or about 50 mg/kg. In some embodiments, the dose of the antibody or antigen binding fragment can be from about 0.5 mg/kg to about 5 mg/kg, such as a dose of about 1 mg/kg, about 2 mg/kg, about 3 mg/kg, about 4 mg/kg or about 5 mg/kg. The antibody or antigen binding fragment is administered according to a dosing schedule determined by a medical practitioner. In some examples, the antibody or antigen binding fragment is administered weekly, every two weeks, every three weeks or every four weeks.

In some embodiments, the method of inhibiting *P. falciparum* infection in a subject further comprises administration of one or more additional agents to the subject. Additional agents of interest include, but are not limited to, anti-malaria agents.

In some embodiments, the method of inhibiting *P. falciparum* infection in a subject comprises administration of a first antibody that specifically binds to PfCSP as disclosed herein (such as L9) and a second antibody that that specifically binds to PfCSP (such as any one of CIS04, CIS06, CIS23, CIS34, CIS42, CIS43, and mAb10 disclosed in PCT Pub. No. WO 2018/148660, which is incorporated by reference herein). In some embodiments, the first antibody is L9 and the second antibody is CIS43.

In some embodiments, a subject is administered DNA or RNA encoding a disclosed antibody to provide in vivo antibody production, for example using the cellular machinery of the subject. Any suitable method of nucleic acid administration may be used; non-limiting examples are provided in U.S. Pat. Nos. 5,643,578, 5,593,972 and 5,817,637. U.S. Pat. No. 5,880,103 describes several methods of delivery of nucleic acids encoding proteins to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof. In some embodiments, a disclosed antibody or antigen binding fragment is expressed in a subject using the pVRC8400 vector (described in Barouch et al., *J. Virol.*, 79(14), 8828-8834, 2005, which is incorporated by reference herein).

In several embodiments, a subject (such as a human subject at risk of *P. falciparum* infection) can be administered an effective amount of an AAV viral vector that comprises one or more nucleic acid molecules encoding a disclosed antibody or antigen binding fragment. The AAV viral vector is designed for expression of the nucleic acid molecules encoding a disclosed antibody or antigen binding fragment, and administration of the effective amount of the AAV viral vector to the subject leads to expression of an effective amount of the antibody or antigen binding fragment in the subject. Non-limiting examples of AAV viral vectors that can be used to express a disclosed antibody or antigen binding fragment in a subject include those provided in Johnson et al., *Nat. Med.*, 15(8):901-906, 2009 and Gardner et al., *Nature*, 519(7541):87-91, 2015, each of which is incorporated by reference herein in its entirety.

In one embodiment, a nucleic acid encoding a disclosed antibody, or antigen binding fragment thereof, is introduced directly into tissue. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

Single or multiple administrations of a composition including a disclosed PfCSP-specific antibody, antigen binding fragment, conjugate, or nucleic acid molecule encoding such molecules, can be administered depending on the dosage and frequency as required and tolerated by the patient. The dosage can be administered once, but may be applied periodically until either a desired result is achieved or until side effects warrant discontinuation of therapy. Generally, the dose is sufficient to inhibit *P. falciparum* infection without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The effective dose can be determined from cell culture assays and animal studies.

The PfCSP-specific antibody, antigen binding fragment, conjugate, or nucleic acid molecule encoding such molecules, or a composition including such molecules, can be administered to subjects in various ways, including local and systemic administration, such as, e.g., by injection subcutaneously, intravenously, intra-arterially, intraperitoneally, intramuscularly, intradermally, or intrathecally. In an embodiment, the antibody, antigen binding fragment, conjugate, or nucleic acid molecule encoding such molecules, or a composition including such molecules, is administered by a single subcutaneous, intravenous, intra-arterial, intraperitoneal, intramuscular, intradermal or intrathecal injection once a day. The antibody, antigen binding fragment, conjugate, or nucleic acid molecule encoding such molecules, or a composition including such molecules, can also be administered by direct injection at or near the site of disease. A further method of administration is by osmotic pump (e.g., an Alzet pump) or mini-pump (e.g., an Alzet mini-osmotic pump), which allows for controlled, continuous and/or slow-release delivery of the antibody, antigen binding fragment, conjugate, or nucleic acid molecule encoding such molecules, or a composition including such molecules, over a pre-determined period. The osmotic pump or mini-pump can be implanted subcutaneously, or near a target site.

2. Compositions

Compositions are provided that include one or more of the PfCSP-specific antibody, antigen binding fragment, conjugate, or nucleic acid molecule encoding such molecules, that are disclosed herein in a pharmaceutically acceptable carrier. In some embodiments, the composition comprises the L9 antibody disclosed herein. In some embodiments, the composition comprises the L9 antibody and one or more additional CSP-specific antibody, such as CIS43. The compositions are useful, for example, for the inhibition or detection of a *P. falciparum* infection. The compositions can be prepared in unit dosage forms for administration to a subject. The amount and timing of administration are at the discretion of the administering physician to achieve the desired purposes. The PfCSP-specific antibody, antigen binding fragment, conjugate, or nucleic acid molecule encoding such molecules can be formulated for systemic or local administration. In one example, the PfCSP-specific antibody, antigen binding fragment, conjugate, or nucleic acid molecule encoding such molecules, is formulated for parenteral administration, such as intravenous administration.

In some embodiments, the antibody, antigen binding fragment, or conjugate thereof, in the composition is at least 70% (such as at least 75%, at least 80%, at least 85%, at least 90%, at least 95%, at least 96%, at least 97%, at least 98% or at least 99%) pure. In some embodiments, the composition contains less than 10% (such as less than 5%, less than 4%, less than 3%, less than 2%, less than 1%, less than 0.5%, or even less) of macromolecular contaminants, such as other mammalian (e.g., human) proteins.

The compositions for administration can include a solution of the PfCSP-specific antibody, antigen binding fragment, conjugate, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by any suitable technique. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration comprises about 0.01 to about 30 mg/kg of antibody or antigen binding fragment or conjugate per subject per day (or the corresponding dose of a conjugate including the antibody or antigen binding fragment). Any suitable method may be used for preparing administrable compositions; non-limiting examples are provided in such publications as *Remington: The Science and Practice of Pharmacy*, $22^{nd}$ ed., London, UK: Pharmaceutical Press, 2013. In some embodiments, the composition can be a liquid formulation including one or more antibodies, antigen binding fragments (such as an antibody or antigen binding fragment that specifically binds to PfCSP), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of Rituximab in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30-minute period if the previous dose was well tolerated.

Controlled-release parenteral formulations can be made as implants, oily injections, or as particulate systems. For a broad overview of protein delivery systems see, Banga, *Therapeutic Peptides and Proteins: Formulation, Processing, and Delivery Systems*, Lancaster, PA: Technomic Publishing Company, Inc., 1995. Particulate systems include microspheres, microparticles, microcapsules, nanocapsules, nanospheres, and nanoparticles. Microcapsules contain the active protein agent, such as a cytotoxin or a drug, as a central core. In microspheres, the active protein agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, *Colloidal Drug Delivery Systems*, J. Kreuter (Ed.), New York, NY: Marcel Dekker, Inc., pp. 219-342, 1994; and Tice and Tabibi, *Treatise on Controlled Drug Delivery: Fundamentals, Optimization, Applications*, A. Kydonieus (Ed.), New York, NY: Marcel Dekker, Inc., pp. 315-339, 1992.

Polymers can be used for ion-controlled release of the antibody compositions disclosed herein. Any suitable polymer may be used, such as a degradable or nondegradable polymeric matrix designed for use in controlled drug delivery. Alternatively, hydroxyapatite has been used as a microcarrier for controlled release of proteins. In yet another aspect, liposomes are used for controlled release as well as drug targeting of the lipid-capsulated drug.

3. Methods of Detection and Diagnosis

Methods are also provided for the detection of the presence of PfCSP in vitro or in vivo. In one example, the presence of PfCSP is detected in a biological sample from a subject, and can be used to identify a subject with *P. falciparum* infection. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, with an antibody or antigen binding fragment that specifically binds to PfCSP, or conjugate thereof (e.g., a conjugate including a detectable marker) under conditions sufficient to form an immune complex, and detecting the immune complex (e.g., by detecting a detectable marker conjugated to the antibody or antigen binding fragment.

In one embodiment, the antibody or antigen binding fragment is directly labeled with a detectable marker. In another embodiment, the antibody that binds *P. falciparum* (the primary antibody) is unlabeled and a secondary antibody or other molecule that can bind the primary antibody is utilized for detection. The secondary antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially. Suitable labels for the antibody, antigen binding fragment or secondary antibody are known and described above, and include various enzymes, prosthetic groups, fluorescent materials, luminescent materials, magnetic agents and radioactive materials.

In some embodiments, the disclosed antibodies or antigen binding fragments thereof are used to test vaccines. For example to test if a vaccine composition including a PfCSP or fragment thereof assumes a conformation including the epitope of a disclosed antibody. Thus provided herein is a method for testing a vaccine, wherein the method comprises contacting a sample containing the vaccine, such as a PfCSP immunogen, with a disclosed antibody or antigen binding fragment under conditions sufficient for formation of an immune complex, and detecting the immune complex, to detect the vaccine with an PfCSP immunogen including the epitope in the sample. In one example, the detection of the immune complex in the sample indicates that vaccine component, such as a PfCSP immunogen assumes a conformation capable of binding the antibody or antigen binding fragment.

III. EXAMPLES

The following example is provided to illustrate particular features of certain embodiments, but the scope of the claims should not be limited to those features exemplified.

Example 1

L9, a Human Monoclonal Antibody that Prevents Malaria Infection

This example illustrates identification and characterization of the L9 antibody, which specifically binds to PfCSP and inhibits infection in an animal model of malaria infection.

L9 represents a significant advancement over previously described anti-PfCSP human antibodies. As discussed below, L9 shows preferential high-affinity binding to NVDP (SEQ ID NO: 30) minor repeats and multi-valent binding to NANP (SEQ ID NO: 31) major repeats of PfCSP. L9 was also shown to be more potent than a large panel of previously reported anti-PfCSP human antibodies, and also more protective against sporozoite challenge in mice than a panel of previously reported anti-PfCSP monoclonal antibodies. Intravital imaging demonstrated that L9 mediated protection by limiting sporozoite motility and invasion of capillaries in the skin, and by preventing sporozoite egress from liver sinusoids and subsequent traversal and infection of hepatocytes. The functional superiority of L9 has multiple benefits. Non-limiting examples include that a more potent antibody may provide improved and more durable protection, as it would reach the threshold of protection at lower serum concentrations and so will remain above that threshold for longer after infusion at a given dose. Additionally, a more potent antibody could be used to confer equivalent protection at a lower dose. This results in lower costs of goods and may also enable subcutaneous antibody delivery, which is easier than the currently used intravenous method of delivery.

Malaria is a mosquito-borne parasitic disease affecting ~200-400 million people leading to ~400,000 deaths annually, primarily in children in sub-Saharan Africa. Antimalarial drugs, insecticide-treated nets, and other public health interventions contributed to a 50-75% reduction in global malaria cases between 2000-2015. Despite these efforts, malaria incidence has increased in many areas since 2015. These data highlight the need for additional preventative interventions to control and eliminate malaria.

A long-sought goal for preventing malaria is the development of an effective vaccine. RTS,S, a protein subunit vaccine administered with the adjuvant AS01, is the most clinically advanced vaccine against *Plasmodium falciparum* (Pf), the species that accounts for most malaria-associated mortality. In phase III clinical trials, three vaccinations with RTS,S/AS01 conferred ~50% protection against clinical disease at one year and ~30% protection over four years in 5-17 month-old infants. High antibody titers are associated with protection but wane over time and require further vaccine boosting. An alternative approach that may mediate higher levels of protection for defined periods of time is passive immunization with highly potent monoclonal antibodies (mAbs).

Antibodies can prevent malaria by neutralizing sporozoites (SPZ; the infectious form of parasites deposited in the skin when a mosquito bites) in the skin, vasculature, and liver before they infect hepatocytes (Cockburn et al., Nat. Immunol. 19, 1199-1211, 2018). The major target of anti-PfSPZ antibodies is the PfCSP. PfCSP is the most abundant SPZ surface protein and is essential for their motility and invasion of hepatocytes (Tewari et al., J. Biol. Chem. 277, 47613-47618, 2002; Cerami et al., Cell. 70, 1021-1033, 1992). PfCSP has three domains: an N-terminus, a central region composed of repeating tetrapeptides (1 NPDP (SEQ ID NO: 29), 4 NVDP (SEQ ID NO: 30), and 38 NANP (SEQ ID NO: 31) in the 3D7 reference strain), and a C-terminus (Draper et al., Cell Host Microbe. 24, 43-56, 2018; Cockburn et al., Nat. Immunol. 19, 1199-1211, 2018; Wardemann et al., Curr. Opin. Immunol. 53, 119-123, 2018). In 3D7, the junctional region between the N-terminus and repeat region begins with NPDP (SEQ ID NO: 29) followed by 3 interspered NANP (SEQ ID NO: 31) and NVDP (SEQ ID NO: 30) repeats, then 35 NANP (SEQ ID NO: 31) repeats with the fourth NVDP (SEQ ID NO: 30) inserted after the twentieth NANP (SEQ ID NO: 31) (Bowman. et al. Nature 400, 532-538, 1999; Hall et al. Nature 419, 527-531, 2002). Structural studies have indicated that anti-repeat binding motifs are actually DPNA (SEQ ID NO: 37) (NPDP, SEQ ID NO: 29), NPNV (SEQ ID NO: 38) (NVDP, SEQ ID NO: 30), and NPNA (SEQ ID NO: 38) (NANP, SEQ ID NO: 31), derived from the joining of various major and minor repeats (Oyen et al. Proc. Natl. Acad. Sci. U.S.A. 114, E10438-E10445, 2017; Ghasparian et al. Chem. Commun. (Camb.) 174-176, 2006; Dyson et al. Biochemistry 29, 7828-7837, 1990; Oyen et al. Sci Adv 4, eaau8529, 2018; Plassmeyer et al. J. Biol. Chem. 284, 26951-26963, 2009). Importantly, RTS,S includes a truncated form of PfCSP containing 19 NANP (SEQ ID NO: 31) repeats and the C-terminus, but not the N-terminus, NPDP (SEQ ID NO: 29) or NVDP (SEQ ID NO: 30) minor repeats (Stoute et al. N. Engl. J. Med. 336, 86-91, 1997). Mouse and human mAbs have been characterized against all domains of PfCSP (Draper et al., Cell Host Microbe. 24, 43-56, 2018; Cockburn et al., Nat. Immunol. 19, 1199-1211, 2018). One mouse N-terminal mAb has been reported to mediate some protection against SPZ challenge in mice (Espinosa et al. J. Infect. Dis. 212, 1111-1119, 2015), while no protective C-terminal mAbs have been reported so far (Scally et al. J. Exp. Med. 215, 63-75, 2018). Most isolated mAbs that mediate protection in vivo bind the immunodominant NANP (SEQ ID NO: 31) major repeats (Oyen et al., Proc. Natl. Acad. Sci. U.S.A. 114, E10438-E10445, 2017; Imkeller et al., Science. 360, 1358-1362, 2018; Triller et al., Immunity 47, 1197-1209.e10, 2017; Zavala et al., J. Exp. Med. 157, 1947-1957, 1983). Recently, the isolation of highly potent human mAbs against the unique tetrapeptide, NPDP (SEQ ID NO: 29), at the junction of the N-terminus and repeat region identified this "junctional epitope" as a new site of neutralization (Tan et al., Nat. Med. 24, 401-407, 2018; Kisalu et al., Nat. Med. 24, 408-416, 2018; Draper et al., Nat. Med. 24, 382-383, 2018). This discovery has led to ongoing efforts to identify new mAbs with greater potency against the junctional epitope or other motifs in the repeat region of PfCSP.

This example illustrates the first neutralizing human mAb (called L9) that preferentially binds the NVDP (SEQ ID NO: 30) minor repeats of PfCSP. The in vivo protective potency of L9 was compared to a panel of six recently characterized neutralizing human PfCSP mAbs (Oyen et al., Proc. Natl. Acad. Sci. U.S.A. 114, E10438-E10445, 2017; Imkeller et al., Science. 360, 1358-1362, 2018; Tan et al., Nat. Med. 24, 401-407, 2018; Kisalu et al., Nat. Med. 24, 408-416, 2018) across multiple mouse challenge models and doses to establish a hierarchy of in vivo potency. Moroever, biochemical and biophysical assays were used to characterize this panel of mAbs based on their different binding characteristics to PfCSP peptides and full-length protein. In addition, while previous studies have assessed how mouse CSP mAbs inhibit SPZ in vitro or in the skin (Espinosa et al., J. Infect. Dis. 212, 1111-1119, 2015; Flores-Garcia et al., mBio. 9, e02194-18, 2018; Aliprandini et al., Nat Microbiol. 3, 1224-1233, 2018; Vanderberg et al., International Journal for Parasitology. 34, 991-996, 2004), there is limited data on the mechanisms by which human PfCSP mAbs with differential binding specificities neutralize SPZ in the skin and liver. Thus, intravital imaging was used to visualize how this panel of mAbs may neutralize SPZ in the liver, the final physiological site for antibodies to prevent SPZ from initiating a symptomatic blood-stage infection.

Results

Figure 7A:
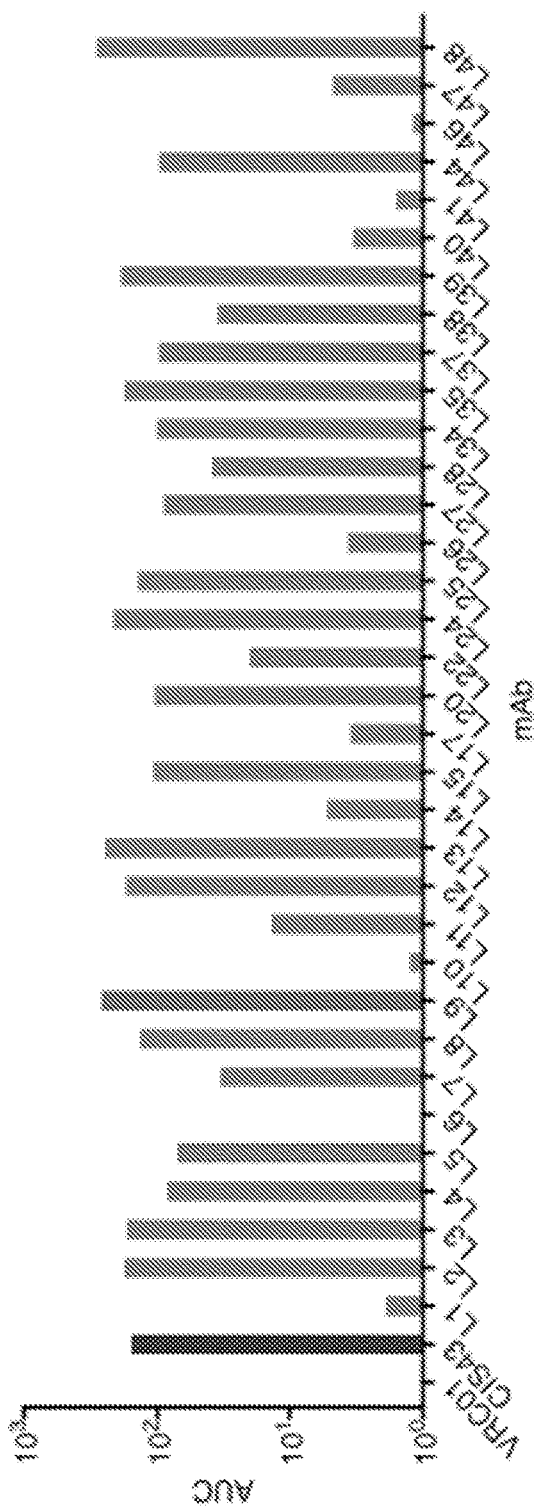
FIGS. 7A-7C. Binding characteristics and functional activity of a new panel of 28 PfCSP mAbs.
Figure 7B:
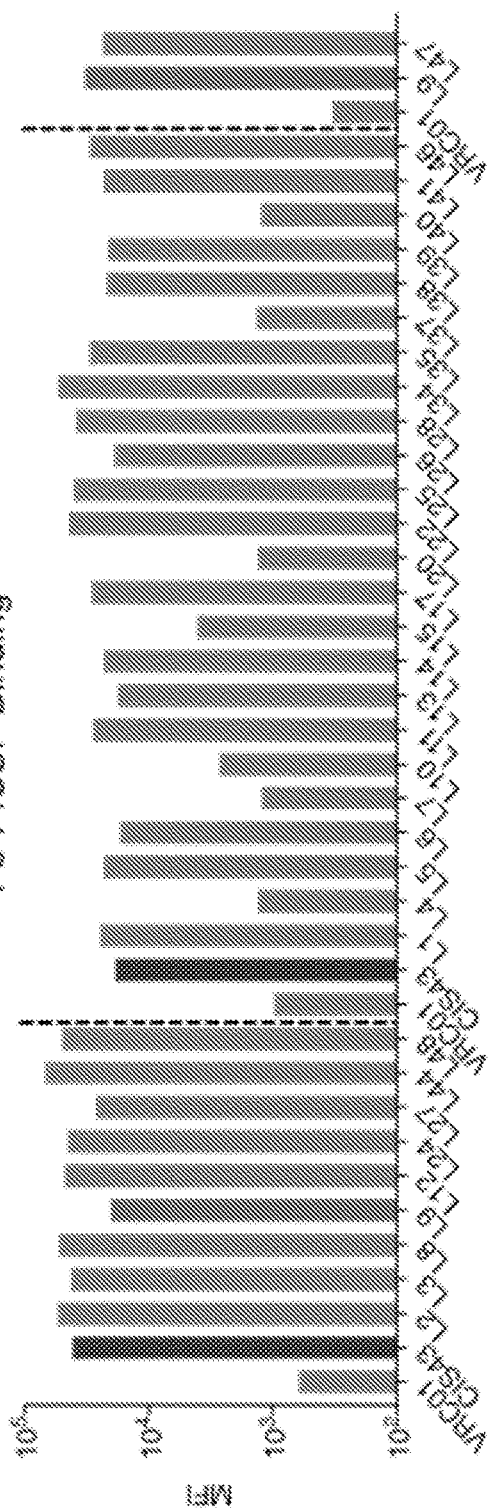

Isolation of a Protective Human mAb that Preferentially Binds the Minor Repeats of PfCSP CIS43, a human mAb targeting the junctional epitope of PfCSP isolated from a volunteer immunized with attenuated *P. falciparum* sporozoites (PfSPZ Vaccine) (Seder et al. Science 341, 1359-1365, 2013), was previously shown to protect mice from SPZ challenge (Kisalu et al. Nat. Med. 24, 408-416, 2018). To isolate additional and potentially more potent junctional mAbs, sera of volunteers immunized with higher doses of the PfSPZ Vaccine were tested for reactivity against a conformationally stabilized junctional epitope mimic, S02, designed to select for CIS43-like mAbs. One subject that had the highest S02 titers and was protected following controlled human malaria infection was selected for mAb isolation. PfCSP-reactive memory B cells (MBCs) were sorted from peripheral blood collected four weeks after the last immunization using fluorescent probes for recombinant full-length PfCSP (rPfCSP) and S02. Of 48 isolated mAbs, 28 showed binding to rPfCSP (FIG. 7A). Of those 28, 24 also showed binding to transgenic *P. berghei* (Pb) SPZ expressing full-length PfCSP, GFP, and luciferase (Pb-PfCSP SPZ GFP/Luc; hereafter Pb-PfCSP) (FIG. 7B). Most rPfCSP-specific mAbs belonged to the immunoglobulin variable heavy chain gene family 3 (IGV$_H$3), particularly IGV$_H$3-33 (13 of 28, 46%) and IGV$_H$3-30 (4 of 28, 14%).

Figure 7C:
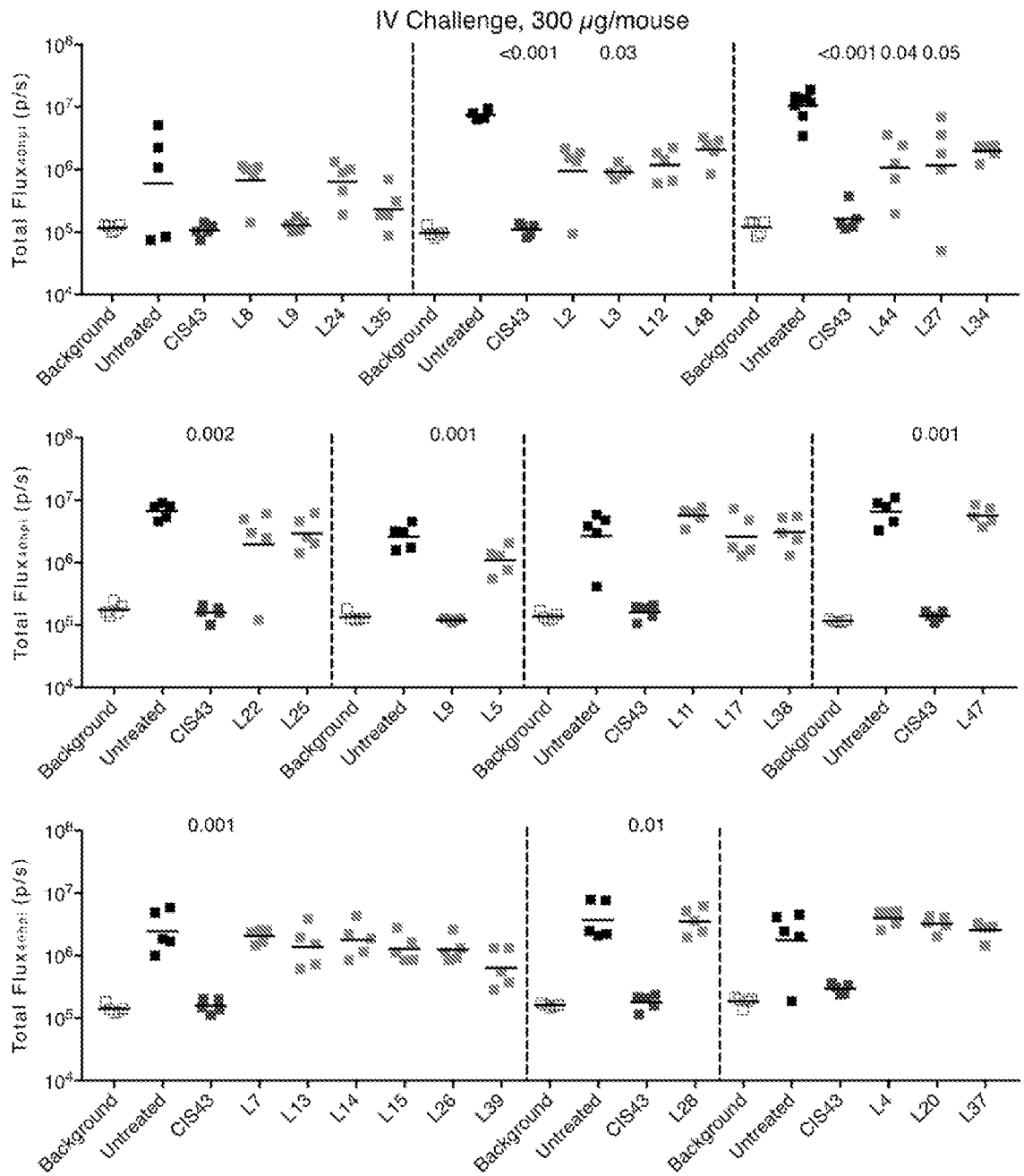

The 28 rPfCSP-reactive mAbs were then assessed for their ability to reduce parasite liver burden in mice challenged intravenously (IV) with Pb-PfCSP 2 hours after passive transfer, a model used to screen mAbs for in vivo functional activity (Espinosa et al. J. Infect. Dis. 212, 1111-1119, 2015; Kisalu et al. Nat. Med. 24, 408-416, 2018; Raghunandan et al. Malar. J. 19, 113, 2020). All mAbs were benchmarked against CIS43 at a dose of 300 µg/mouse, which confers maximum protection in this model. Only one of these new mAbs, L9, reduced liver burden comparably to CIS43 at 300 µg/mouse (FIG. 7C). At a more limiting dose of 100 µg/mouse, L9 trended towards greater liver burden reduction than CIS43 (P=0.06) (FIG. 1A), suggesting that L9 might be more protective than CIS43.

Figure 1B:
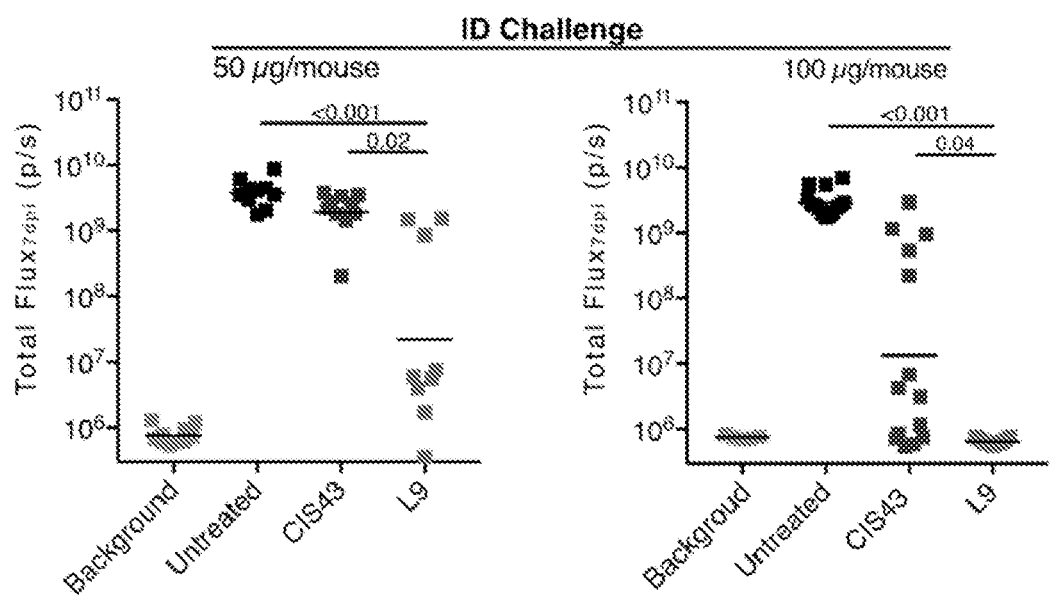
Figure 1C:
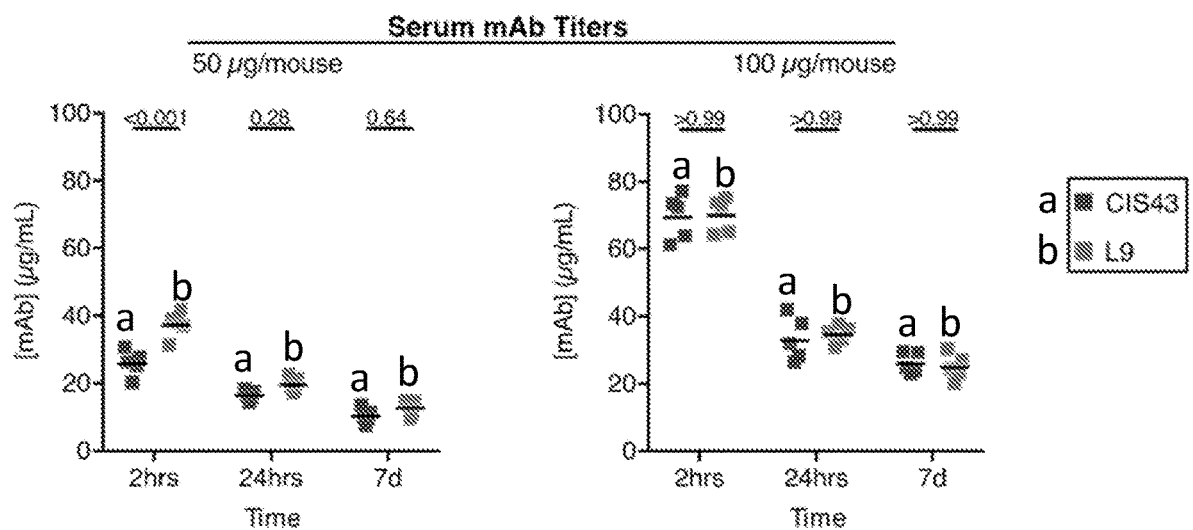

To determine whether L9 was significantly more potent than CIS43, both mAbs' capacity to reduce parasitemia following intradermal (ID) challenge with Pb-PfCSP were assessed. IV challenge bypasses the skin, a major site for antibody-mediated SPZ neutralization (Flores-Garcia et al. mBio 9, e02194-18, 2018; Aliprandini et al. Nat Microbiol 3, 1224-1233, 2018; Vanderberg et al. International Journal for Parasitology 34, 991-996, 2004), and is thus more stringent than ID challenge. However, ID challenge is more physiologically relevant because it mimics the natural route of malaria transmission by mosquito bite. To define an optimal ID challenge timepoint in which passively transferred mAbs have equilibrated into the skin, a kinetic analysis of L9 titers in skin and serum was performed over 7 days. While L9 was detectable in the skin at 2 hours (~10 µg mAb/g tissue), it peaked at 24 hours (~35 µg/g) and reached steady state by 3 days (~15 µg/g). L9 serum titers peaked at 2 hours (~250 µg/mL) and also reached steady state by 3 days (~150 µg/mL). Based on these pharmacokinetic (PK) data, the ID challenge was performed 3 days after passive transfer to ensure that mAb levels were at steady state. At both 50 and 100 µg/mouse, L9 significantly reduced parasitemia compared to CIS43 (FIG. 1B). Serum antibody levels of L9 were equivalent to CIS43 in separate groups of mice treated with 50 or 100 µg of each mAb and sampled over multiple timepoints (FIG. 1C), substantiating that L9 is more potent than CIS43.

Figure 1D:
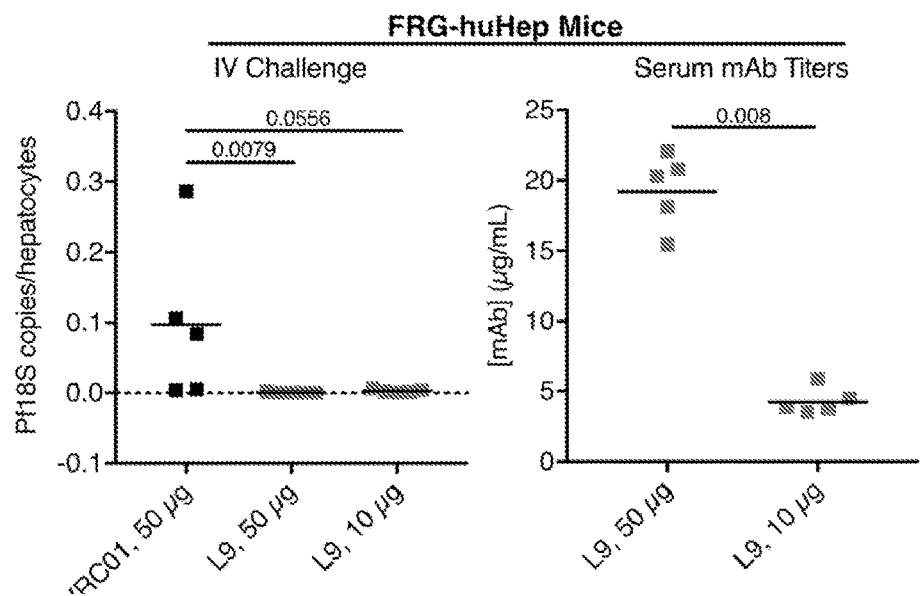

To demonstrate that L9 can also inhibit PfSPZ, we assessed whether L9 reduced liver burden in human liver-chimeric (FRG-huHep) mice challenged IV with PfSPZ (Foquet et al. Front Immunol 9, 524, 2018). Remarkably, only 50 or 10 µg of L9 (which resulted in serum concentrations as low as ~5 µg/mL) was required to reduce liver burden to near undetectable levels (FIG. 1D). Moreover, in a separate study 25 µg/mouse of L9 reduced liver burden significantly more than 2A10, an NPNA (SEQ ID NO: 38)-preferring mouse mAb commonly used as a benchmark in protection studies (Oyen et al. Proc. Natl. Acad. Sci. U.S.A. 114, E10438-E10445, 2017; Espinosa et al. J. Infect. Dis. 212, 1111-1119, 2015; Zavala et al. J. Exp. Med. 157, 1947-1957, 1983; Kisalu et al. Nat. Med. 24, 408-416, 2018). Collectively, these data show that L9 mediates protection against SPZ challenge in two complementary mouse models of *P. falciparum* malaria infection and is more protective than CIS43 at similar serum concentrations.

Figure 1E:
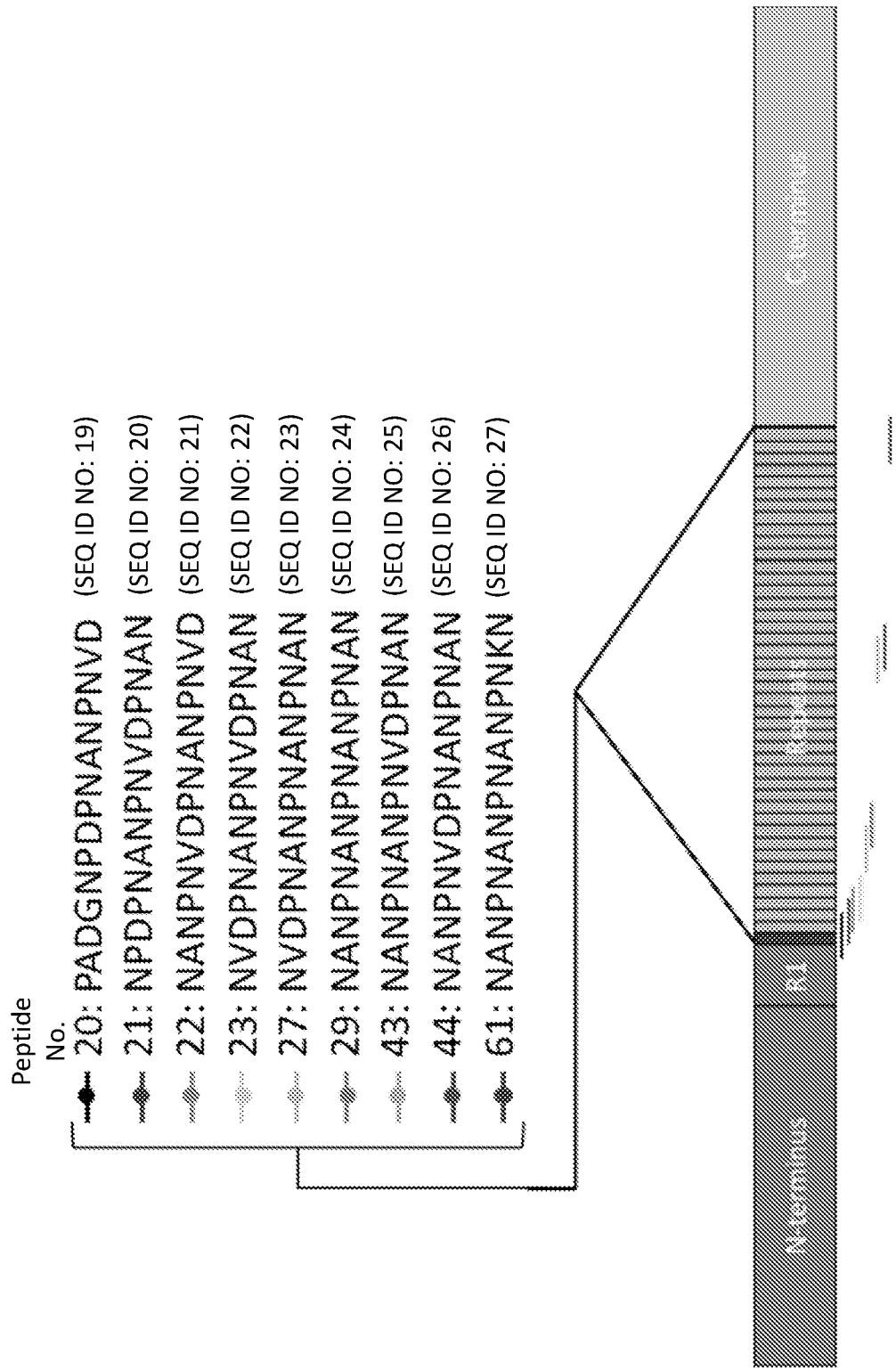
Figures 1F, 1G:
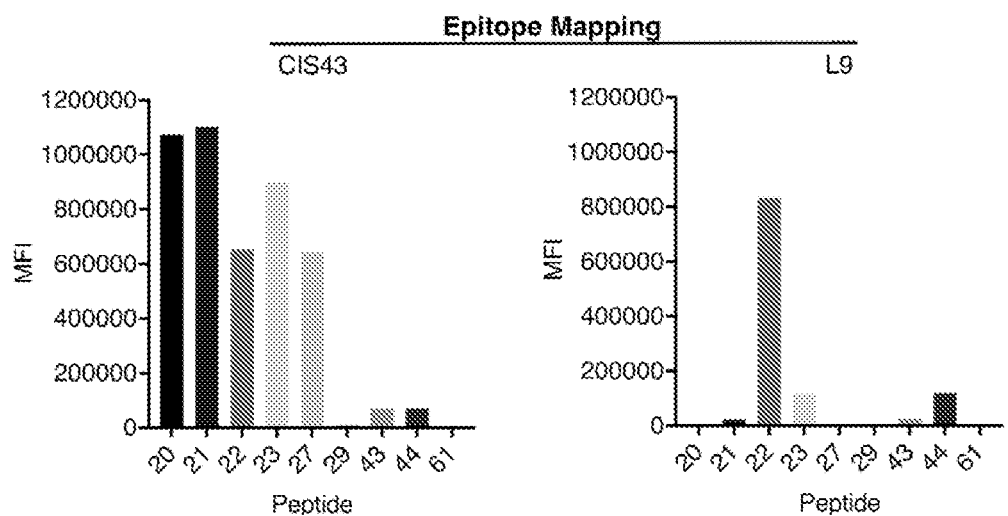

To define the specific epitope recognized by L9, mapping of L9 was performed using a series of overlapping peptides covering the repeat region of PfCSP (peptides 20-61; FIG. 1E) and compared to CIS43 as a benchmark (FIG. 1F). Consistent with previous reports (Kisalu et al. Nat. Med. 24, 408-416, 2018), CIS43 demonstrated preferential high-affinity binding to peptide 20 (PADGNPDPNANPNVD, SEQ ID NO: 19) and 21 (NPDPNANPNVDPNAN, SEQ ID NO: 20), which contain NPDP (SEQ ID NO: 29). Conversely, L9 preferentially bound peptide 22 (NANPNVDPNANPNVD, SEQ ID NO: 21) downstream of NPDP (SEQ ID NO: 29). Neither mAb bound peptide 29 (NANPNANPNANPNAN, SEQ ID NO: 24), which contains only NPNA (SEQ ID NO: 38) repeats. Alanine scanning mutagenesis of peptide 22 demonstrated that the two NPNV (SEQ ID NO: 32) motifs were critical for L9 binding (FIG. 1G). Importantly, peptide 22 is the only peptide that contains two NPNV (SEQ ID NO: 32) motifs (FIG. 1E), likely accounting for its strong recognition by L9. These data demonstrate that L9 recognizes an epitope distinct to CIS43 and that both mAbs exhibit undetectable affinity for the 3 NPNA (SEQ ID NO: 38) repeats in peptide 29 in this assay.

Peptide Binding Characteristics of a Panel of Neutralizing Human PfCSP mAbs

Figure 2A:
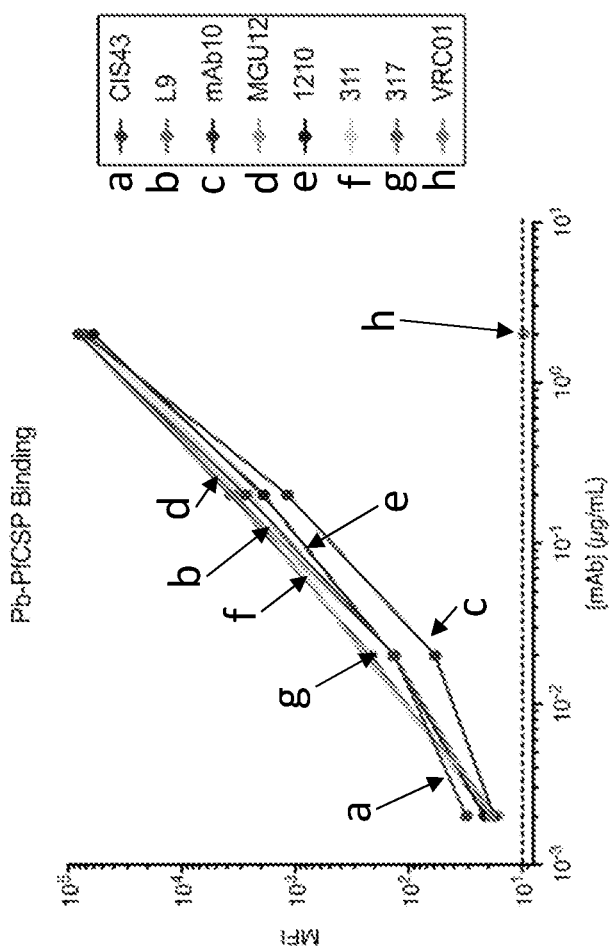
FIGS. 2A-2E. Peptide mapping of seven neutralizing human PfCSP mAbs.
Figure 2B:
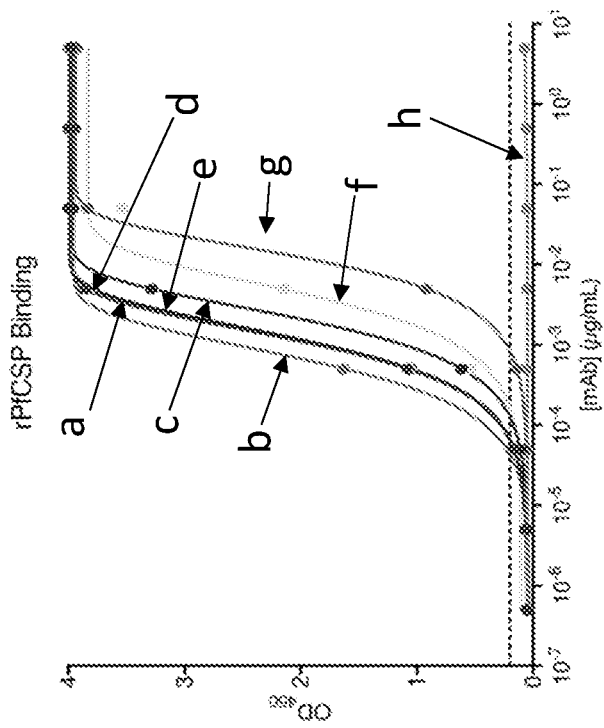

Having established L9 as a new neutralizing PfCSP mAb, its binding characteristics and protective capacity was compared against six of the most potent human PfCSP mAbs published to date (CIS43, mAb10, MGU12, 1210, 311, and 317). (Kisalu et al. Nat. Med. 24, 408-416, 2018; Tan et al. Nat. Med. 24, 401-407, 2018; Imkeller et al. Science 360, 1358-1362, 2018; Oyen et al. Proc. Natl. Acad. Sci. U.S.A. 114, E10438-E10445, 2017). All mAbs were expressed in the same IgG$_1$ vector with identical constant regions and were first verified to bind rPfCSP and Pb-PfCSP. All mAbs showed comparable dose-dependent binding to rPfCSP by ELISA (FIG. 2A), with half maximal effective concentration (EC$_{50}$) values ranging from 0.003-0.007 µg/mL, though 311 and 317 had higher EC$_{50}$ values (0.02 and 0.04 µg/mL, respectively). All mAbs showed similar binding to PfCSP on the surface of Pb-PfCSP by flow cytometry (FIG. 2B).

Figure 2C:
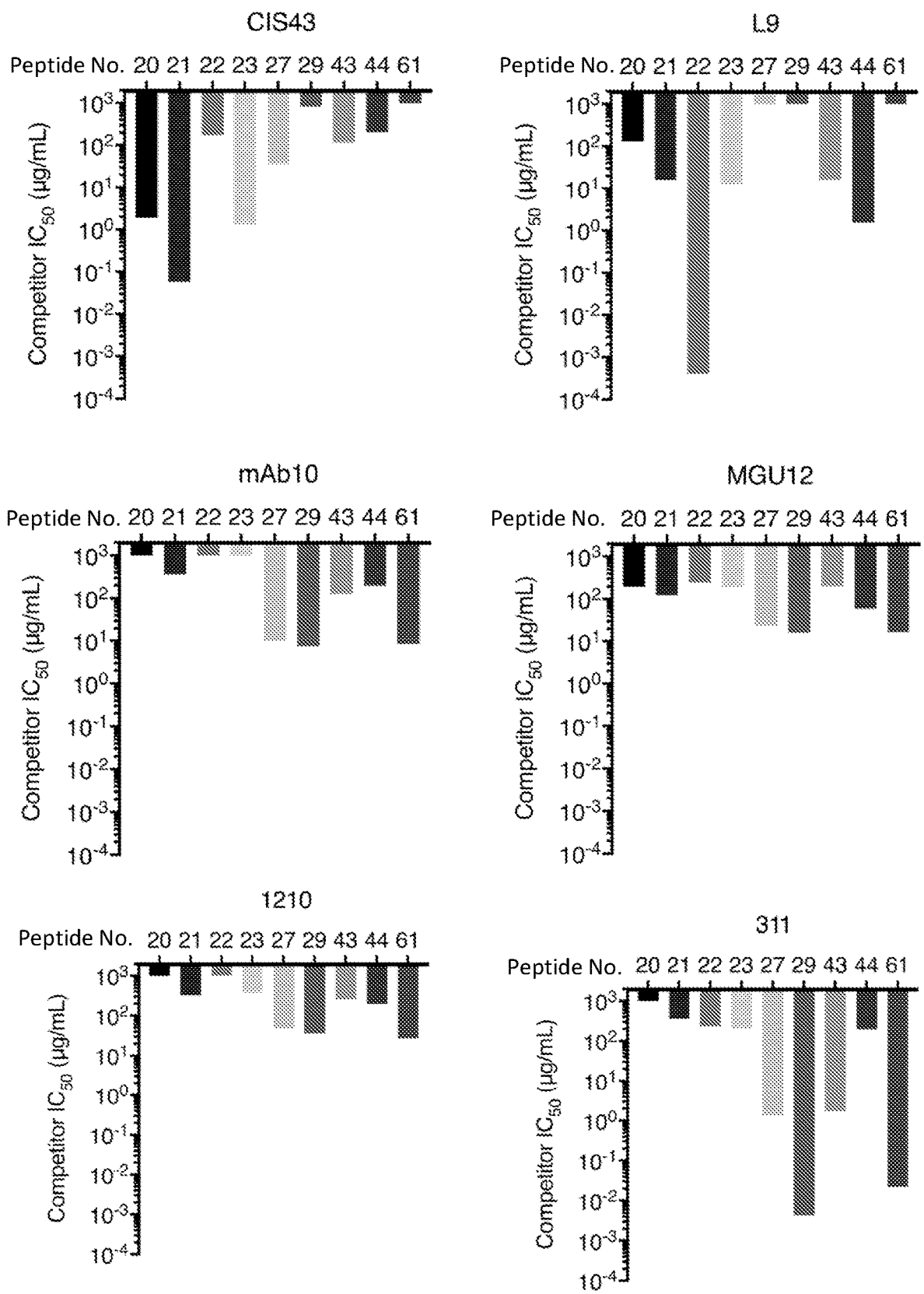
Figure 2D:
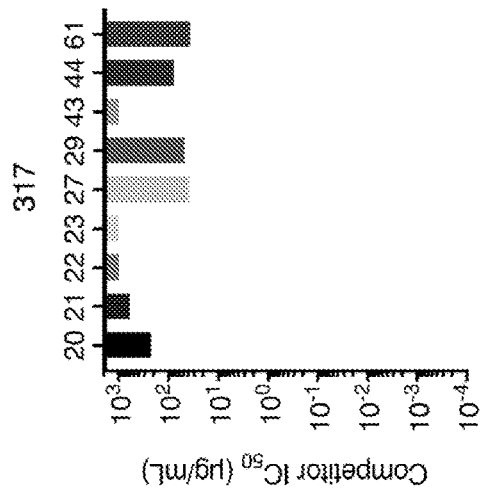
Figure 8A:
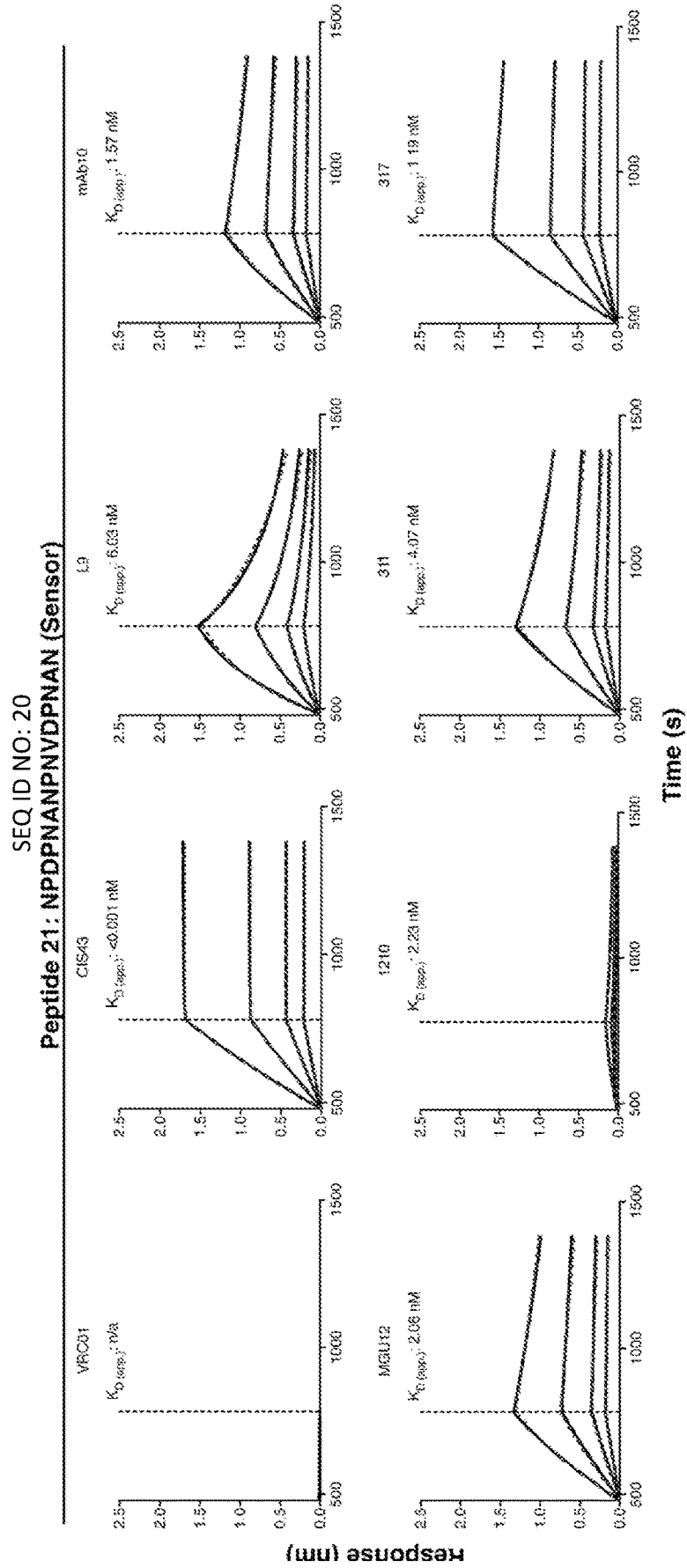
FIGS. 8A-8C. Biolayer interferometry of seven neutralizing human PfCSP mAbs binding to peptides 21, 22, and 29. Antibody binding curves are shown in with solid line (raw data), and data were fitted with the binding equations describing a 1:1 heterologous ligand interaction (dotted line). Serial concentrations of antibodies used are as follow: 1.25, 0.625, 0.3125, and 0.15625 µg/mL. Apparent avidity ($K_{D(app)}$) of VRC01 and PfCSP mAbs is shown. Data is representative of two independent experiments.
Figure 8B:
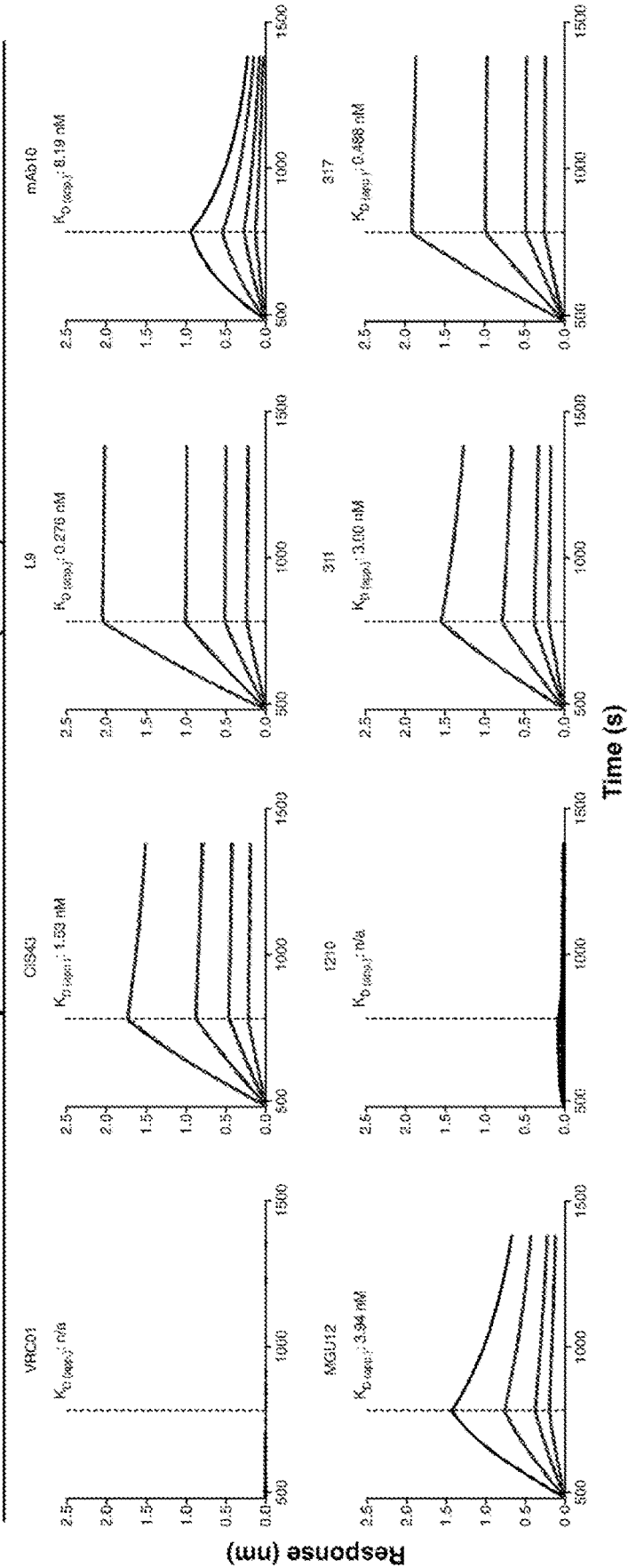

The preferred peptides and epitope(s) for each mAb on PfCSP were determined by competition ELISA with peptides 20-61 (FIGS. 2C-2D). Competition ELISA uses a range of peptide concentrations to compete mAb binding to full-length rPfCSP and is thus more sensitive than peptide mapping at a single mAb concentration (FIG. 1F). All mAbs except CIS43 and L9 were preferentially competed by peptides containing only NPNA (SEQ ID NO: 38) repeats (i.e., peptide 29). Conversely, rPfCSP binding by CIS43 and L9 was preferentially competed by peptides 21 (half maximal inhibitory concentration, IC$_{50}$=0.06 µg/mL) and 22 (IC$_{50}$=0.0004 µg/mL), respectively, and exhibited negligible competition by peptide 29 (IC$_{50}$=817.5 µg/mL and IC$_{50}$>1,000 µg/mL, respectively). The peptide preferences of these seven mAbs were substantiated using biolayer interferometry (BLI) to directly measure their apparent binding avidity to peptides 21, 22, and 29 (FIGS. 8A-8B).

Figure 2E:
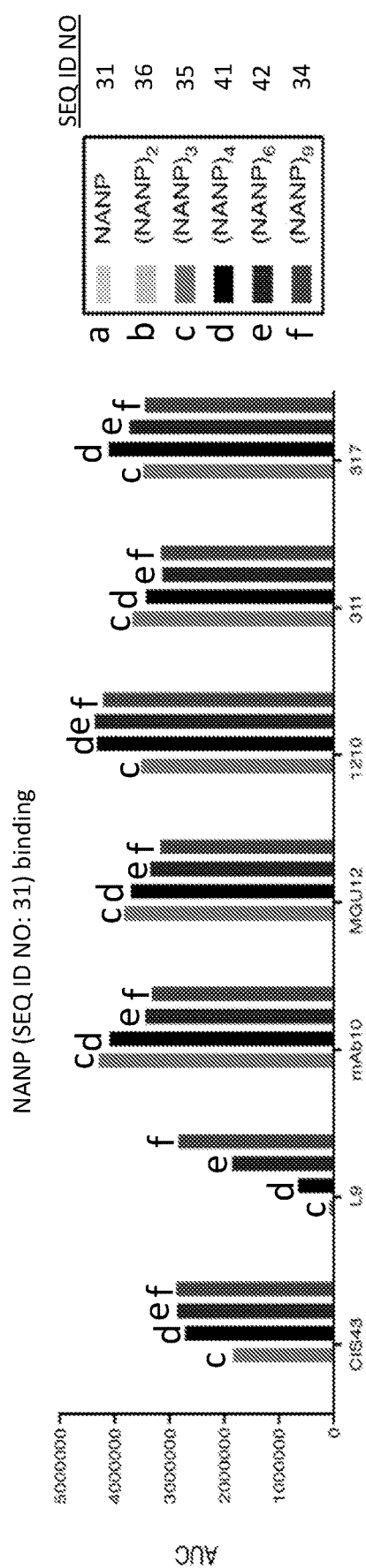

Since the panel of mAbs showed different binding affinities for peptide 29 (which only contains NPNA (SEQ ID NO: 38) repeats), we determined the minimal number of NPNA (SEQ ID NO: 38) repeats required for binding using (NANP)$_1$ (SEQ ID NO: 31) to (NANP)$_9$ (SEQ ID NO: 34) peptides (FIG. 2E). None of the mAbs bound (NANP)$_1$ (SEQ ID NO: 31) or (NANP)$_2$ (SEQ ID NO: 36), consistent with previous reports that the minimum epitope of PfCSP repeat mAbs is 2 NPNA (SEQ ID NO: 38) repeats (Oyen et al. Proc. Natl. Acad. Sci. U.S.A. 114, E10438-E10445, 2017; Oyen et al. Sci Adv 4, eaau8529, 2018; Imkeller et al. Science 360, 1358-1362, 2018). mAb10, MGU12, 1210, 311, and 317 bound peptides with ≥2 NPNA (SEQ ID NO: 38) repeats (i.e., (NANP)$_3$ (SEQ ID NO: 35) or higher) with greater affinity than CIS43 and L9. Interestingly, L9 binding increased from nearly undetectable for (NANP)$_3$ (SEQ ID NO: 35) to (NANP)$_9$ (SEQ ID NO: 34 binding that was comparable to CIS43, though still ~12-48% less than the other mAbs. These data show that, although CIS43 and L9 respectively prefer DPNA (SEQ ID NO: 37) and NPNV (SEQ ID NO: 32) motifs, they can bind NPNA (SEQ ID NO: 38) when it is sufficiently concatenated on long peptides, full-length rPfCSP, and SPZ.

Protein Binding Characteristics of a Panel of Neutralizing Human PfCSP mAbs

To correlate the peptide binding characteristics of this panel of mAbs to their recognition of full-length recombinant protein, isothermal titration calorimetry (ITC) was used to characterize the affinity and stoichiometry (i.e., valency) of their binding to rPfCSP. It was previously reported that CIS43 IgG binds rPfCSP with two sequential high-affinity events by ITC (termed "two-step binding"): the first binding event involves ~1 binding site to NPDP (SEQ ID NO: 29) and the second involves ~5 binding sites to NANP (SEQ ID NO: 31) repeats (Kisalu et al. Nat. Med. 24, 408-416, 2018).

Figure 3A:
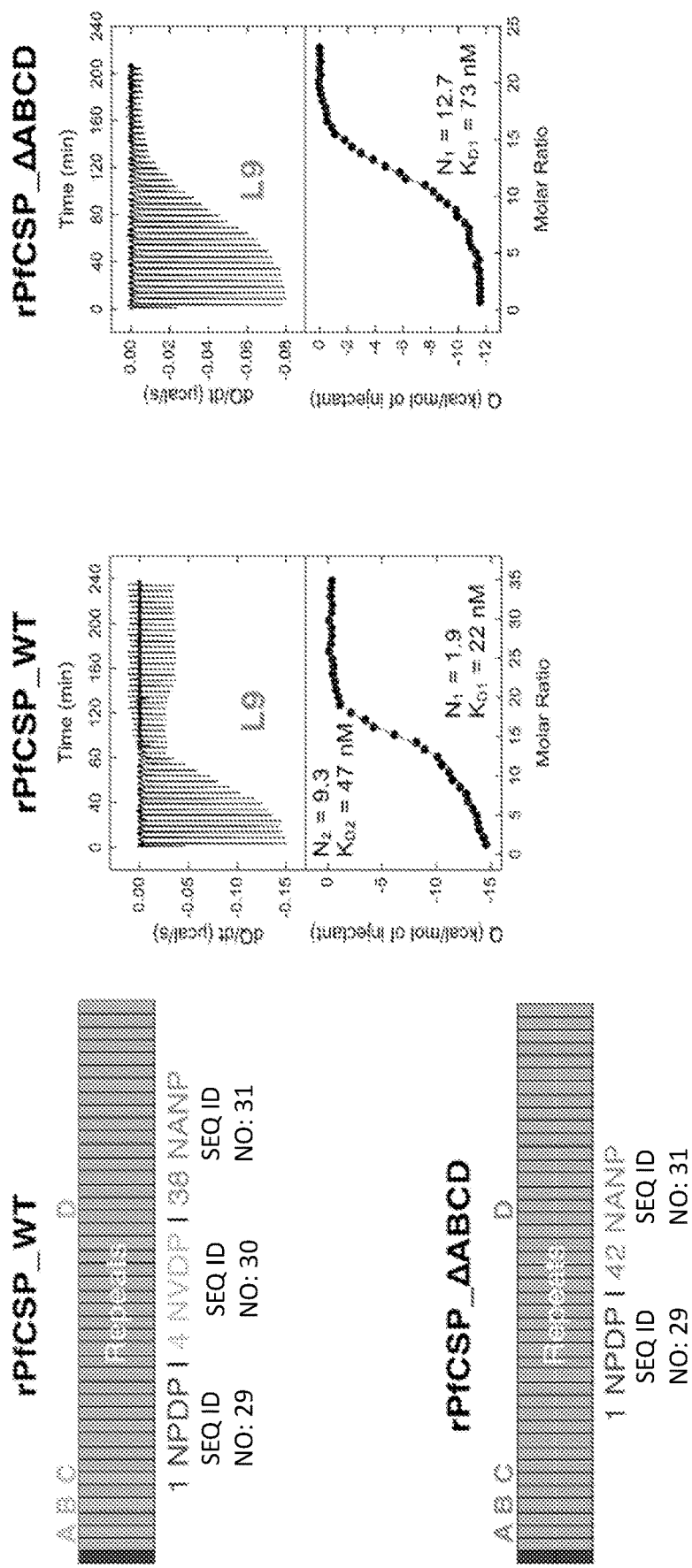

Remarkably, L9 IgG also showed two high-affinity binding events to rPfCSP: the first event involved ~2 binding sites (dissociation constant $K_{D1}$=22 nM) and the second event involved ~9 binding sites ($K_{D2}$=47 nM) (FIG. 3A). Based on L9's preference for NPNV (SEQ ID NO: 32), whether the first binding event was specific for this motif was assessed. The four NVDP (SEQ ID NO: 30) repeats found in rPfCSP (denoted A, B, C, D; FIG. 3A) were mutated to NANP (SEQ ID NO: 31) in all possible combinations. L9 binding was reduced to a single event only when all four NVDP (SEQ ID NO: 30) were mutated to NANP (SEQ ID NO: 31) (rPfCSP_ΔABCD), suggesting that the first high-affinity binding step requires at least one NPNV (SEQ ID NO: 32) (FIG. 3A). Furthermore, the affinity of L9 for ΔABCD decreased 3-fold compared to WT ($K_{D1}$=73 nM vs. $K_{D1}$=22 nM, respectively); however, the total binding stoichiometry (N) was not appreciably different (N=12.7 vs. N=11.2). L9 demonstrated two-step binding, as well as similar affinity and stoichiometry, for all other NVDP (SEQ ID NO: 30) mutants. As controls, the affinity and stoichiometry of mAb10 and 317 for ΔABCD were similar, suggesting that mutating all NVDP (SEQ ID NO: 30) to NANP (SEQ ID NO: 31) repeats in rPfCSP did not significantly alter the binding of these NPNA (SEQ ID NO: 38)-preferring mAbs.

Having demonstrated that L9 can two-step bind rPfCSP with high affinity as long as one NPNV (SEQ ID NO: 32) is present, we assessed the conservation of this epitope and NVDP (SEQ ID NO: 30) repeats in a large number of *P. falciparum* field strains. While there was considerable variation in both the number and position of NVDP (SEQ ID NO: 30) repeats, 100% of the 143 distinct *P. falciparum* strains contained at least one NVDP (SEQ ID NO: 30) and every NVDP (SEQ ID NO: 30) was preceded by an NANP (SEQ ID NO: 31) or ANP sequence that would give rise to NPNV (SEQ ID NO: 32). Furthermore, most (34 of 39, 87%) African strains contained 4 NVDP (SEQ ID NO: 30) repeats, similar to the 3D7 reference strain. These data show that the NPNV (SEQ ID NO: 32) epitope recognized by L9 is highly conserved, suggesting that L9 could react broadly with circulating field strains.

Figure 3B:
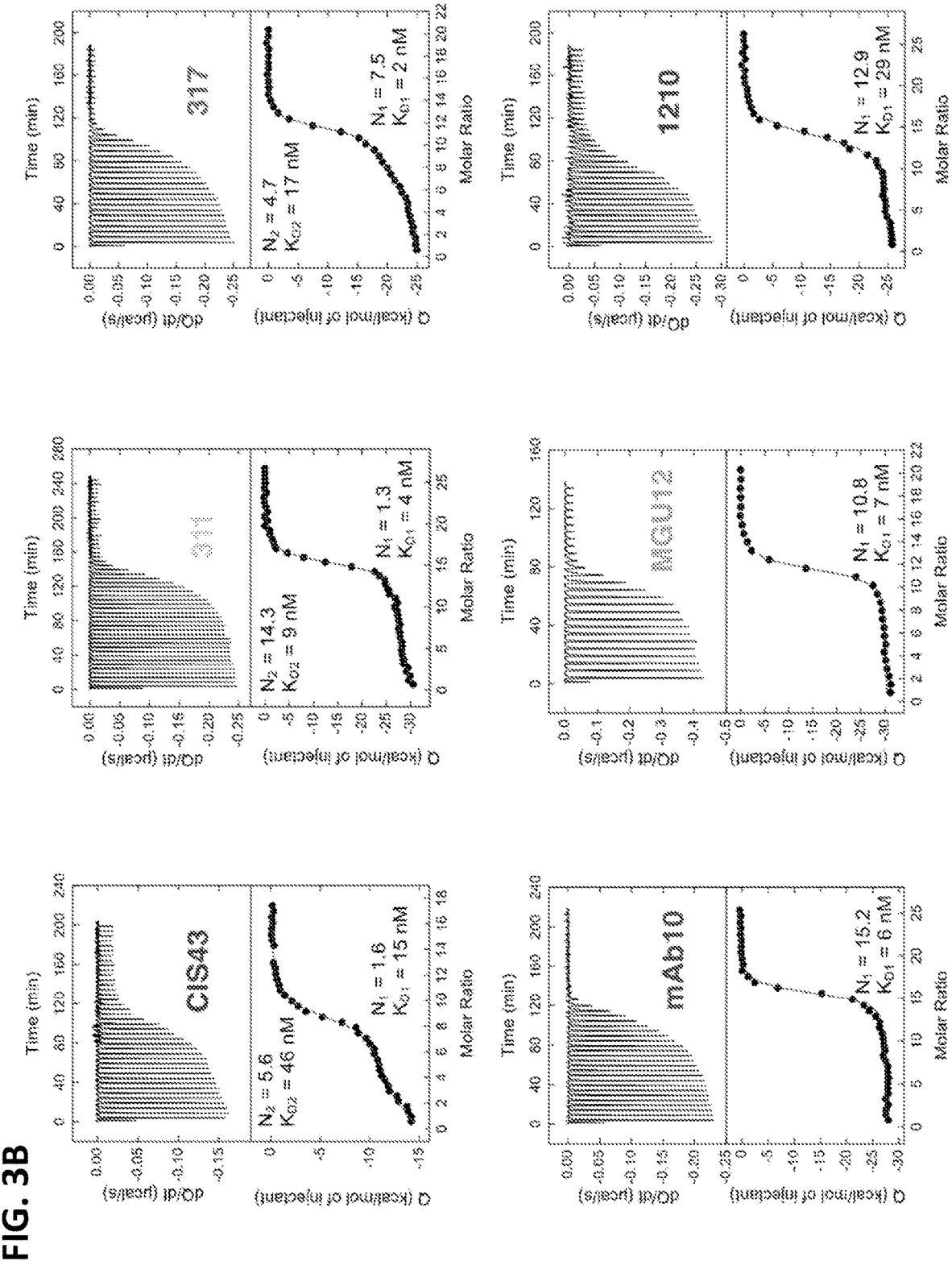

Next, the binding affinity and stoichiometry of mAb10, MGU12, 1210, 311, and 317 to rPfCSP was also determined. All mAbs bound rPfCSP with high affinity ($K_{D1}$=2-29 nM) and stoichiometry (~7-15 binding sites) (FIG. 3B). Interestingly, 311 and 317 also exhibited two-step binding to rPfCSP while 1210, mAb10, and MGU12 bound in a single step.

Figure 3D:
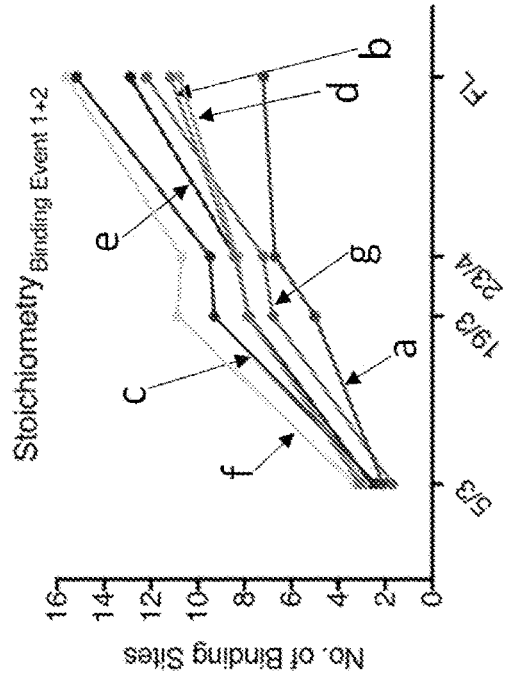

To further define the stoichiometry and affinity of the mAb panel, ITC was performed using three rPfCSP constructs with identical N- and C-termini but truncated repeat regions containing 23/4, 19/3, and 5/3 NANP/NVDP (SEQ ID NO: 31/SEQ ID NO: 30) repeats (FIG. 3C). The increase in stoichiometry for all mAbs was approximately linear as the number of repeats was increased except for CIS43, which showed no appreciable binding to the last 15 NPNA (SEQ ID NO: 38) repeats (FIG. 3D), consistent with its lower total stoichiometry (N=7.2 for FL; FIG. 3B). This suggests that the binding of every mAb tested except CIS43 is evenly distributed across the repeat region.

Figure 3E:
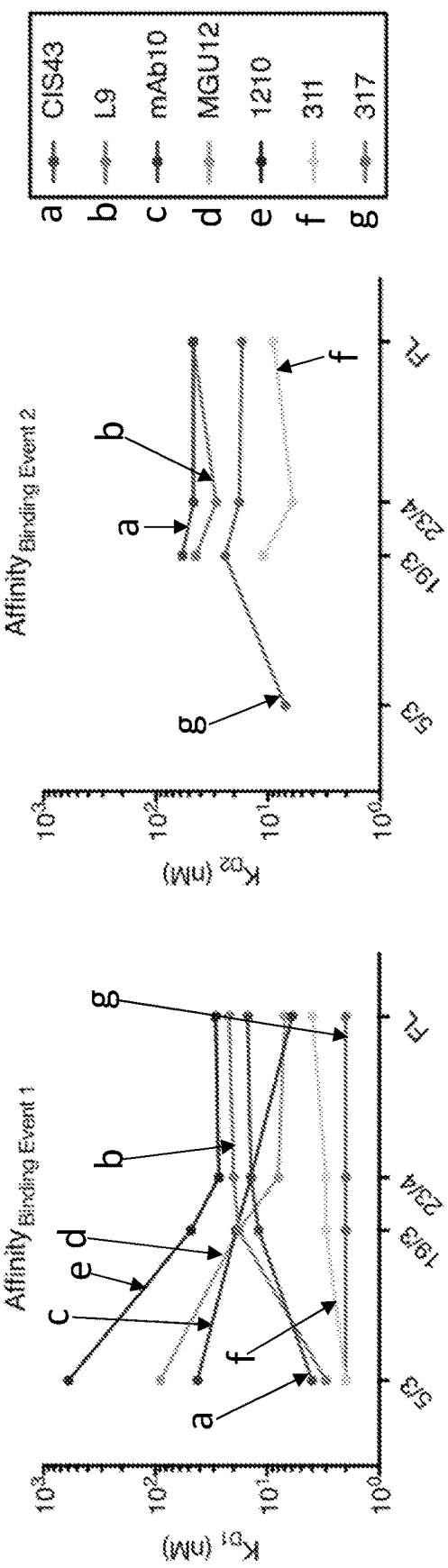

Notably, the stoichiometry of binding event 1 ($N_1$) for CIS43, L9, and 311 was relatively unchanged as the repeat region was truncated, suggesting that the epitopes recognized by these mAbs in binding event 1 are located within rPfCSP_5/3. As the repeats were truncated down to 5/3, the $K_{D1}$ of two-step binding mAbs (CIS43, L9, 311, 317) improved or was unchanged, while the $K_{D1}$ of single-step binding mAbs (mAb10, MGU12, 1210) worsened (FIG. 3E). Interestingly, only 317 maintained two-step binding to rPfCSP_5/3 and had a measurable $K_{D2}$. Overall, these data suggest that the epitope(s) bound by the two-step binding mAbs in binding event 1 are located in the junctional region encompassed by rPfCSP_5/3 and that two-step binding is associated with high-affinity binding to 5/3.

Liver Burden Reduction Mediated by a Panel of Neutralizing Human PfCSP mAbs

Figure 4A:
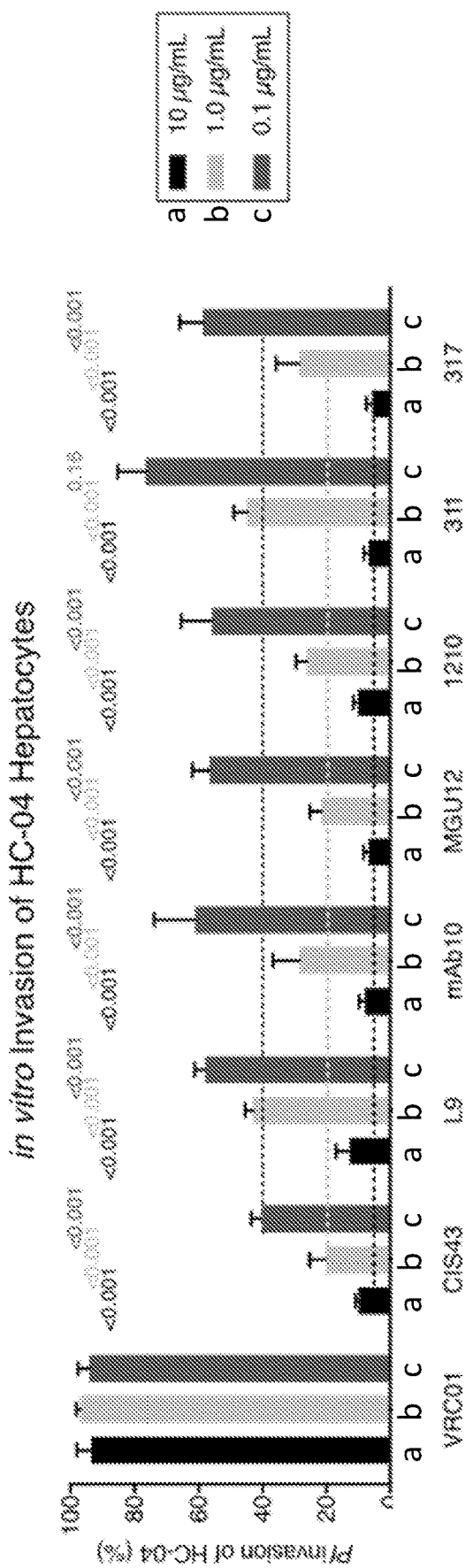
FIGS. 4A and 4B. Comparison of in vitro and in vivo assays to assess functional activity of human PfCSP mAbs in the liver.
Figure 4B:
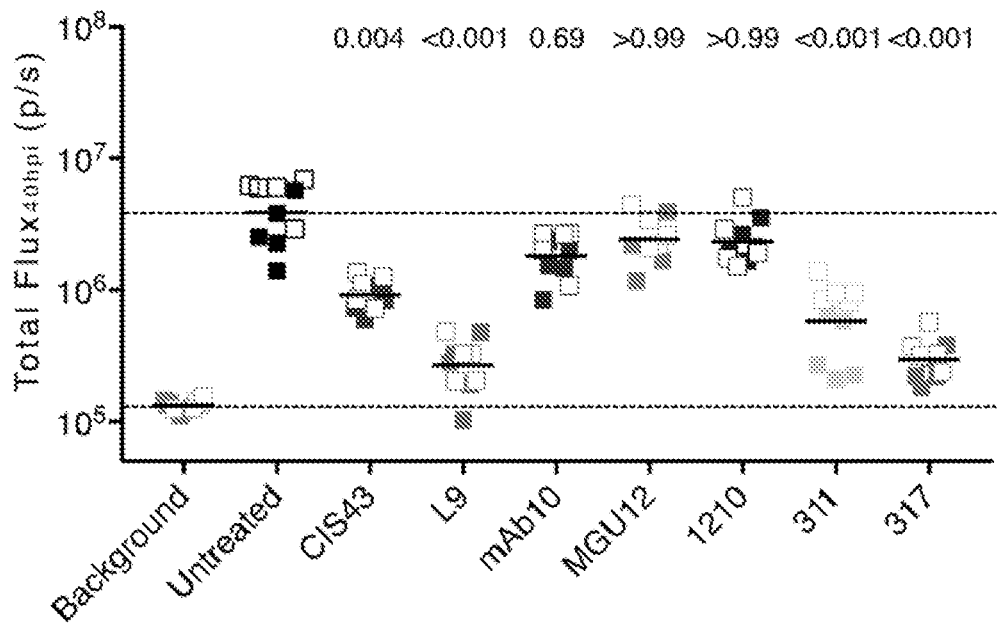
Figure 4B:
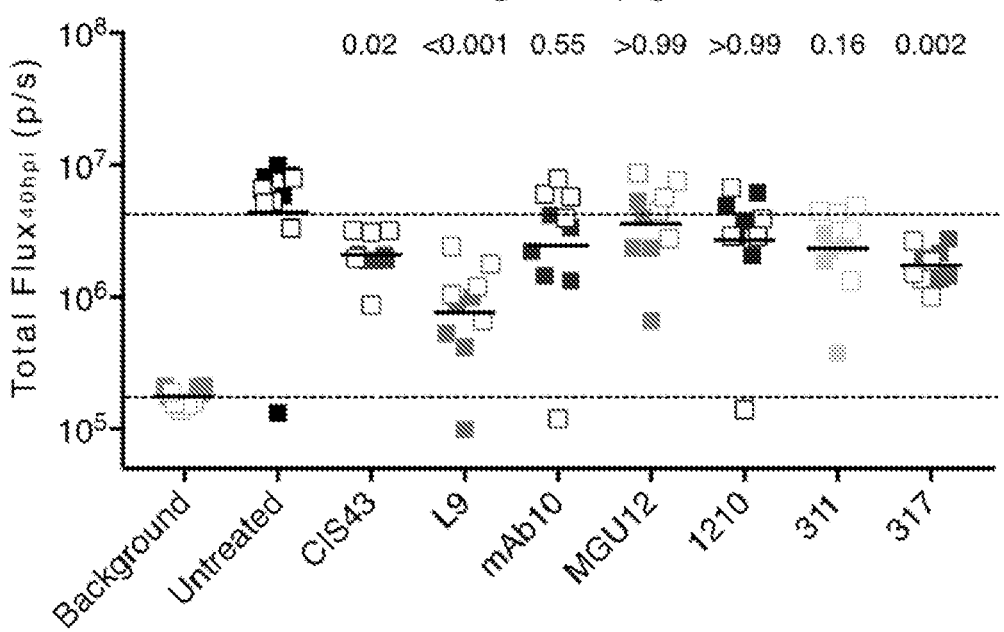

The ability of the mAbs in the panel to neutralize SPZ in vitro and in vivo before they can reach their final destination in the the liver and infect hepatocytes was compared. First, the mAbs' capacities to inhibit *P. falciparum* invasion of HC-04 hepatocytes was determined, an in vitro assay commonly used to screen for neutralizing PfCSP mAbs (Scally et al. J. Exp. Med. 215, 63-75, 2018; Triller et al Immunity 47, 1197-1209.e10, 2017). Here, all mAbs were comparable (except for 311 at 0.1 μg/mL) in their ability to significantly reduce invasion relative to the control antibody (FIG. 4). Next, the ability of limiting mAb doses to mediate in vivo protection against IV challenge with Pb-PfCSP in mice, which is effectively a liver challenge as intravenously inoculated SPZ invade hepatocytes within 2 minutes, was assessed (Shin et al. J. Protozool. 29, 448-454, 1982). At 75 μg/mouse, CIS43, L9, 311, and 317 significantly reduced liver burden compared to untreated controls; reduction by mAb10, MGU12, and 1210 did not reach statistical significance. At 25 μg/mouse, only CIS43, L9, and 317 significantly reduced liver burden, with the reduction by L9 being the most statistically significant (FIG. 4b).

These data clearly demonstrate that CIS43, L9, 311, and 317 mediated the greatest liver burden reduction following IV challenge. When considered alongside the ITC data (FIGS. 3D-3E), these data suggest that two-step binding to rPfCSP and high-affinity binding to rPfCPS_5/3 are characteristics shared by the most protective mAbs against IV challenge (CIS43, L9, 311, and 317) and that high-affinity, multivalent binding to rPfCSP_FL (as observed with mAb10, MGU12, and 1210) did not predict in vivo protection at limiting doses. Furthermore, the in vitro hepatocyte invasion assay did not predict in vivo protection, in agreement with a previous report (Kisalu et al. Nat. Med. 24, 408-416, 2018).

Mechanisms that Human PfCSP mAbs use to Neutralize SPZ in the Liver

Figure 5A:
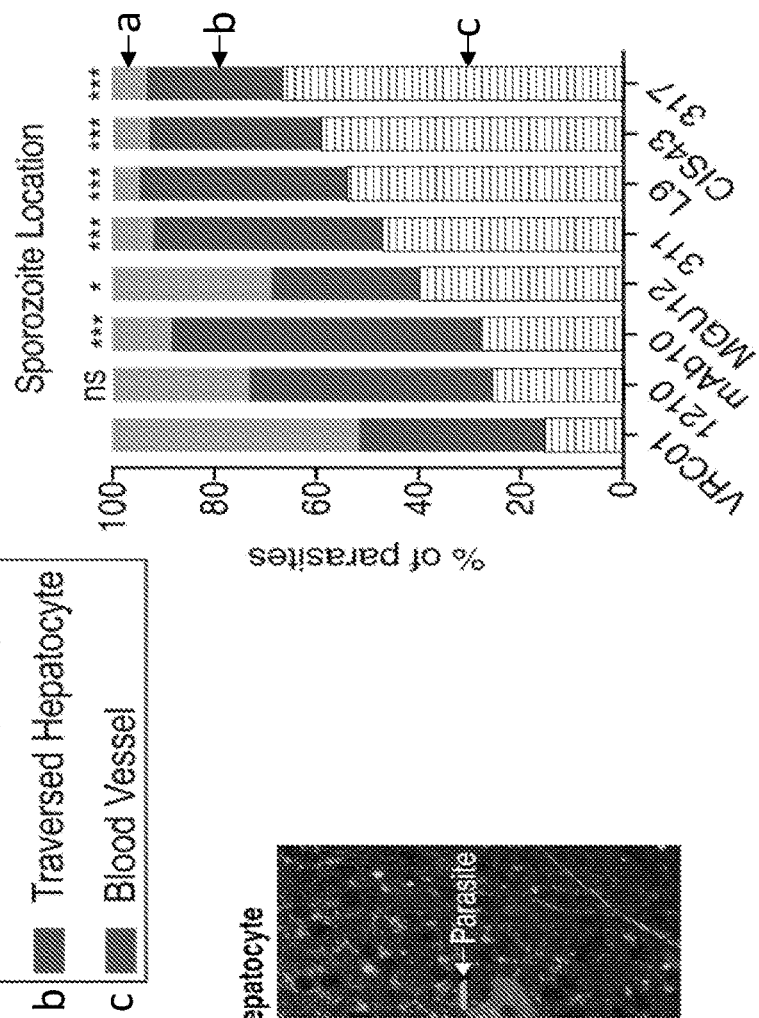

To determine the potential in vivo mechanisms contributing to the differences in liver burden reduction meditated by the mAbs in the panel, an intravital imaging assay was developed to quantify SPZ locations and morphologies in the liver immediately following IV inoculation of Alexa Fluor 405-labeled mAbs, Pb-PfCSP expressing GFP, and rhodamine-labeled dextran. Pb-PfCSP were visualized by multiphoton microscopy as they exited liver sinusoids and traversed hepatocytes before infecting a hepatocyte (FIG. 5A). Importantly, complete prevention of hepatocyte infection in these studies is not expected due to the high SPZ inoculum required for imaging.

Figure 5B:
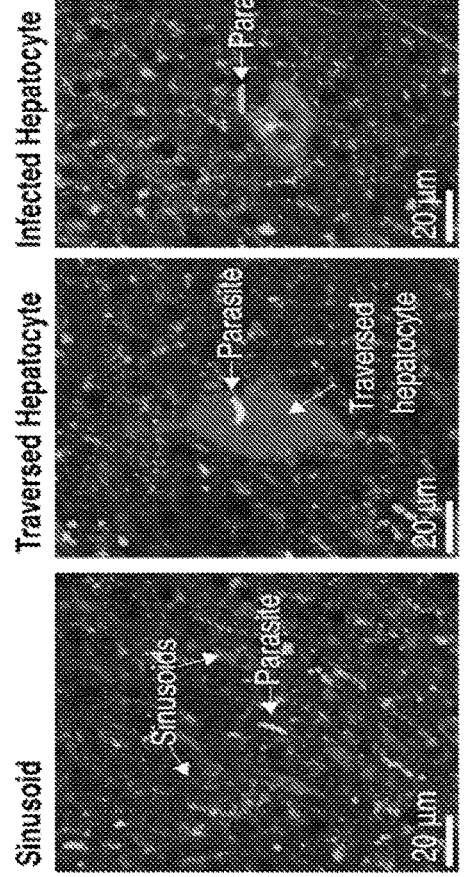
Figure 5D:
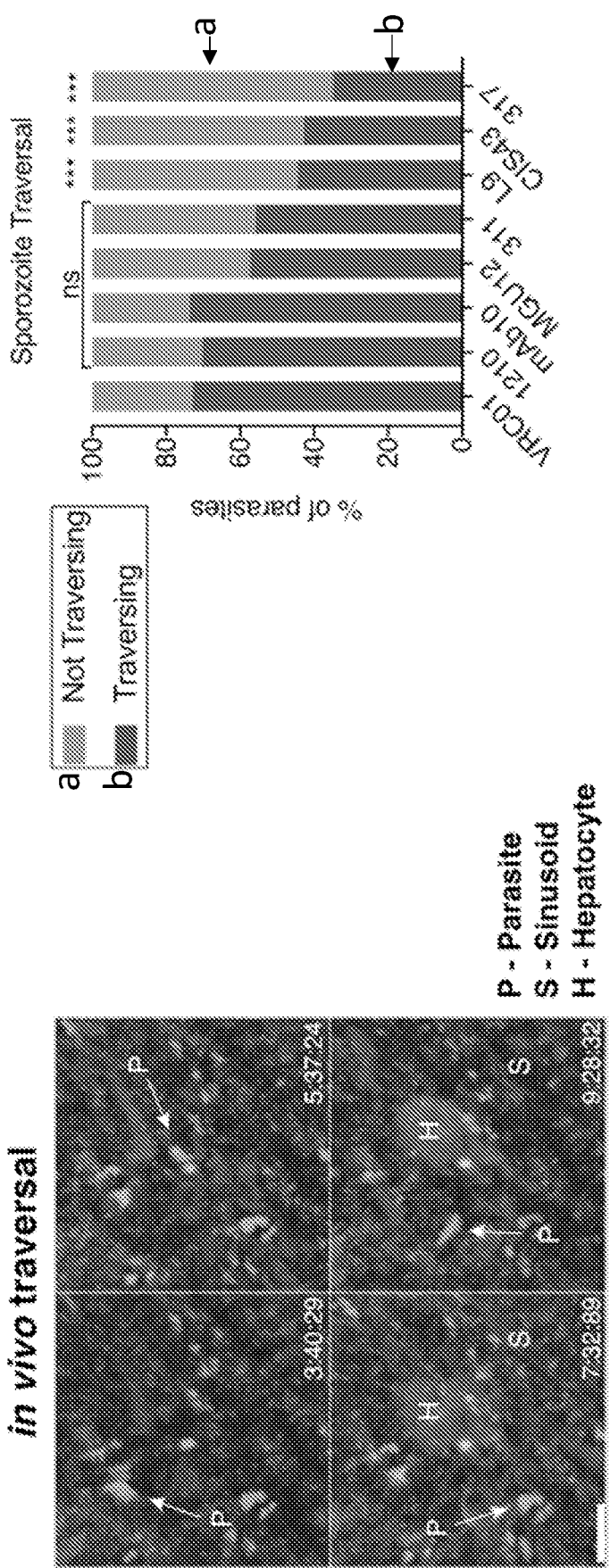
Figure 9A:
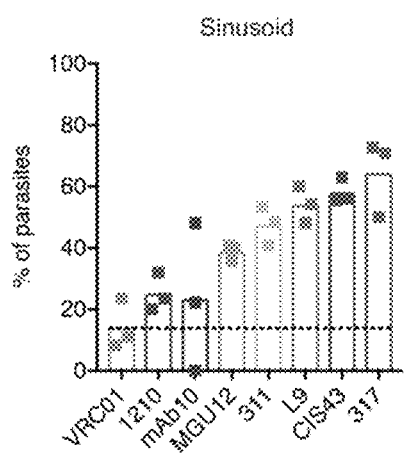
FIGS. 9A-9E. Individual liver intravital imaging experiments and cytotoxic bursting of Pb-PfCSP SPZ in vivo.
Figure 9B:
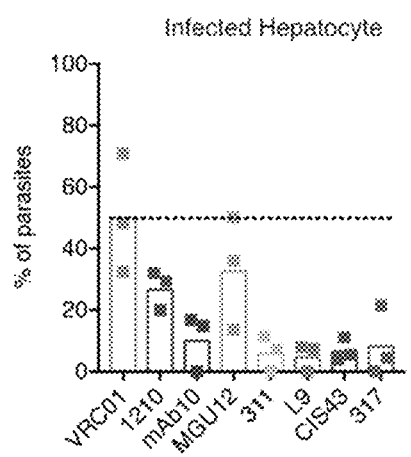
Figure 9C:
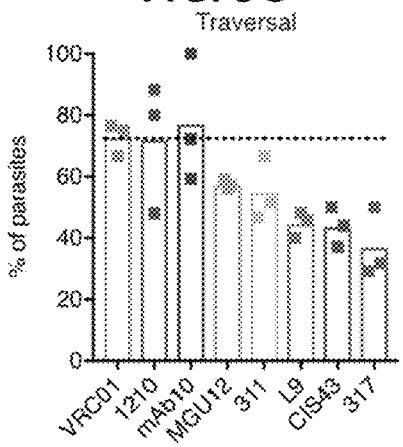
Figure 9D:
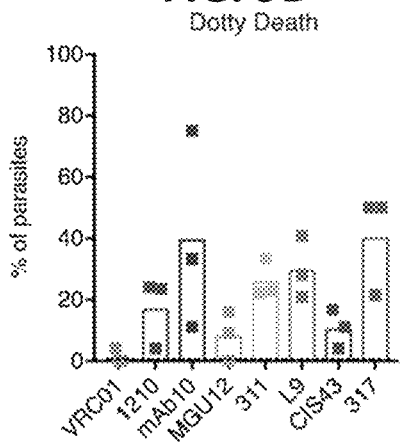

Consistent with the differences in protection mediated by the mAbs against IV challenge (FIG. 4B), mice that received 311, L9, CIS43, and 317 had the highest percentages (47-67%) of Pb-PfCSP in the sinusoids and the lowest percentage (5-8%) of Pb-PfCSP infecting hepatocytes (FIG. 5B and FIGS. 9A-9B). Furthermore, traversal of hepatocytes was detected by the uptake of rhodamine-labeled dextran from sinusoids into hepatocytes with compromised membranes (FIG. 5C, FIG. 9C) (Mota et al. Science 291, 141-144, 2001; Yang et al. Cell Rep 18, 3105-3116, 2017). Only L9, CIS43, and 317 significantly prevented Pb-PfCSP from traversing >1 hepatocyte (35-45% traversing versus 73% in control), while 311 trended towards traversal inhibition (P=0.07) (FIG. 5D). Collectively, these data show that the four most protective mAbs against IV challenge (CIS43, L9, 311, 317) limit hepatocyte infection by preventing Pb-PfCSP egress from sinusoids and subsequent traversal of hepatocytes.

Figure 5G:
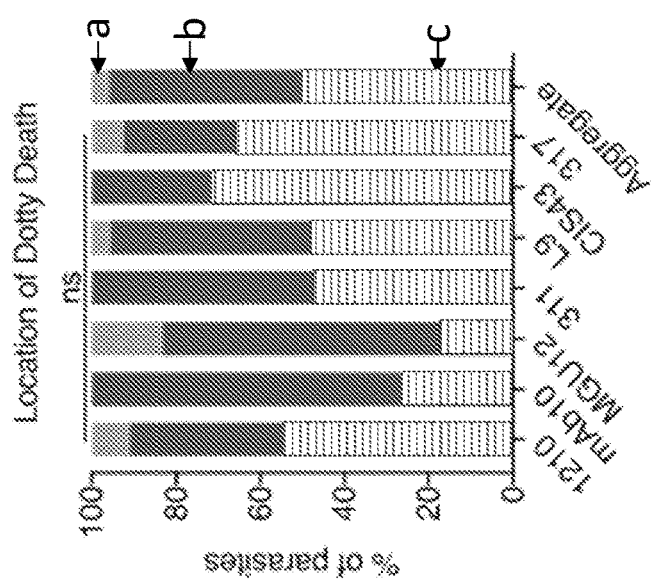
Figure 5F:
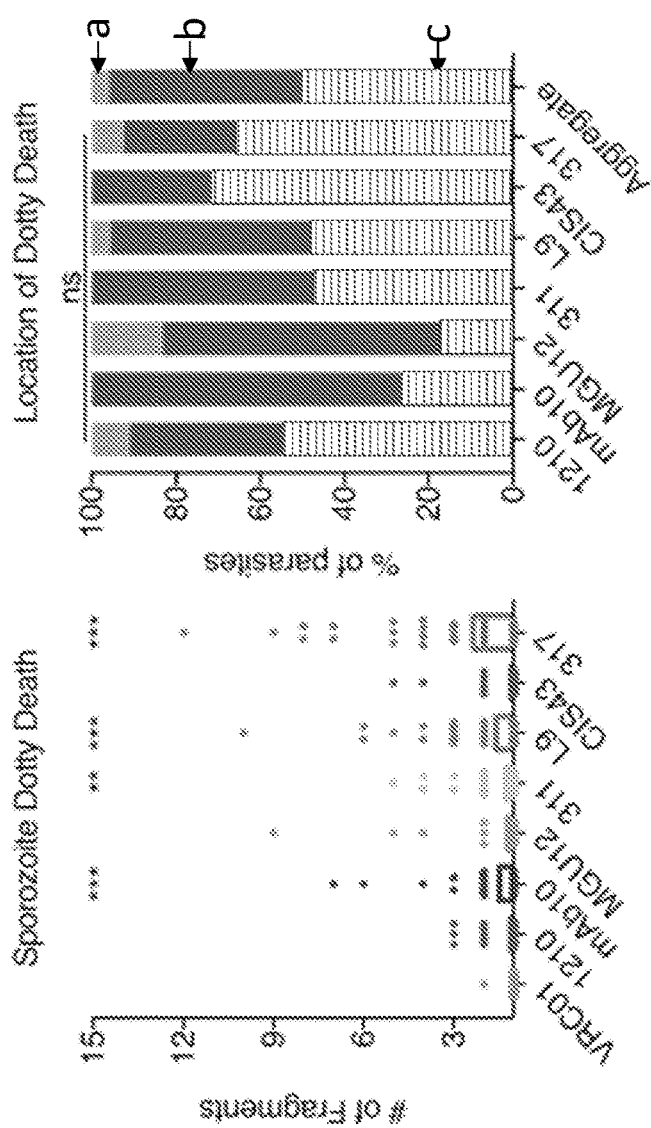
Figure 5E:
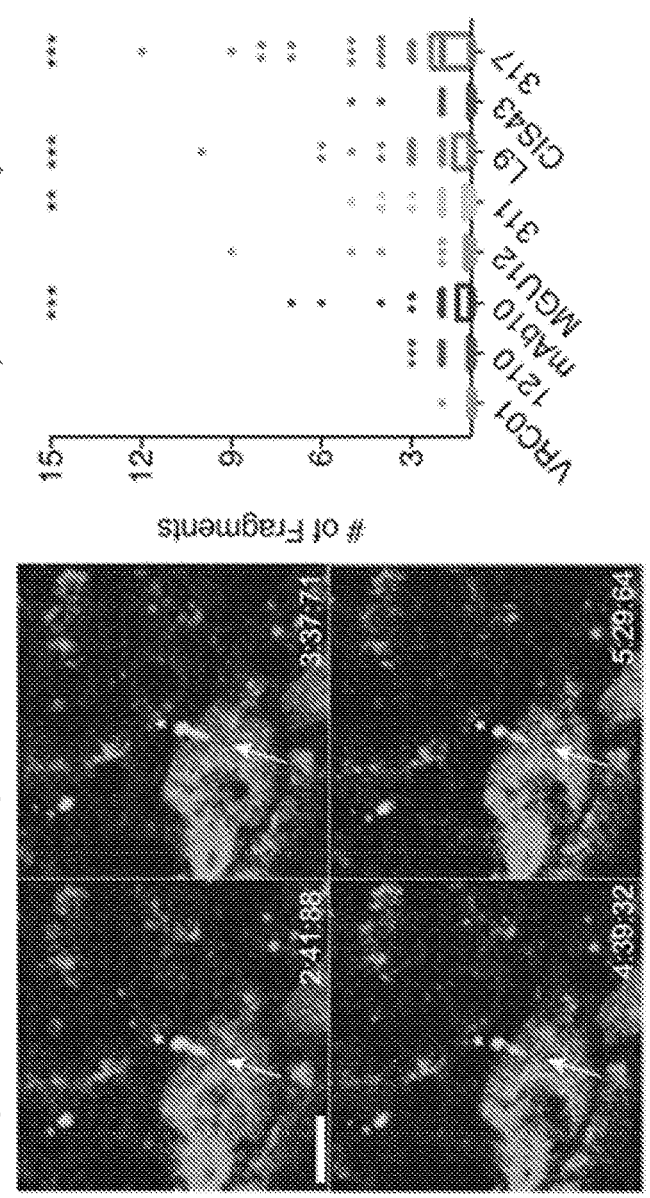
Figure 9E:
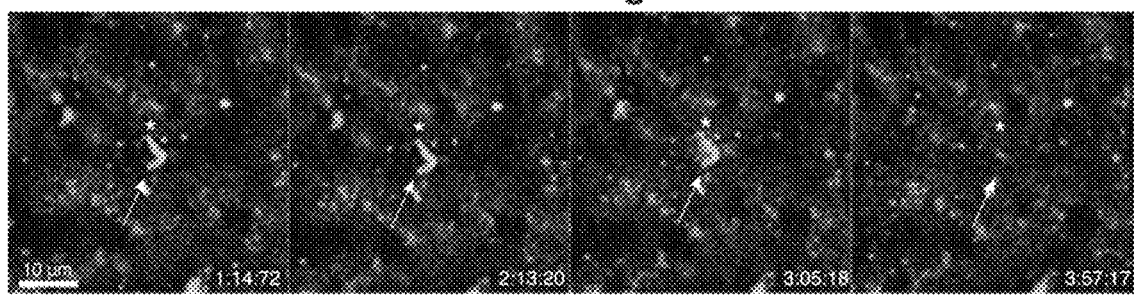

Anti-CSP repeat antibodies have been shown to directly kill SPZ in vitro and in the skin in a process called "dotty death," which manifests as the gradual disappearance of parasite GFP sometimes accompanied by a persistent fluorescent dot at the parasite's posterior pole (Aliprandini et al. Nat Microbiol 3, 1224-1233, 2018). Since no studies have assessed whether this cytotoxic process occurs in the liver, we examined whether the mAbs in the panel induced dotty death of SPZ in the liver (FIG. 5E). Only 317, L9, mAb10, and 311 significantly induced dotty death (FIG. 5F). Pb-PfCSP mostly underwent dotty death while migrating through sinusoids and traversing hepatocytes (50% and 46%, respectively) and rarely after invading hepatocytes (4%) (FIG. 5G). Interestingly, a cytotoxic phenomenon distinct from dotty death was also observed wherein immobilized, mAb-bound Pb-PfCSP rapidly lost membrane integrity and burst, releasing GFP into the surrounding tissue (FIG. 9E). This "bursting" was a rare event and only observed with 317 and L9. Collectively, these data demonstrate that PfCSP mAbs can directly induce the cytotoxic death of SPZ in the liver and substantiate that most mAb-mediated neutralization of SPZ occurs prior to hepatocyte invasion.

Figure 6A:
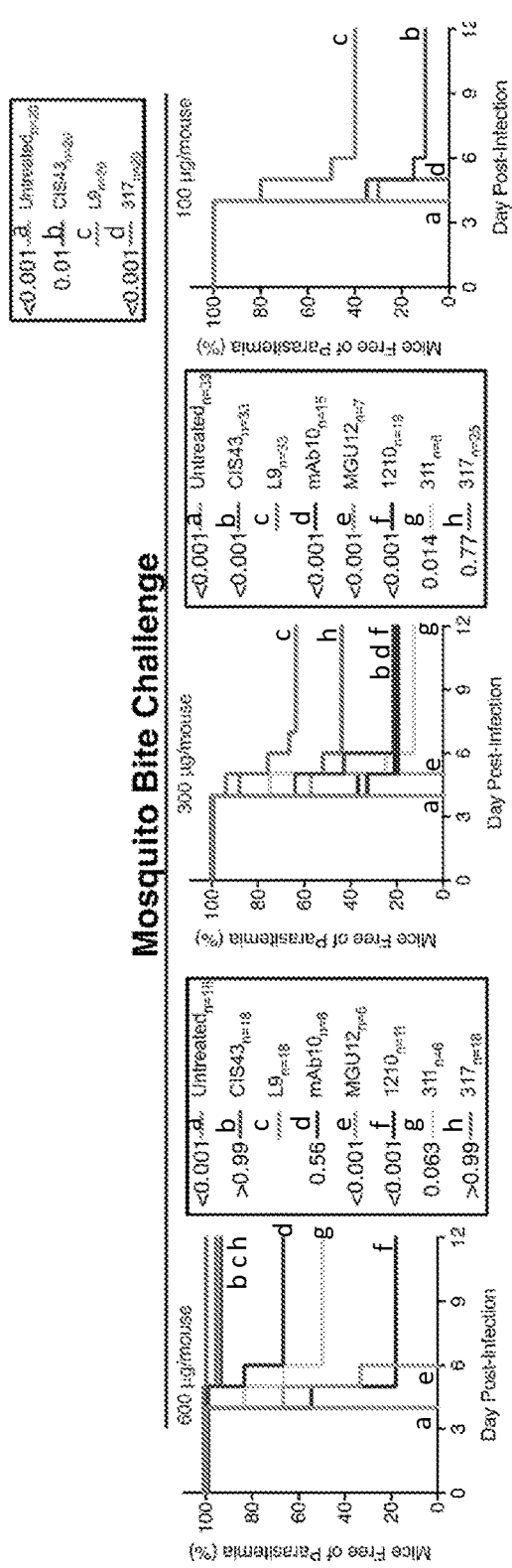
FIGS. 6A-6F. Protection against mosquito bite challenge mediated by seven neutralizing human PfCSP mAbs.
Figure 6B:
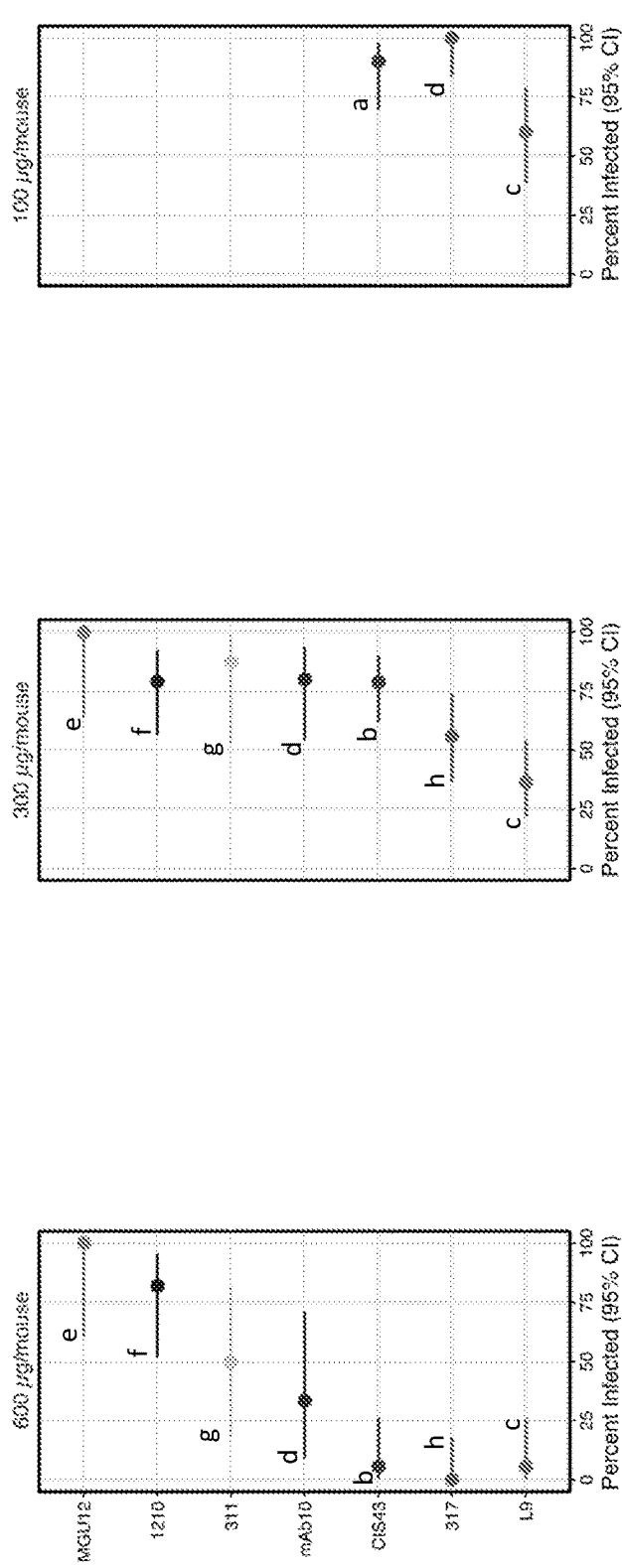

L9 is More Protective Against Mosquito Bite Challenge than a Panel of Human PfCSP mAbs The gold standard for assessing the in vivo functional activity of anti-SPZ mAbs are natural transmission studies wherein mice are challenged with infected mosquito bites (Imkeller et al. Science 360, 1358-1362, 2018; Tan et al. Nat. Med. 24, 401-407, 2018; Kisalu et al. Nat. Med. 24, 408-416, 2018; Seder et al. Science 341, 1359-1365, 2013). Thus, L9 was compared to the other mAbs in the panel in multiple independent mosquito bite challenge studies performed across several doses to establish a fully protective dose and then determine potency at more limiting doses (FIGS. 6A-6B). Importantly, all studies were completed in a blinded manner. At 600 µg/mouse, protection by L9 (94%) was comparable to 317 (100%) and CIS43 (94%), trended higher than mAb10 (67%) and 311 (50%), and was significantly greater than 1210 (18%) and MGU12 (0%). At 300 µg/mouse, protection by L9 (64%) trended higher than 317 (44%) and was significantly greater than CIS43, mAb10, 1210 (~20%), 311 (13%), and MGU12 (0%). At 100 µg/mouse, L9 (40%) was significantly more protective than CIS43 (10%) and 317 (0%).

Figure 6C:
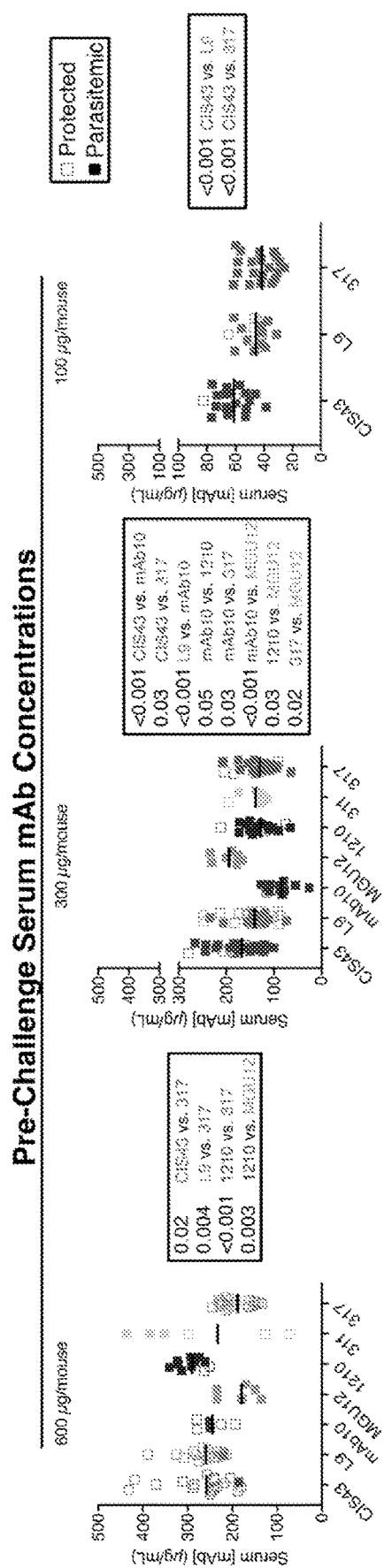

To determine whether differences in mAb concentrations prior to challenge may have contributed to differences in protection, serum mAb titers were measured one day prior to challenge in all mice that underwent mosquito bite challenge (FIG. 6C). Notably, L9 titers were similar to 317 at the lower doses of 300 and 100 µg/mouse despite providing improved protection. Furthermore, mAb10 titers (~85 µg/mL) were significantly lower than the other mAbs at the 300 µg/mouse dose.

Figure 6D:
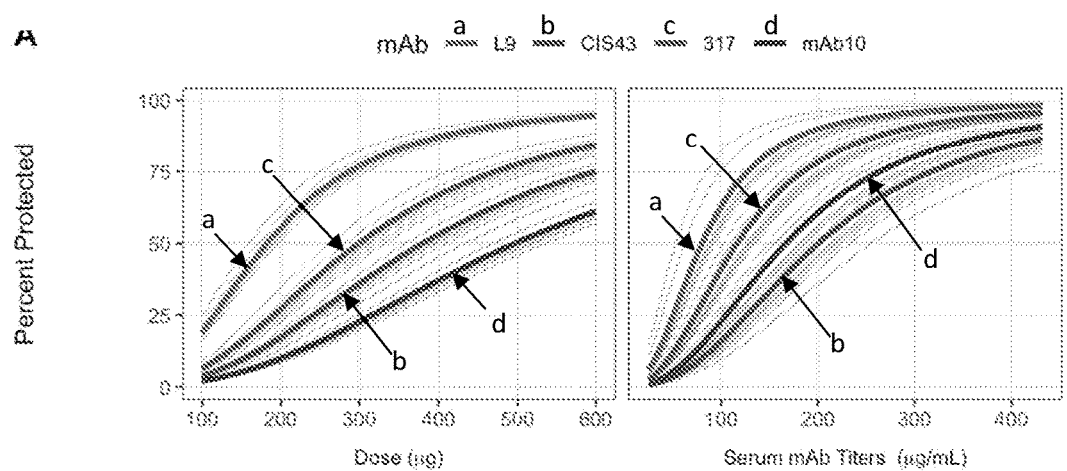

Based on the protection and titers data (FIGS. 6A-6C), a dose-response curve was generated using a 2-parameter logistic (2PL) regression model (FIG. 6D) and two methods were utilized to compare the mAbs protection against mosquito bite challenge across all doses: (1) the mAbs' $ID_{50}$ (dose required for 50% inhibition) and $IC_{50}$ (serum concentration required for 50% inhibition) values; and (2) testing for a significant odds ratio (OR) between mAbs. MGU12, 1210, and 311 were excluded from this analysis as MGU12 elicited no protection at every dose tested while 311 and 1210 elicited ≤50% protection at the highest dose of 600 µg/mouse (i.e., ID50>50%).

Figure 6E:
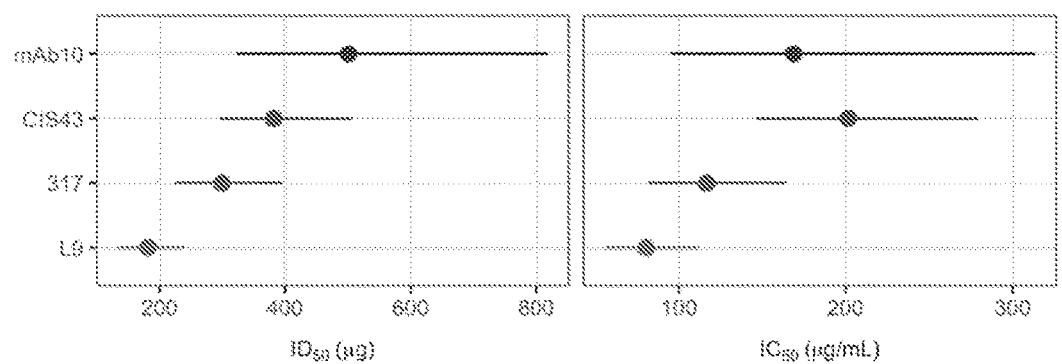
Figure 6F:
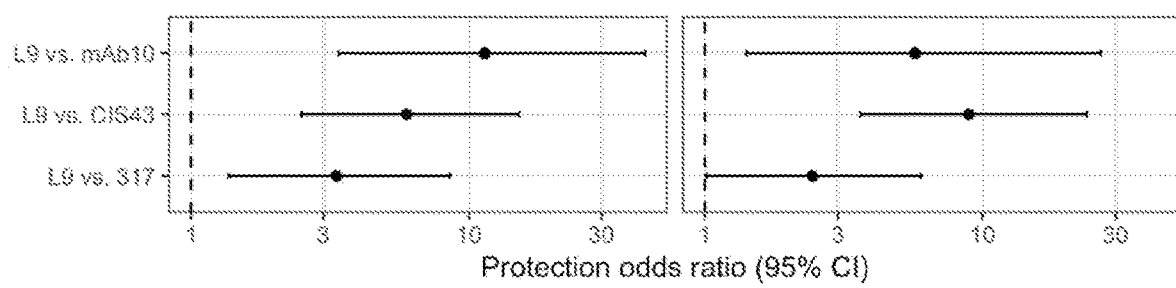

The superior protective potency of L9 compared to the other mAbs in the panel was demonstrated by its improved protection across all doses and serum mAb titers (FIG. 6D) and its lowest $ID_{50}$ and $IC_{50}$ values (181.6 µg and 80.3 µg/mL, respectively) (FIG. 6E). Furthermore, the odds of L9-treated mice being protected from mosquito bite challenge were significantly higher than all other Abs except for 317 (FIG. 6F). For L9 versus 317, the protection OR was significantly greater for dose (OR=3.33; P=0.028) and trended favorably for serum mAb titers (OR=2.43; P=0.05). mAb10 had a higher $ID_{50}$ but lower $IC_{50}$ than CIS43, likely due to its poorer PK (FIG. 6C), suggesting that mAb10 might be more potent than CIS43. Collectively, these data demonstrate that L9 is as or more potently protective than all mAbs in the panel against mosquito bite challenge.

Discussion

This is the first study describing a highly protective human mAb that preferentially binds the NPNV (SEQ ID NO: 32) motif associated with NVDP (SEQ ID NO: 30) minor repeats of PfCSP. The unique preference of L9 for NPNV (SEQ ID NO: 32) motifs is further underscored by the observation that every NVDP (SEQ ID NO: 30) had to be mutated to NANP (SEQ ID NO: 31) to prevent two-step binding of L9 to rPfCSP (FIG. 3A). The demonstration that L9 maintains high-affinity binding to rPfCSP as long as one NVDP (SEQ ID NO: 30) is present suggests that L9 should bind all circulating strains, as 100% of P. falciparum field strains have >1 NVDP (SEQ ID NO: 30).

Figure 8C:
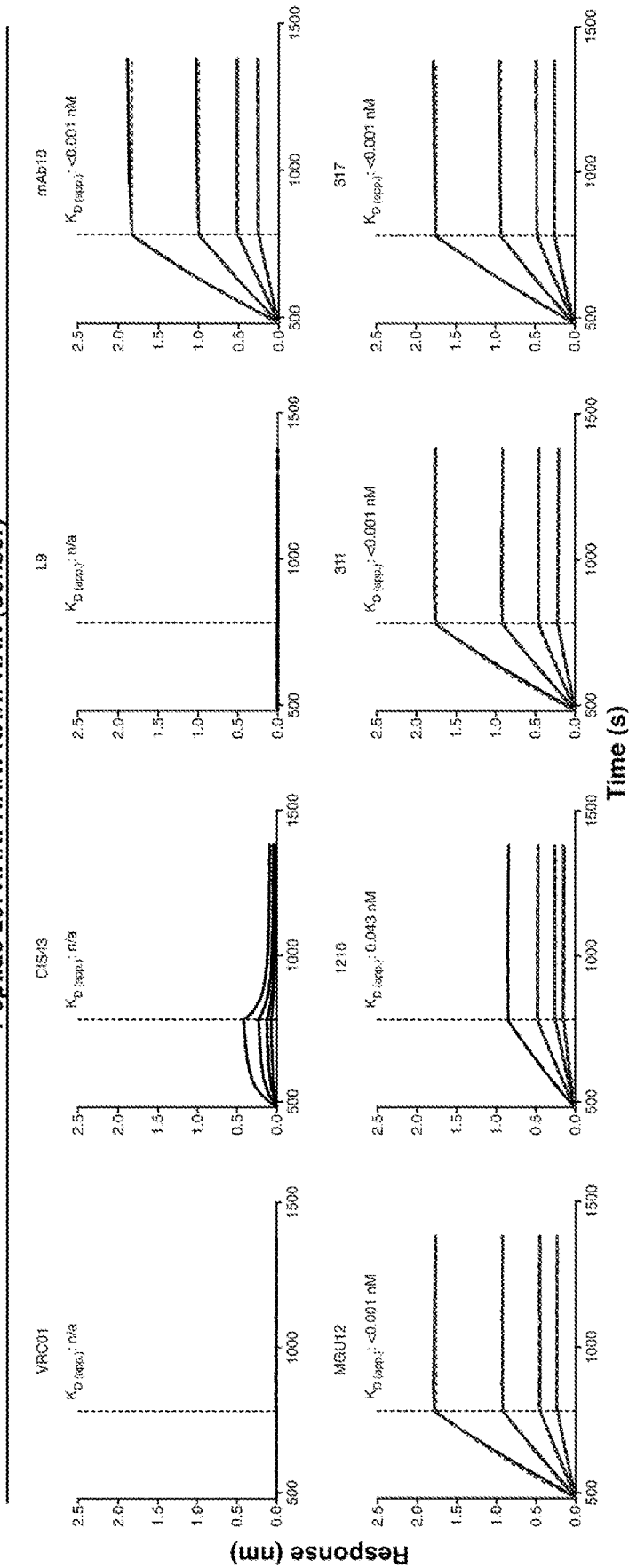

While PfCSP repeat mAbs preferentially target either DPNA/NPNV/NPNA (SEQ ID NO: 37/SEQ ID NO: 32/SEQ ID NO: 38), they can promiscuously bind peptides composed of all three tetrapeptide repeats due to paratopes that accommodate the subtle differences between these motifs. For example, while MGU12 was reported to have dual specificity for the junctional epitope and NPNA (SEQ ID NO: 38) repeats (Tan et al. Nat. Med. 24, 401-407, 2018), the peptide competition and BLI data (FIG. 2 and FIG. 8) show that MGU12 is an NPNA (SEQ ID NO: 38)-preferring mAb with lower affinity for the junctional epitope. Similarly, a recent study reported two new dual-specific mAbs called 667 and 668 that demonstrated some affinity (12 μM and 206 nM, respectively) for a junctional peptide KQPADGNPDPNANPNV, but exhibited greater affinity for a pure NPNA (SEQ ID NO: 38)-containing peptide (176 nM and 55.6 nM, respectively) (Ogen et al. PLoS Pathog. 16, e1008373, 2020). Consistent with these and previous studies, the peptide mapping data provided herein classify mAb10, 1210, 311, and 317 as NPNA (SEQ ID NO: 38)-preferring mAbs that can bind DPNA (SEQ ID NO: 37)- and NPNV (SEQ ID NO: 32)-containing peptides, albeit with lower affinity. In contrast, CIS43 and L9 respectively exhibited 1.4E4- and ~2.5E6-fold greater preference for DPNA (SEQ ID NO: 37)-containing peptide 21 and NPNV (SEQ ID NO: 32)-containing peptide 22 than for NPNA (SEQ ID NO: 38)-containing peptide 29 (FIG. 2). Given their binding promiscuity, anti-repeat mAbs are more accurately classified based on their preferred peptide epitopes, which are optimally determined by competition ELISAs with short overlapping peptides across a range of concentrations to compete mAb binding to rPfCSP. However, the observation that the three most protective antibodies in this study (CIS43, L9, and 317) are respectively DPNA (SEQ ID NO: 37)-, NPNV (SEQ ID NO: 32)-, and NPNA (SEQ ID NO: 38)-preferring mAbs demonstrates that peptide preference does not ultimately predict in vivo protection and may only be useful for classification.

Remarkably, these three highly protective mAbs demonstrated two-step binding to rPfCSP_FL and high-affinity binding to rPfCSP_5/3 by ITC. This is likely due to the presence of all three types of tetrapeptides in the junctional region encompassed by rPfCSP_5/3. Interestingly, while CIS43 and L9 were cloned from subjects immunized with attenuated PfSPZ presenting full-length PfCSP, 317 was cloned from a subject immunized with RTS,S/AS01 (Oyen et al. Proc. Natl. Acad. Sci. U.S.A. 114, E10438-E10445, 2017), which does not include the junctional region in rPfCSP_5/3, underscoring the binding promiscuity of anti-repeat mAbs. Two-step binding was not previously observed in ITC studies of 317 binding to peptides (Oyen et al. Proc. Natl. Acad. Sci. U.S.A. 114, E10438-E10445, 2017), highlighting the additional utility of classifying mAbs based on their binding to full-length or truncated rPfCSP proteins.

The data presented here suggest that high-affinity, multivalent binding to rPfCSP_FL may be necessary, but is not sufficient, for potent neutralization of SPZ in vivo. For instance, the affinity and valency of MGU12 binding to rPfCSP_FL was comparable to L9 despite marked differences in protection in vivo. Therefore, mAb binding to rPfCSP_5/3 by ITC may provide a first step towards classifying and down-selecting protective PfCSP mAbs. Further structural studies using rPfCSP (FL and/or 5/3) and SPZ are needed to understand the relationship between affinity for the junctional region, two-step binding, and SPZ neutralization.

This study also provides the first in vivo evidence that human PfCSP mAbs mediate protection in the liver by directly killing SPZ before they invade hepatocytes and/or by preventing their egress from sinusoids and subsequent traversal of hepatocytes. While several studies have shown that anti-CSP antibodies prevent SPZ from traversing and invading hepatocytes in vitro and directly kill SPZ in the skin, the data presented here are the first demonstration of these effects in the liver in vivo. Importantly, in vitro hepatocyte assays (FIG. 4A) did not predict the relative protection mediated by the panel of mAbs against IV challenge (FIG. 4B) or mosquito bite challenge (FIG. 6A). A possible reason for this discrepancy is the lack of endothelium and other complex architecture in hepatocyte monolayers in vitro. Indeed, the finding that PfCSP mAbs prevent SPZ egress from sinusoids cannot be measured with current in vitro hepatocyte assays since the hepatocyte monolayers are not vascularized. Effective SPZ neutralization in the vasculature (e.g., in the liver sinusoids) may be critical to mediate sterile protection against mosquito bite challenge, as a low number of SPZ are directly inoculated into the vasculature when a mosquito bites and even a single SPZ that reaches the liver can initiate a symptomatic blood-stage infection. While the skin has been demonstrated as a major site for antibodies to neutralize SPZ, these data highlight the liver as an additional site for PfCSP mAbs to mediate protection.

In conclusion, these data identify the NPNV (SEQ ID NO: 38) repeat motif of PfCSP as the target of a highly potent human mAb and thus an epitope that might improve next-generation malaria vaccine immunogens. The demonstration that passive transfer of L9, CIS43, and 317 into mice can provide >90% sterile protection against mosquito bite challenge (FIG. 6) supports their testing for malaria prophylaxis in travelers, aid workers, or military personnel and usage in seasonal control or elimination campaigns. To this end, proof-of-concept Phase I studies assessing the safety, pharmacokinetics, and efficacy of L9 and CIS43 in preventing malaria infection are underway.

In conclusion, the discovery L9 potently neutralizes SPZ across the skin, vasculature, and liver supports the use of passively transfer of this mAb as a new modality for malaria prevention.

Materials and Methods

Study subjects and clinical specimens. Clinical specimens were derived from study subjects in the VRC 314 clinical trial (clinicaltrials.gov/; NCT02015091). Briefly, VRC 314 was a multi-institution, phase 1, open-label, dose-escalation trial with controlled human malaria infection (CHMI) that was designed to assess the safety, immunogenicity, and protective efficacy of the Sanaria PfSPZ Vaccine administered by intravenous or intramuscular injection. The Sanaria PfSPZ Vaccine is composed of radiation-attenuated, aseptic, purified, cryopreserved *Plasmodium falciparum* sporozoites derived from the NF54 strain (Seder et al., Science. 341, 1359-1365, 2013). Attention was focused on subjects in group 6 who received a total of three doses ($9.0 \times 10^5$ PfSPZs) of the PfSPZ vaccine intravenously at weeks 0, 8, and 16. Sera from protected subjects were screened for antibody titers against a structurally stabilized form of peptide mimicking the junctional epitope (termed S02). A subject whose sera demonstrated the highest reactivity against S02 at the week 20 timepoint, 4 weeks after the last immunization, was chosen for single B cell sorting and mAb isolation.

Production of recombinant PfCSP full-length, truncated, and repeat mutant constructs. The amino acid sequence of PfCSP in the 3D7 clone of the NF54 strain (PlasmoDB ID: PF3D7_0304600.1) was used to generate a codon-optimized synthetic gene for expression in mammalian cells (GenScript). The DNA construct corresponding to the full-length rPfCSP, in which the leader peptide residues 1-20 were replaced with a mammalian secretory signal peptide derived from the modified bovine prolactin (MDSKGSSQKGSRLLLLLVVSNLLLPQGVLA, SEQ ID NO: 33) and the glycosylphosphatidylinositol (GPI) anchor residues 376-397 were excluded, was cloned into a CMV/R-expression vector with a C-terminal AviTag, HRV3C-processing tag, and a 6× histidine tag. This construct (termed PfCSP_SAmut_C5S) encodes the N-terminal domain with four amino acid mutations (SAmut_C5S) that removed processing sites and prevented dimerization upon solubilization to increase yield and facilitate consistent analyses, the central domain consisting of 38 NANP tandem repeats interspersed with 4 NVDP repeats, and the C-terminal domain. Truncated (Oyen et al., Sci Adv. 4, eaau8529, 2018) and NVDP repeat mutant rPfCSP were created in the same expression vector with identical N- and C-termini to full-length CSP_SAmut_C5S, expressed through transient transfection in 293F cells (Thermo Fisher Scientific), and purified from culture supernatants through polyhistidine-tag affinity chromatography followed by size-exclusion chromatography (GE Healthcare). Monomer-containing fractions were pooled, concentrated, snap frozen, and stored at ~80° C.

rPfCSP and S02 probe generation. For tetramer probe generation, rPfCSP or S02 (PESSSNPDCNANPNVDPNEDLIKKCEKINVPTEEIKKEIEEKK, SEQ ID NO: 40) fused to the DsbC protein were first biotinylated and then conjugated to the fluorophore fluorescein isothiocyanate (FITC) and Brilliant™ Violet 605 (BV605), respectively. Biotinylation was performed using ligase Bir A (Avidity) at 30° C. for 4 hours prior to buffer exchange with 1×PBS (pH 7.4) over a 30-kDa Centricon Plus-70 Centrifugal Filter (Millipore) to remove excess free biotin. Biotinylated rPfCSP and S02 were fluorescently labeled through sequential addition of streptavidin conjugated to FITC (SA-FITC) or BV605 (SA-BV605) (BD Biosciences), respectively, in a 4:1 molar ratio.\

Isolation of PfCSP-specific memory B cells. Memory B cell-derived monoclonal antibodies that bound fluorescent probes of PfCSP and S02 were isolated from cryopreserved peripheral blood mononuclear cells (PBMCs) stained with the following panel: Aqua LIVE/DEAD (Thermo Fisher Scientific), rPfCSP-FITC and S02-BV605 tetramer probes, and antibodies against CD3-APC/Cy7 (BioLegend), CD8-V450 (BD Biosciences), CD14-BV785 (BioLegend), CD20-Ax700/PE (BioLegend), IgM-PE/Cy5 (BD Biosciences) and IgG-APC (BD Biosciences). Cells were sorted using a BD FACS Aria II instrument (BD Immunocytometry Systems), and flow cytometry data were analyzed using FlowJo software (Tree Star). PfCSP-reactive (rPfCSP$^+$ and/or S02$^+$) CD20$^+$CD3$^-$CD14$^-$ memory B cells were single-cell sorted into 96-well PCR plates containing lysis buffer (RNase OUT, 5× First Strand buffer, DTT, IgePAL, and water; Thermo Fisher Scientific).

Production of recombinant immunoglobulins. Immediately following single cell sorting and lysis of rPfCSP-specific memory B cells, all RNA transcripts were reverse transcribed to cDNA through RT-PCR (SuperScript III First-Strand Synthesis System; Thermo Fisher Scientific). Amplification of the genes encoding the variable regions of IgG or IgM heavy chains, as well as kappa or lambda light chains, was performed using a cocktail of primers followed by sequencing (ACGT) and cloning into the pVRC8400 huIgG1, pVRC8400 huIgK, or SBShuLambda expression vectors (GenScript) containing the relevant constant region. Sequence analysis was performed using The International Immunogenetics Information System (IMGT, imgt.org). Matched heavy and light chain constructs were co-transfected into Expi293 cells using the ExpiFectamine™ 293 Transfection Kit (Life Technologies) and cultures were incubated at 37° C., 8% $CO_2$ for 6 days. Supernatants were harvested and purified using rProtein A Sepharose Fast Flow resin (GE Healthcare) and buffer exchanged with 1×PBS (pH 7.4) before being concentrated using Amicon Centrifugal Filters (Millipore). Purified mAb concentrations were determined using a Nanodrop spectrophotometer. The sequences of CIS43[29], mAb10[29], MGU12[28], 1210[25], 311[18], and 317[18] were retrieved from PDB or GenBank and produced and purified as described above (See also, Kisalu et al. Nat. Med. 24, 408-416, 2018; Tan et al. Nat. Med. 24, 401-407, 2018; Imkeller et al. Science 360, 1358-1362, 2018; Oyen et al. Proc. Natl. Acad. Sci. U.S.A. 114, E10438-E10445, 2017).

Fluorescent antibody labeling. Antibodies were conjugated to Alexa 647 or Alexa 405 molecules using the SAIVI Alexa Fluor 647 Antibody Labeling Kit (ThermoFisher Scientific). Alexa 647 conjugations and purifications were performed according to the manufacturer's directions. For Alexa 405 labeling, Alexa Fluor 405 NHS ester (ThermoFisher Scientific) was mixed with each antibody at a 8:1 molar ratio for 1 hour at room temperature. The reaction was then purified over a SAIVI column, with fractions collected to determine the location of the conjugate. For all conjugation reactions, 15-50 µl of the degree-of-labeling (DOL) modifying reagent was added; resulting PfCSP mAb conjugates had DOL molar ratios between 1.4-2.2. For determination of concentration and DOL of Alexa 647 conjugates: absorbance correction factor=0.03; extinction coefficient ($\varepsilon$)=239,000; for Alexa 405 conjugates: absorbance correction factor=0.7; extinction coefficient ($\varepsilon$)=34,500. Prior to use, conjugate binding was compared to unlabeled mAbs by sporozoite flow cytometry and/or PfCSP ELISA to confirm binding was not dramatically altered.

ELISA for binding of mAbs to rPfCSP. Immulon 4HBX flat bottom microtiter plates (Thermo Fisher Scientific) were coated with 100 µl per well of antigen (1.0 µg/ml) in bicarbonate buffer overnight at 4° C. Coated plates were blocked with 200 µl of PBS+10% FBS for 2 h at room temperature, followed by incubation for 2 h at 37° C. with 100 µl of PfCSP monoclonal antibodies or control antibodies at varying concentrations ($5 \times 10^{-7}$-5.0 µg/ml, 10-fold serial dilutions). Plates were incubated with 100 µl/well of 0.1 µg/ml HRP-conjugated goat anti-human IgG antibody (Bethyl Laboratories). Plates were washed six times with PBS-Tween between each step. After a final wash, samples were incubated for 10 min with 1-Step Ultra TMB-ELISA Substrate (Thermo Fisher Scientific). The optical density was read at 450 nm after addition of stopping solution (2N sulfuric acid, 100 µl/well).

ELISA for binding of mAbs to NANP peptides. MSD Gold microtiter plates (Meso Scale Discovery) were blocked with PBS+5% BSA (20 µl/well). Blocked plates were coated with 10 µl/well of NANP biotinylated peptides (240 pmol, Genscript) in PBS+1% BSA for 1 h at room temperature. The coated plates were incubated for 2 h at room temperature with 10 µl of PfCSP or control mAbs at varying concentrations ($5 \times 10^{-7}$-5.0 µg/ml, 5-fold serial dilutions). Plates were then incubated with 10 µl/well of 1.0 µg/ml Sulfo-tag goat anti-human IgG antibody (Meso Scale Discovery) for 1 h at room temperature. Plates were washed six times with PBS-Tween between each step. After a final wash, 35 µl of 1×MSD Read T Buffer (Meso Scale Discovery) was added to each well and plates were analyzed on an MSD Sector Image 2400 instrument.

Epitope mapping and competitive binding ELISAs of PfCSP mAbs. Epitope mapping of CIS43 and L9 was performed using PfCSP overalapping peptides (peptides 20-61) that were 15 amino acids in length (GenScript) and overlapped by 11 residues spanning the central repeat region of PfCSP using the MSD U-Plex Assay platform (Meso Scale Delivery) according to the manufacturer's instructions, with all mAb concentrations at 0.01 µg/ml. Competitive ELISA was also performed using peptides 20-61. Briefly, ELISA plates were coated with 10 µl of rPfCSP (200 ng/ml) for 1 h at room temperature. After coating, PfCSP-specific monoclonal antibodies (10 ng/ml) preincubated overnight with varying concentrations (0-1,000 µg/ml) of selected PfCSP peptides in PBS+1% BSA were added to the rPfCSP-coated plates, and ELISA was performed on the MSD platform as described above. For the alanine scanning mutagenesis experiments, competitive ELISA was performed as described above using peptide 22 variants where each residue was mutated to an alanine or a serine if the original residue was an alanine (GenScript).

Kinetic binding assay using biolayer interferometry. Antibody binding kinetics were measured using biolayer interferometry on an Octet Red384 instrument (forteBio) using streptavidin-capture biosensors (forteBio). PfCSP mAb solutions were plated in black tilted-bottom 384-well microplates (fortéBio); assays were performed with agitation at 30° C. mAb serial concentrations used are as follow: 1.25, 0.625, 0.3125, and 0.15625 µg/ml. Loading of biotinylated peptides 21, peptide 22, and peptide 29 (GenScript) was performed for 300 s, followed by dipping of biosensors into buffer (PBS+1% BSA) for 60 s to assess baseline assay drift. Association with whole IgG (serially diluted from 16.67 to 1.04 µM) was done for 300 s, followed by a dissociation step in buffer for 600 s. Background subtraction of nonspecific binding was performed through measurement of association in buffer alone. Data analysis and curve fitting were performed using Octet software, version 7.0. Experimental data were fitted with the binding equations describing a 1:1 analyte-ligand interaction. Global analyses of the complete data sets, assuming binding was reversible (full dissociation), were carried out using nonlinear least-squares fitting allowing a single set of binding parameters to be obtained simultaneously for all concentrations of a given mAb dilution series.

Isothermal titration calorimetry. Isothermal titration calorimetry was carried out using a VP-ITC microcalorimeter (MicroCal/Malvern Instruments). In all titration experiments, the rPfCSP constructs and mAbs were prepared in PBS, pH 7.4. Each antibody solution, prepared at a concentration of ~40 µM (expressed per antigen binding site), was injected in 5 or 7 µl aliquots into the calorimetric cell containing the respective rPfCSP construct at a concentration of ~0.4 µM except for rPfCSP_5/3, which was prepared at 0.8 µM. All titrations were performed at 25° C. The exact concentrations of the reactants in each experiment were determined from the absorbance at 280 nm. The heat evolved upon each injection of antibody was obtained from the integral of the calorimetric signal. The heat associated with binding to the different rPfCSP constructs was obtained by subtracting the heat of dilution from the heat of reaction. The individual heats were plotted against the molar ratio, and the enthalpy change, $\Delta H$, the association constant, $K_a$ (the dissociation constant, $K_d = 1/K_a$) and the stoichiometry (valency of antigen binding sites), N, were obtained by nonlinear regression of the data to a model that takes into account the binding to either one or two sets of sites with different binding affinities. Gibbs energy, $\Delta G$, was calculated from the relation $\Delta G = -RT\ln K_a$, where R is the universal gas constant, (1.987 cal/(K×mol)) and T the absolute temperature in kelvin. The entropy contribution to Gibbs energy, $-T\Delta S$, was calculated from the known relation $\Delta G = \Delta H - T\Delta S$. The results were expressed per mole of antigen binding sites and the stoichiometry, N, denotes the number of antigen binding sites per mole of the respective rPfCSP construct.

FACS analysis of mAb binding to sporozoites. Freshly isolated Pb-PfCSP expressing GFP were purified across an Accudenz density gradient (Accurate Chemical) to remove mosquito debris as previously described (Kennedy et al. Malar J 11, 421, 2012) and resuspended in PBS containing the protease inhibitor E64 (Sigma-Aldrich) to prevent proteolytic processing of PfCSP. 8,000 SPZ were aliquoted to each well of a 96-well V-bottom plate (50 µl/well) and incubated for 30 min at 4° C. with various concentrations (0.02-20 µg/ml) of PfCSP-specific or control mAbs in PBS+E64, washed with 200 µl PBS+E64, and stained for 20 minutes at 4° C. with goat anti-human IgG-Alexa Fluor® 647 secondary antibody (Thermo Fisher Scientific) at a 1:1,000 dilution in PBS+E64. After washing with 200 µl PBS+E64 and fixation in 250 µl PBS with 0.5% paraformaldehyde, events were acquired on a modified LSR II (BD Biosciences).

Reduction of parasite liver burden after IV or ID challenge with Pb-PfCSP in albino mice. To measure mAb neutralization of SPZ and reduction of parasite burden in vivo, specified amounts of PfCSP-specific or control mAbs diluted in sterile filtered 1×PBS (pH 7.4; total volume 200 µl/mouse) were injected into the tail veins of 6- to 8-week old B6(Cg)-Tyrc-2J/J albino mice. For IV challenge, mice were then intravenously challenged in the tail vein with 2,000 freshly harvested transgenic P. berghei sporozoites expressing PfCSP and a green fluorescent protein/luciferase fusion protein (Pb-PfCSP GFP/Luc SPZ) 2 hours after mAb administration. 40-42 hours post-challenge, mice were injected intraperitoneally with 150 µl of D-Luciferin (30 mg/mL), anesthetized with isoflurane and imaged with the IVIS® Spectrum in vivo imaging system (PerkinElmer) 10 minutes after luciferin injection. Liver burden was quantified by analyzing a region of interest (ROI) in the upper abdominal region and determining the total flux or bioluminescent radiance (photons/sec) expressed by the transgenic Pb-PfCSP SPZ using the manufacturer's software (Living Image 4.5, PerkinElmer). For ID challenge, mice were intradermally challenged in the paw with 5,000 freshly harvested Pb-PfCSP GFP/Luc SPZ 72 hours after mAb administration. Seven days post-challenge, mice were imaged as described above in the IVIS. Parasitemia was quantified by analyzing the entire mouse as the ROI.

Parasitemia after mosquito bite challenge with Pb-PfCSP in albino mice. Anopheles stephensi female mosquitoes were allowed to feed on Swiss Webster mice infected with blood-stage Pb-PfCSP. Twenty days after infected bloodmeal, the proportion of infected mosquitoes was between 70-80%, as assessed by microscopic observation of 20 salivary glands. Based on this observation, it was determined that 6-7 mosquitoes were needed to expose mice to the bites of ~5 infected mosquitoes. 6-8 week old C57BL/6 female mice were injected IV with PfCSP mAbs (100, 300, or 600 µg mAb/mouse; blinded) diluted in 1×PBS (pH 7.4) in a total volume of 200 μL. Forty-eight hours after mAb administration, mice were subjected to a small tail vein bleed to ascertain pre-challenge mAb serum titers. Seventy-two hours after mAb administration, test and control mice were anesthetized with 2% Avertin (Alfa Aesar, Ward Hill, MA). Mosquitoes were allowed to feed on mice for 10 minutes. Following feeding, mosquito abdomens were inspected to confirm the blood meal. Mouse parasitemia was assessed daily through Giemsa staining of blood smears starting on day 4 and up to day 10-12 after exposure to infected mosquito bites.

In vivo protection in FRG-huHep mice. Female FRG-huHEP mice with engrafted human hepatocytes from two different donors (HHM19027 and HHM13022) were purchased from Yecuris, Inc. Repopulation of human hepatocytes were confirmed by the level of serum albumin and ranged between 4000 to 8000 μg/ml, evenly divided between the different experimental groups. Mice were intravenously injected with the indicated dose of VRC01 or PfCSP mAbs (100 μL per mouse) 24 hours before sporozoite challenge. On the day of sporozoite challenge, *Anopheles stephensi* mosquitoes infected with *P. falciparum* NF54 (on day 14-18 post blood meal) were dissected in Dutch modified RPMI 1640 media (ThermoFisher) to harvest sporozoites. 100,000 sporozoites (in a total volume of 100 μl) were injected IV in the tail vein of each mouse. Six days following challenge, serum was collected via cardiac bleed and livers of each mice were harvested using the method described in (Yang et al. Cell Rep 18, 3105-3116, 2017; Foquet et al. Malar. J. 12, 430, 2013). Briefly, lobes were pooled and emulsified to obtain single-cell suspension for subsequent genomic DNA (gDNA) extraction. gDNA were extracted from the chimeric livers (roughly 25% of the liver) and used to quantify parasite load using oligonucleotides specific for *P. falciparum* 18S rRNA as previously described (Yang et al. Cell Rep 18, 3105-3116, 2017; McCall et al. Sci Transl Med 9, 2017). qPCR was used to quantify the relative amount of human hepatocytes engrafted onto the mouse liver, as previously described (Alcoser et al. BMC Biotechnol 11, 124, 2011).

ELISA for quantitation of mAb concentrations in serum. Mice were bled 24 hours prior to challenge with five infected mosquito bites to assess circulating serum levels of passively transferred human PfCSP mAbs. ELISA was performed on mouse serum as previously described (Kisalu et al. Nat. Med. 24, 408-416, 2018) using rPfCSP-coated plates (200 ng/ml). A standard curve for each mAb was generated using eight two-fold serial dilutions of mAb starting at 10 ng/ml. Serum samples were applied at various dilutions in dilution/blocking buffer. For datapoints in the linear range of the standard curve, the average of the calculated concentration values was used for each individual sample.

Generation of Pb-PfCSP expressing GFP. GFP labeled Pb-PfCSP(GFP) parasites were generated by crossing the parental Pb-PfCSP line (Espinosa et al. NPJ Vaccines 2, 2017) with the previously described *P. berghei*-ConF parasite line that expresses GFP under the control of an HSP70 promotor (Amino et al. Cell Host Microbe 3, 88-96, 2008). Briefly, mice were coinfected with Pb-PfCSP and *P. berghei*-ConF at a ratio of 10:1. *Anopheles stephensi* mosquitoes were allowed to feed on the mice, and subsequently, sporozoites dissected from these mosquitoes were used to infect naive animals. Parasites expressing the GFP transgene were sorted from the blood of these mice by use of a FACSAria cell sorter and used to infect mice. Subsequently, the GFP progeny was cloned, and the clones screened for the insertion of the PfCSP knock-in via measurement of anti-PfCSP antibody binding to progeny sporozoites.

Multiphoton microscopy to analyze antibody activity in the liver. Mice received sequential IV injections of 30 μg of Alexa-405 labeled mAb (blinded), $1\times10^5$ Pb-PfCSP(GFP) SPZ, and rhodamine dextran (20 μg/ml, 50 μL). Mice were immediately prepared for multiphoton microscopy essentially as described (McNamara et al. Sci Immunol 2, 2017). Briefly, mice were anaesthetized with a mix of Ketamine (100 mg/kg) and Xylazine (10 mg/kg). The mouse temperature was maintained at 37° C. using a heating mat attached to feedback probe inserted in the mouse rectum throughout the surgery and imaging procedure. A lateral incision was made over the left lobe of the liver and any vessels cauterized by applying light pressure to the vessel until clotting occurred naturally. The mouse was then placed in a custom-made holder. The liver was exposed and directly adhered to a coverslip that was secured in the holder. Once stable, the preparation was transferred to a Fluoview FVMPE-RS multiphoton microscope system (Olympus) equipped with a XLPLN25XWMP2 objective (25×; NA1.05; water immersion; 2 mm working distance). For quantification of parasites and damaged hepatocytes, a single 50 μm Z-stack (2 μm/slice) was acquired using a resonance scanner. Fluorescence of AlexaFluor405, GFP and Rhodamine dextran were detected using an 860 nm wavelength laser. For videos, a sequence of between 1000-2000 50 μm Z-stacks (2 μm/slice) was acquired using a resonance scanner. Images were acquired using FV30 software (Olympus) and exported to Imaris (Bitplane) for downstream processing. Sporozoites and shed CSP length were measured using the measurement function on Imaris. Sporozoites were classified as either traversing, vessel bound or having established infection, based on certain criteria. Any sporozoite within 40 μm of at least one rhodamine$^+$ hepatocyte and still in contact with the traversed hepatocyte was considered to be traversing. If it was within 40 μm (i.e., diameter of a hepatocyte) of at least one rhodamine$^+$ hepatocyte but not in a vessel nor in contact with a rhodamine$^+$ hepatocyte, it had established infection. If it was not within 40 μm of a rhodamine$^+$ hepatocyte and located within a vessel, it was considered to be vessel bound in the sinusoid. In addition to this analysis, any sporozoite with a discontinuation of GFP along its length was classified as undergoing "dotty death." Parasite death observed in any of the resonance videos was characterized as bursting in the presence of a sudden loss of membrane integrity and release of GFP into the surrounding tissue.

NVDP conservation in global field isolates. PfCSP sequences and countries in which they were isolated were retrieved from GenBank. N- and C-terminal sequences were trimmed in Geneious Prime (Geneious) and the central repeat region sequences was exported into Microsoft Excel. All NPDP (SEQ ID NO: 29) tetrapeptides were transformed into 0, NANP repeats into 1, and NVDP repeats into 2; sequences were numerically ordered based on number of NVDP repeats and the continental region they were isolated in was indicated.

Heat map classifying the panel of human PfCSP mAbs. Numerical values for each parameter describing each of the seven mAbs in the panel were collated and ranked using conditional formatting (Microsoft Excel), with darker colors denoting improved performance and lighter colors indicating poorer performance. All numerical values that varied logarithmically were log-transformed into linear values to facilitate consistent analysis. The only categorical parameter (yes or no) was two-step binding.

Statistics. Unless otherwise stated, all mAbs were compared for significance to PBS or isotype control mAb using the Kruskal-Wallis test with Dunn's correction for multiple comparisons. For the PfSPZ challenge in FRG-huHep mice, the two-tailed Mann-Whitney test was used. For the mosquito bite challenge experiments, Kaplan-Meier curves for parasitemia were analyzed using the log-rank test and compared to L9. For measurement of PfCSP-specific monoclonal antibodies in mouse serum, standard curves were fitted with a hyperbolic parameter curve, and concentration values in the linear range of the standard curve were interpolated. For the ITC stoichiometry data, errors with 95% confidence were estimated from the fits of the data. Unless otherwise indicated, all data were plotted using GraphPad Prism, version 7.0.

It will be apparent that the precise details of the embodiments described may be varied or modified without departing from the spirit of the described embodiments. We claim all such modifications and variations that fall within the scope and spirit of the claims below.

It is claimed:

1. An isolated monoclonal antibody or an antigen binding fragment thereof, comprising:
a heavy chain variable region and a light chain variable region comprising a heavy chain complementarity determining region (HCDR) 1, a HCDR2, and a HCDR3, and a light chain complementarity determining region (LCDR) 1, a LCDR2, and a LCDR3 of the $V_H$ and $V_L$ set forth as SEQ ID NOs: 1 and 2, respectively; and
wherein the monoclonal antibody specifically binds to *P. falciparum* circumsporozoite protein (PfCSP) and neutralizes *P. falciparum*.

2. The antibody or an antigen binding fragment of claim 1, wherein the HCDR1, the HCDR2, the HCDR3, the LCDR1, the LCDR2, and the LCDR3 comprise the amino acid sequences set forth as SEQ ID NOs: 3, 4, 5, 6, 7, and 8, respectively.

3. The antibody or an antigen binding fragment of claim 2, wherein the $V_H$ and the $V_L$ comprise the amino acid sequences at least 90% identical to the amino acid sequences set forth as SEQ ID NOs: 1 and 2, respectively.

4. The antibody or an antigen binding fragment of claim 1, comprising a human framework region.

5. The antibody or an antigen binding fragment of claim 1, wherein the $V_H$ and the $V_L$ comprise the amino acid sequences set forth as (a) SEQ ID NOs: 1 and 2, respectively.

6. The antibody or an antigen binding fragment of claim 1, wherein the antibody comprises a human constant domain.

7. The antibody or an antigen binding fragment of claim 1, wherein the antibody is a human antibody.

8. The antibody or an antigen binding fragment of claim 1, wherein the antibody is an IgG.

9. The antibody or an antigen binding fragment of claim 8, wherein the antibody comprises heavy and light chains comprising the amino acid sequences set forth as SEQ ID NOs: 9 and 10, respectively (L9 IgG$_1$).

10. The antibody or an antigen binding fragment of claim 1, wherein the antibody comprises a recombinant constant domain comprising a modification that increases the half-life of the antibody.

11. The antibody of claim 10, wherein the modification increases binding to the neonatal Fc receptor.

12. The antibody of claim 11, wherein the recombinant constant domain is an IgG1 constant domain comprising M428L and N434S mutations.

13. An isolated antigen binding fragment of the antibody of claim 1, wherein the antigen binding fragment comprises the $V_H$ and the $V_L$ of the antibody, specifically binds to PfCSP, and neutralizes *P. falciparum*.

14. The antigen binding fragment of claim 13, wherein the antigen binding fragment is a Fv, Fab, F (ab') 2, scFV or a scFV$_2$ fragment.

15. The antibody or antigen binding fragment of claim 1, conjugated to an effector molecule or a detectable marker.

16. The antibody or antigen binding fragment of claim 1, wherein the antibody or antigen binding fragment inhibits *P. falciparum* sporozoite entry into the blood from the skin of the subject and/or inhibits *P. falciparum* sporozoite entry into hepatocytes in the liver of the subject.

17. A bispecific antibody comprising the antibody or antigen binding fragment of claim 1.

18. An isolated nucleic acid molecule encoding the antibody or antigen binding fragment of claim 1.

19. The nucleic acid molecule of claim 18, comprising the $V_H$ and the $V_L$ nucleotide sequences set forth as one of SEQ ID NOs: 11 and 12, respectively.

20. The nucleic acid molecule of claim 18, wherein the nucleic acid molecule comprises a cDNA sequence encoding the antibody or antigen binding fragment.

21. The nucleic acid molecule of claim 18, wherein the nucleic acid molecule is an RNA molecule encoding the antibody or antigen binding fragment.

22. The nucleic acid molecule of claim 18, operably linked to a promoter.

23. A vector comprising the nucleic acid molecule of claim 18.

24. An isolated host cell comprising the vector of claim 23.

25. A composition for use in inhibiting *P. falciparum* infection, comprising an effective amount of the monoclonal antibody of claim 1, an antigen binding fragment thereof, a nucleic acid molecule encoding the antibody, or vector comprising the nucleic acid molecule; and
a pharmaceutically acceptable carrier.

26. A method of producing an antibody or antigen binding fragment that specifically binds to PfCSP, comprising:
culturing the isolated host cell of claim 24 under suitable conditions that allow for the expression of the antibody or antigen binding fragment; and
purifying the antibody or antigen binding fragment.

27. A method of detecting the presence of *P. falciparum* in a biological sample from a human subject, comprising:
contacting the biological sample with an effective amount of the monoclonal antibody of claim 1 or an antigen binding fragment thereof, under conditions sufficient to form an immune complex; and
detecting the presence of the immune complex in the biological sample, wherein the presence of the immune complex in the biological sample indicates the presence of the *P. falciparum* in the sample.

28. The method of claim 27, wherein detecting the presence of the immune complex in the biological sample indicates that the subject has a *P. falciparum* infection.

29. A method of inhibiting a *P. falciparum* infection in a subject, comprising administering an effective amount of the monoclonal antibody or antigen binding fragment of claim 1, or a composition comprising the monoclonal antibody or antigen binding fragment of claim 1 to the subject, thereby inhibiting the *P. falciparum* infection in the subject.

30. The method of claim 29, wherein the method inhibits *P. falciparum* sporozoite entry into the blood from the skin of the subject and/or inhibits *P. falciparum* sporozoite entry into hepatocytes in the liver of the subject.

31. The method of claim 29, comprising administering the antibody to the subject.

* * * * *